(12) United States Patent
Balbas et al.

(10) Patent No.: US 10,206,911 B2
(45) Date of Patent: Feb. 19, 2019

(54) ANDROGEN RECEPTOR VARIANTS AND METHODS FOR MAKING AND USING

(71) Applicant: MEMORIAL SLOAN-KETTERING CANCER CENTER, New York, NY (US)

(72) Inventors: Minna D. Balbas, New York, NY (US); Charles L. Sawyers, New York, NY (US); Philip Watson, New York, NY (US)

(73) Assignee: Memorial Sloan-Kettering Cancer Center, New York, NY (US)

( * ) Notice: Subject to any disclaimer, the term of this patent is extended or adjusted under 35 U.S.C. 154(b) by 0 days.

(21) Appl. No.: 14/438,399

(22) PCT Filed: Oct. 25, 2013

(86) PCT No.: PCT/US2013/066982
§ 371 (c)(1),
(2) Date: Apr. 24, 2015

(87) PCT Pub. No.: WO2014/066864
PCT Pub. Date: May 1, 2014

(65) Prior Publication Data
US 2015/0265587 A1 Sep. 24, 2015

Related U.S. Application Data

(60) Provisional application No. 61/719,105, filed on Oct. 26, 2012.

(51) Int. Cl.
| | |
|---|---|
| *G01N 33/53* | (2006.01) |
| *A61K 31/4439* | (2006.01) |
| *C12Q 1/6886* | (2018.01) |
| *A61K 31/4166* | (2006.01) |
| *A61K 49/00* | (2006.01) |
| *C07K 14/705* | (2006.01) |
| *C07K 16/28* | (2006.01) |
| *C12N 15/113* | (2010.01) |
| *G01N 33/50* | (2006.01) |

(52) U.S. Cl.
CPC ...... *A61K 31/4439* (2013.01); *A61K 31/4166* (2013.01); *A61K 49/0008* (2013.01); *C07K 14/70567* (2013.01); *C07K 16/2857* (2013.01); *C12N 15/1138* (2013.01); *C12Q 1/6886* (2013.01); *G01N 33/5011* (2013.01); *C07K 2317/76* (2013.01); *C12N 2310/14* (2013.01); *C12Q 2600/106* (2013.01); *C12Q 2600/136* (2013.01); *C12Q 2600/156* (2013.01); *C12Q 2600/158* (2013.01); *G01N 2333/723* (2013.01)

(58) Field of Classification Search
None
See application file for complete search history.

(56) References Cited

U.S. PATENT DOCUMENTS

| | | | |
|---|---|---|---|
| 4,816,567 A | 3/1989 | Cabilly et al. | |
| 4,863,849 A | 9/1989 | Melamede | |
| 4,988,617 A | 1/1991 | Landegren et al. | |
| 5,010,175 A | 4/1991 | Rutter et al. | |
| 5,078,998 A | 1/1992 | Bevan et al. | |
| 5,091,513 A | 2/1992 | Huston et al. | |
| 5,223,409 A | 6/1993 | Ladner et al. | |
| 5,225,539 A | 7/1993 | Winter | |
| 5,288,514 A | 2/1994 | Ellman | |
| 5,302,509 A | 4/1994 | Cheeseman | |
| 5,322,770 A | 6/1994 | Gelfand | |
| 5,506,337 A | 4/1996 | Summerton et al. | |
| 5,519,134 A | 5/1996 | Acevedo et al. | |
| 5,525,735 A | 6/1996 | Gallop et al. | |
| 5,539,083 A | 7/1996 | Cook et al. | |
| 5,547,835 A | 8/1996 | Koster | |
| 5,549,974 A | 8/1996 | Holmes | |
| 5,569,588 A | 10/1996 | Ashby et al. | |
| 5,571,676 A | 11/1996 | Shuber | |
| 5,580,732 A | 12/1996 | Grossman et al. | |
| 5,585,089 A | 12/1996 | Queen et al. | |
| 5,593,853 A | 1/1997 | Chen et al. | |
| 5,605,798 A | 2/1997 | Koster | |
| 5,679,524 A | 10/1997 | Nikiforov et al. | |
| 5,693,761 A | 12/1997 | Queen et al. | |
| 5,693,762 A | 12/1997 | Queen et al. | |
| 5,740,341 A | 4/1998 | Oota et al. | |
| 5,869,619 A | 2/1999 | Studnicka | |
| 5,945,283 A | 8/1999 | Kwok et al. | |
| 6,180,370 B1 | 1/2001 | Queen et al. | |
| 6,232,107 B1 | 5/2001 | Bryan et al. | |
| 6,306,597 B1 | 10/2001 | Macevicz | |
| 6,548,640 B1 | 4/2003 | Winter | |
| 6,881,557 B2 | 4/2005 | Foote | |
| 6,982,321 B2 | 1/2006 | Winter | |

FOREIGN PATENT DOCUMENTS

| | | |
|---|---|---|
| EP | 1550720 A1 | 7/2005 |
| EP | 2631233 A1 | 8/2013 |

(Continued)

OTHER PUBLICATIONS

Balbas Minna, D. et al, Overcoming Mutation-Based Resistance to Antiandrogens with Rational Drug Design, eLIFE, 2: 1-21 (2013).

(Continued)

*Primary Examiner* — Michael D Pak
(74) *Attorney, Agent, or Firm* — Brenda Herschbach Jarrell; Choate, Hall & Stewart LLP

(57) ABSTRACT

The present invention encompasses the recognition that an F876L mutation of the androgen receptor (AR) gene confers resistance to the antiandrogens enzalutamide (MDV3100) and ARN-509 and is associated with incidence and/or risk of castration resistant prostate cancer (CRPC). The present invention also provides other AR polypeptide sequences associated with increased incidence and/or risk of CRPC. The present invention also provides screening methods for identification and/or characterization of novel AR polypeptide sequences associated with increased incidence and/or risk of CRPC via exposure to antiandrogens and for identification and/or characterization of agents to treat and/or reduce risk of CRPC by virtue of their effect on AR transcriptional activation.

4 Claims, 35 Drawing Sheets

Specification includes a Sequence Listing.

(56) References Cited

FOREIGN PATENT DOCUMENTS

| | | |
|---|---|---|
| JP | 2006/507841 A | 6/2011 |
| WO | WO-90/09455 A1 | 8/1990 |
| WO | WO-91/02087 A1 | 2/1991 |
| WO | WO-91/06678 A1 | 5/1991 |
| WO | WO-91/19735 A1 | 12/1991 |
| WO | WO-92/00091 A1 | 1/1992 |
| WO | WO-92/15712 A1 | 9/1992 |
| WO | WO-93/20242 A1 | 10/1993 |
| WO | WO-93/21340 A1 | 10/1993 |
| WO | WO-94/16101 A2 | 7/1994 |
| WO | WO-94/21822 A1 | 9/1994 |
| WO | WO-95/17676 A1 | 6/1995 |
| WO | WO-96/29431 A2 | 9/1996 |
| WO | WO-97/00271 A1 | 1/1997 |
| WO | WO-2005/060661 A2 | 7/2005 |
| WO | WO-2005/116204 A1 | 12/2005 |
| WO | WO-2012/053630 A1 | 4/2012 |
| WO | WO-2014/018926 A1 | 1/2014 |

OTHER PUBLICATIONS

Database EMBL (online), JP 2006507841-A/22771: Functional and Hyperfunctional siRNA (Jun. 22, 2011), retrieved from EBI accession No. EM_PAT: FZ665301.
Database EMBL (online), WO 2005116204-A441713: Double strand polynucleotides generating RNA interference (Apr. 19, 2011), retrieved from EBI accession No. EM_PAT: FZ035188.
Database Geneseq (online), Sense oligonucleotide #1 for LNCap gene (Nov. 6, 2003), retrieved from EBI accession No. GSN: ADA03158.
Hara, T. et al., Novel mutations of androgen receptor: a possible mechanism of bicalutamide withdrawal syndrome, Cancer Research, 63(1): 149-153 (2003).
International Search Report for PCT/US2013/066982, 10 pages (dated Jul. 7, 2014).
Joseph, J.D. et al., A clinically relevant androgen receptor mutation confers resistance to second-generation antiandrogens enzalutamide and ARN-509, Cancer Discovery, 3(9): 1020-1029 (2013).
Korpal, M. et al., An F876L mutation in androgen receptor confers genetic and phenotypic resistance to MDV3100 (Enzalutamide), Cancer Discovery, 3(9): 1030-1043 (2013).
Marcelli, M. et al., Androgen receptor mutations in prostate cancer, Cancer Research, 60: 944-949 (2000).
Taplin, M. et al., Selection for androgen receptor mutations in prostate cancers treated with androgen antagonist, Cancer Research, 59(11): 2511-2515 (1999).
Tilley, W.D. et al., Mutations in the androgen receptor gene are associated with progression of human prostate cancer to androgen independence, Clin Cancer Res. 2:277-285 (1996).
Written Opinion for PCT/US2013/066982, 15 pages (dated Jul. 7, 2014).
Baum, Rudy, Solid-phase synthesis of benzodiazepines, C&EN, Science/Technology, pp. 33-34 (1993).
Bayly, C. et al., A well-behaved electrostatic potential based method using charge restraints for deriving atomic charges: the RESP model, J. Phys. Chem., 97:10269-10280 (1993).
Brooks, B. et al., CHARMM: A Program for Macromolecular Energy, Minimization, and Dynamics Calculations, J. Comput Chem, 4:187-217 (1983).
Brooks, B. et al., CHARMM: the biomolecular simulation program, J Comput Chem, 30(10):1545-614 (2009).
Campbell, D. and Bermak, J. Phosphonate Ester Synthesis Using a Modified Mitsunobu Condensation, J. Org. Chem., 59:658-660 (1994).
Canard, B. and Sarfati, R., DNA polymerase fluorescent substrates with reversible 3'-tags, Gene, 148(1):1-6 (1994).
Carell, T. et al., A Novel Procedure for the Synthesis of Libraries Containing Small Organic Molecules, Angew. Chem. Int. Ed. Engl., 33(20):2059-2061 (1994).
Carell, T. et al., A Solution-Phase Screening Procedure for the Isolation of Active Compounds from a Library of Molecules, Angew. Chem. Int. Ed. Eng., 33:2061-2064 (1994).
Chapel-Fernandes, S. et al., Use of the PSA enhancer core element to modulate the expression of prostate- and non-prostate-specific basal promoters in a lentiviral vector context, Cancer Gene Ther, 13(10):919-29 (2006).
Chen, C. et al., "Analogous" Organic Synthesis of Small-Compound Libraries: Validation of Combinatorial Chemistry in Small-Molecule Synthesis, J. Amer. Chem. Soc., 116:2661-2662 (1994).
Cho, C. et al., An unnatural biopolymer, Science, 261(5126):1303-5 (1993).
Cohen, A. et al., Emerging technologies for sequencing antisense oligonucleotides: capillary electrophoresis and mass spectrometry, Adv Chromatogr, 36:127-62 (1996).
Cornell, W. et al., Application of RESP charges to calculate conformational energies, hydrogen bond energies, and free energies of solvation, J. Am. Chem Soc., 115:9620-9631 (1993).
Cull, M. et al., Screening for receptor ligands using large libraries of peptides linked to the C terminus of the lac repressor, Proc Natl Acad Sci USA, 89(5):1865-9 (1992).
Cwirla, S. et al., Peptides on phage: a vast library of peptides for identifying ligands, Proc Natl Acad Sci USA, 87(16):6378-82 (1990).
Devlin, J. et al., Random peptide libraries: a source of specific protein binding molecules, Science, 249(4967):404-6 (1990).
Dykxhoorn, D. et al., Killing the messenger: short RNAs that silence gene expression, Nat Rev Mol Cell Biol, 4(6):457-67 (2003).
Erb, E. et al., Recursive deconvolution of combinatorial chemical libraries, Proc Natl Acad Sci USA, 91(24):11422-6 (1994).
Felici, A. et al., A changing landscape in castration-resistant prostate cancer treatment, Front Endocrinol (Lausanne), 3:85, 8 pages, (2012).
Felici, F. et al., Selection of antibody ligands from a large library of oligopeptides expressed on a multivalent exposition vector, J Mol Biol, 222(2):301-10 (1991).
Fodor, S. et al., Multiplexed biochemical assays with biological chips, Nature, 364(6437):555-6 (1993).
Furka, A. et al., General method for rapid synthesis of multicomponent peptide mixtures, Int J Pept Protein Res, 37(6):487-93 (1991).
Gallop, M. et al., Applications of combinatorial technologies to drug discovery. 1. Background and peptide combinatorial libraries, J Med Chem, 37(9):1233-51 (1994).
Gluzman, Yakov, SV40-Transformed Simian Cells Support the Replication of Early SV40 Mutants, Cell, 23(1):175-82 (1981).
Gossen, M. and Bujard, H., Tight control of gene expression in mammalian cells by tetracycline-responsive promoters, Proc Natl Acad Sci USA, 89(12):5547-51 (1992).
Griffin, H. and Griffin, A., DNA sequencing. Recent innovations and future trends, Appl Biochem Biotechnol, 38(1-2):147-59 (1993).
Hagihara, M. et al., Vinylogous Polypeptides: An Alternative Peptide Backbone, J. Amer. Chem. Soc., 114:6568-6570 (1992).
Hannon, G. and Rossi, J., Unlocking the potential of the human genome with RNA interference, Nature, 431(7006):371-8 (2004).
Hirschmann, R. et al., Nonpeptidal Peptidomimetics with a β-D-Glucose Scaffolding. A Partial Somatostatin Agonist Bearing a Close Structural Relationship to a Potent, Selective Substance p. Antagonist, J. Amer. Chem. Soc., 114:9217-9218 (1992).
Hobbs Dewitt, S. et al., "Diversomers": an approach to nonpeptide, nonoligomeric chemical diversity, Proc Natl Acad Sci USA, 90(15):6909-13 (1993).
Houghten, R. et al., Generation and use of synthetic peptide combinatorial libraries for basic research and drug discovery, Nature, 354(6348):84-6 (1991).
Houghten, R. et al., The use of synthetic peptide combinatorial libraries for the identification of bioactive peptides, Biotechniques, 13(3):412-21 (1992).
Koboldt, D. et al., VarScan 2: somatic mutation and copy No. alteration discovery in cancer by exome sequencing, Genome Res, 22(3):568-76 (2012).

(56) References Cited

OTHER PUBLICATIONS

Kohler, G. and Milstein, C., Continuous cultures of fused cells secreting antibody of predefined specificity, Nature, 256(5517):495-7 (1975).

Lam, K. et al., A new type of synthetic peptide library for identifying ligand-binding activity, Nature, 354(6348):82-4 (1991).

Lam, Kit S., Application of combinatorial library methods in cancer research and drug discovery, Anticancer Drug Des, 12(3):145-67 (1997).

Lander, E. et al., Initial sequencing and analysis of the human genome, Nature, 409(6822):860-921 (2001).

Li, H. and Durbin, R., Fast and accurate short read alignment with Burrows-Wheeler transform, Bioinformatics, 25(14):1754-60 (2009).

Li, H. et al., The Sequence Alignment/Map format and SAMtools, Bioinformatics, 25(16):2078-9 (2009).

Liang, R. et al., Parallel synthesis and screening of a solid phase carbohydrate library, Science, 274(5292):1520-2 (1996).

Maxam, A. and Gilbert, W., A new method for sequencing DNA, Proc Natl Acad Sci USA, 74(2):560-4 (1977).

Meister, G. and Tuschl, T., Mechanisms of gene silencing by double-stranded RNA, Nature, 431(7006):343-9 (2004).

Metzker, M. et al., Termination of DNA synthesis by novel 3'-modified-deoxyribonucleoside 5'-triphosphates, Nucleic Acids Res, 22(20):4259-67 (1994).

Momany, F. and Rone, R., Validation of the general purpose QUANTA 3.2/CHARMmforce field, J. Comput. Chem., 13:888-900 (1992).

Ozers, M. et al., The androgen receptor T877A mutant recruits LXXLL and FXXLF peptides differently than wild-type androgen receptor in a time-resolved fluorescence resonance energy transfer assay, Biochemistry, 46(3):683-95 (2007).

Pettersen, E. et al., UCSF Chimera—a visualization system for exploratory research and analysis, J Comput Chem, 25(13):1605-12 (2004).

Sanger, F. et al., DNA sequencing with chain-terminating inhibitors, Proc Natl Acad Sci USA, 74(12):5463-7 (1977).

Scott, J. and Smith, G., Searching for peptide ligands with an epitope library, Science, 249(4967):386-90 (1990).

Smith, D. and Johnson, K., Single-step purification of polypeptides expressed in *Escherichia coli* as fusions with glutathione S-transferase, Gene, 67(1):31-40 (1988).

Tran, C. et al., Development of a second-generation antiandrogen for treatment of advanced prostate cancer, Science, 324(5928):787-90 (2009).

Trapnell, C. et al., TopHat: discovering splice junctions with RNA-Seq, Bioinformatics, 25(9):1105-11 (2009).

Vaughan, T. et al., Human antibodies with sub-nanomolar affinities isolated from a large non-immunized phage display library, Nat Biotechnol, 14(3):309-14 (1996).

Venter, J., et al., The sequence of the human genome, Science, 291(5507):1304-51 (2001).

Watson, P. et al., Constitutively active androgen receptor splice variants expressed in castration-resistant prostate cancer require full-length androgen receptor, Proc Natl Acad Sci USA, 107(39):16759-65 (2010).

Welsbie, D. et al., Histone deacetylases are required for androgen receptor function in hormone-sensitive and castrate-resistant prostate cancer, Cancer Res, 69(3):958-66 (2009).

Zuckermann, R. et al., Discovery of nanomolar ligands for 7-transmembrane G-protein-coupled receptors from a diverse N-(substituted)glycine peptoid library, J Med Chem, 37(17):2678-85 (1994).

|  | F876 MUTATION * | TREATMENT |
|---|---|---|
| CWR22PC (IN VITRO) | 52% OF ALL READS | ENZALUTAMIDE |
|  | 1.3% OF ALL READS | ARN-509 |
|  | NOT DETECTED | VEHICLE |
| LNCaP/AR (IN VIVO) | 3/8 TUMORS * | ENZALUTAMIDE |
|  | 3/14 TUMORS | ARN-509 |
|  | 0/5 TUMORS | VEHICLE |
| * 1 TUMOR F876I, ALL OTHERS F876L | | |

SEQUENCE LISTING

```
<160> NUMBER OF SEQ ID NOS: 53

<210> SEQ ID NO 1
<211> LENGTH: 919
<212> TYPE: PRT
<213> ORGANISM: Homo sapiens

<400> SEQUENCE: 1

Met Glu Val Gln Leu Gly Leu Gly Arg Val Tyr Pro Arg Pro Pro Ser
1               5                   10                  15

Lys Thr Tyr Arg Gly Ala Phe Gln Asn Leu Phe Gln Ser Val Arg Glu
            20                  25                  30

Val Ile Gln Asn Pro Gly Pro Arg His Pro Glu Ala Ala Ser Ala Ala
        35                  40                  45
```

```
Pro Pro Gly Ala Ser Leu Leu Leu Gln Gln Gln Gln Gln Gln
    50                  55                  60
Gln Gln Gln Gln Gln Gln Gln Gln Gln Gln Gln Gln Glu Thr
 65                  70                  75                  80
Ser Pro Arg Gln Gln Gln Gln Gln Gly Glu Asp Gly Ser Pro Gln
                 85                  90                  95
Ala His Arg Arg Gly Pro Thr Gly Tyr Leu Val Leu Asp Glu Gln
                100                 105                 110
Gln Pro Ser Gln Pro Gln Ser Ala Leu Glu Cys His Pro Glu Arg Gly
             115                 120                 125
Cys Val Pro Glu Pro Gly Ala Ala Val Ala Ala Ser Lys Gly Leu Pro
130                 135                 140
Gln Gln Leu Pro Ala Pro Pro Asp Glu Asp Asp Ser Ala Ala Pro Ser
145                 150                 155                 160
Thr Leu Ser Leu Leu Gly Pro Thr Phe Pro Gly Leu Ser Ser Cys Ser
                165                 170                 175
Ala Asp Leu Lys Asp Ile Leu Ser Glu Ala Ser Thr Met Gln Leu Leu
            180                 185                 190
Gln Gln Gln Gln Gln Glu Ala Val Ser Glu Gly Ser Ser Ser Gly Arg
    195                 200                 205
Ala Arg Glu Ala Ser Gly Ala Pro Thr Ser Ser Lys Asp Asn Tyr Leu
210                 215                 220
Gly Gly Thr Ser Thr Ile Ser Asp Asn Ala Lys Glu Leu Cys Lys Ala
225                 230                 235                 240
Val Ser Val Ser Met Gly Leu Gly Val Glu Ala Leu Glu His Leu Ser
                245                 250                 255
Pro Gly Glu Gln Leu Arg Gly Asp Cys Met Tyr Ala Pro Leu Leu Gly
                260                 265                 270
Val Pro Pro Ala Val Arg Pro Thr Pro Cys Ala Pro Leu Ala Glu Cys
            275                 280                 285
Lys Gly Ser Leu Leu Asp Asp Ser Ala Gly Lys Ser Thr Glu Asp Thr
    290                 295                 300
Ala Glu Tyr Ser Pro Phe Lys Gly Gly Tyr Thr Lys Gly Leu Glu Gly
305                 310                 315                 320
Glu Ser Leu Gly Cys Ser Gly Ser Ala Ala Gly Ser Ser Gly Thr
                325                 330                 335
Leu Glu Leu Pro Ser Thr Leu Ser Leu Tyr Lys Ser Gly Ala Leu Asp
                340                 345                 350
Glu Ala Ala Tyr Gln Ser Arg Asp Tyr Tyr Asn Phe Pro Leu Ala
            355                 360                 365
Leu Ala Gly Pro Pro Pro Pro Pro Pro His Pro His Ala Arg
            370                 375                 380
Ile Lys Leu Glu Asn Pro Leu Asp Tyr Gly Ser Ala Trp Ala Ala
385                 390                 395                 400
Ala Ala Gln Cys Arg Tyr Gly Asp Leu Ala Ser Leu His Gly Ala
                405                 410                 415
Ala Ala Gly Pro Gly Ser Gly Ser Pro Ser Ala Ala Ser Ser Ser
            420                 425                 430
Trp His Thr Leu Phe Thr Ala Glu Glu Gly Gln Leu Tyr Gly Pro Cys
    435                 440                 445
Gly Gly Gly Gly Gly Gly Gly Gly Gly Gly Gly Gly Gly Gly
450                 455                 460
```

```
Gly Gly Gly Gly Gly Gly Gly Glu Ala Gly Ala Val Ala Pro Tyr
465                 470                 475                 480

Gly Tyr Thr Arg Pro Pro Gln Gly Leu Ala Gly Gln Glu Ser Asp Phe
                485                 490                 495

Thr Ala Pro Asp Val Trp Tyr Pro Gly Gly Met Val Ser Arg Val Pro
            500                 505                 510

Tyr Pro Ser Pro Thr Cys Val Lys Ser Glu Met Gly Pro Trp Met Asp
            515                 520                 525

Ser Tyr Ser Gly Pro Tyr Gly Asp Met Arg Leu Glu Thr Ala Arg Asp
        530                 535                 540

His Val Leu Pro Ile Asp Tyr Tyr Phe Pro Pro Gln Lys Thr Cys Leu
545                 550                 555                 560

Ile Cys Gly Asp Glu Ala Ser Gly Cys His Tyr Gly Ala Leu Thr Cys
                565                 570                 575

Gly Ser Cys Lys Val Phe Phe Lys Arg Ala Ala Glu Gly Lys Gln Lys
            580                 585                 590

Tyr Leu Cys Ala Ser Arg Asn Asp Cys Thr Ile Asp Lys Phe Arg Arg
        595                 600                 605

Lys Asn Cys Pro Ser Cys Arg Leu Arg Lys Cys Tyr Glu Ala Gly Met
    610                 615                 620

Thr Leu Gly Ala Arg Lys Leu Lys Lys Leu Gly Asn Leu Lys Leu Gln
625                 630                 635                 640

Glu Glu Gly Glu Ala Ser Ser Thr Thr Ser Pro Thr Glu Glu Thr Thr
                645                 650                 655

Gln Lys Leu Thr Val Ser His Ile Glu Gly Tyr Glu Cys Gln Pro Ile
            660                 665                 670

Phe Leu Asn Val Leu Glu Ala Ile Glu Pro Gly Val Val Cys Ala Gly
            675                 680                 685

His Asp Asn Asn Gln Pro Asp Ser Phe Ala Ala Leu Leu Ser Ser Leu
690                 695                 700

Asn Glu Leu Gly Glu Arg Gln Leu Val His Val Val Lys Trp Ala Lys
705                 710                 715                 720

Ala Leu Pro Gly Phe Arg Asn Leu His Val Asp Asp Gln Met Ala Val
            725                 730                 735

Ile Gln Tyr Ser Trp Met Gly Leu Met Val Phe Ala Met Gly Trp Arg
        740                 745                 750

Ser Phe Thr Asn Val Asn Ser Arg Met Leu Tyr Phe Ala Pro Asp Leu
    755                 760                 765

Val Phe Asn Glu Tyr Arg Met His Lys Ser Arg Met Tyr Ser Gln Cys
770                 775                 780

Val Arg Met Arg His Leu Ser Gln Glu Phe Gly Trp Leu Gln Ile Thr
785                 790                 795                 800

Pro Gln Glu Phe Leu Cys Met Lys Ala Leu Leu Leu Phe Ser Ile Ile
            805                 810                 815

Pro Val Asp Gly Leu Lys Asn Gln Lys Phe Phe Asp Glu Leu Arg Met
        820                 825                 830

Asn Tyr Ile Lys Glu Leu Asp Arg Ile Ile Ala Cys Lys Arg Lys Asn
    835                 840                 845

Pro Thr Ser Cys Ser Arg Arg Phe Tyr Gln Leu Thr Lys Leu Leu Asp
850                 855                 860

Ser Val Gln Pro Ile Ala Arg Glu Leu His Gln Phe Thr Phe Asp Leu
865                 870                 875                 880
```

Leu Ile Lys Ser His Met Val Ser Val Asp Phe Pro Glu Met Met Ala
                885                 890                 895

Glu Ile Ile Ser Val Gln Val Pro Lys Ile Leu Ser Gly Lys Val Lys
        900                 905                 910

Pro Ile Tyr Phe His Thr Gln
        915

<210> SEQ ID NO 2
<211> LENGTH: 3569
<212> TYPE: DNA
<213> ORGANISM: Homo sapiens

<400> SEQUENCE: 2

| | | | | | |
|---|---|---|---|---|---|
| taataactca | gttcttattt | gcacctactt | cagtggacac | tgaatttgga | aggtggagga | 60 |
| ttttgttttt | ttcttttaag | atctgggcat | cttttgaatc | tacccttcaa | gtattaagag | 120 |
| acagactgtg | agcctagcag | ggcagatctt | gtccaccgtg | tgtcttcttc | tgcacgagac | 180 |
| tttgaggctg | tcagagcgct | ttttgcgtgg | ttgctcccgc | aagtttcctt | ctctggagct | 240 |
| tcccgcaggt | gggcagctag | ctgcagcgac | taccgcatca | tcacagcctg | ttgaactctt | 300 |
| ctgagcaaga | gaaggggagg | cggggtaagg | gaagtaggtg | gaagattcag | ccaagctcaa | 360 |
| ggatggaagt | gcagttaggg | ctgggaaggg | tctaccctcg | gccgccgtcc | aagacctacc | 420 |
| gaggagcttt | ccagaatctg | ttccagagcg | tgcgcgaagt | gatccagaac | ccgggcccca | 480 |
| ggcacccaga | ggccgcgagc | gcagcacctc | ccggcgccag | tttgctgctg | ctgcagcagc | 540 |
| agcagcagca | gcagcagcag | cagcagcagc | agcagcagca | gcagcagcag | cagcaagaga | 600 |
| ctagccccag | gcagcagcag | cagcagcagg | gtgaggatgg | ttctcccaa | gcccatcgta | 660 |
| gaggccccac | aggctacctg | gtcctggatg | aggaacagca | accttcacag | ccgcagtcgg | 720 |
| ccctggagtg | ccaccccgag | agaggttgcg | tcccagagcc | tggagccgcc | gtggccgcca | 780 |
| gcaaggggct | gccgcagcag | ctgccagcac | ctcggacga | ggatgactca | gctgccccat | 840 |
| ccacgttgtc | cctgctgggc | cccactttcc | ccggcttaag | cagctgctcc | gctgaccta | 900 |
| aagacatcct | gagcgaggcc | agcaccatgc | aactccttca | gcaacagcag | caggaagcag | 960 |
| tatccgaagg | cagcagcagc | gggagagcga | ggaggcctc | gggggctccc | acttcctcca | 1020 |
| aggacaatta | cttaggggc | acttcgacca | tttctgacaa | cgccaaggag | ttgtgtaagg | 1080 |
| cagtgtcggt | gtccatgggc | ctgggtgtgg | aggcgttgga | gcatctgagt | ccaggggaac | 1140 |
| agcttcgggg | ggattgcatg | tacgccccac | ttttgggagt | tccacccgct | gtgcgtccca | 1200 |
| ctccttgtgc | cccattggcc | gaatgcaaag | gttctctgct | agacgacagc | gcaggcaaga | 1260 |
| gcactgaaga | tactgctgag | tattcccctt | tcaagggagg | ttacaccaaa | gggctagaag | 1320 |
| gcgagagcct | aggctgctct | ggcagcgctg | cagcagggag | ctccgggaca | cttgaactgc | 1380 |
| cgtctaccct | gtctctctac | aagtccggag | cactggacga | ggcagctgcg | taccagagtc | 1440 |
| gcgactacta | caactttcca | ctggctctgg | ccggaccgcc | gccccctccg | ccgcctcccc | 1500 |
| atccccacgc | tcgcatcaag | ctggagaacc | cgctggacta | cggcagcgcc | tgggcggctg | 1560 |
| cggcggcgca | gtgccgctat | ggggacctgg | cgagcctgca | tggcgcgggt | gcagcgggac | 1620 |
| ccggttctgg | gtcaccctca | gccgccgctt | cctcatcctg | gcacactctc | ttcacagccg | 1680 |
| aagaaggcca | gttgtatgga | ccgtgtggtg | gtggtgggg | tggtggcggc | ggcggcggcg | 1740 |
| gcggcggcgc | cggcggcggc | ggcggcggcg | gcggcggcga | gcgggagct | gtagcccct | 1800 |
| acggctacac | tcggcccct | caggggctgg | cgggccagga | aagcgacttc | accgcacctg | 1860 |

```
atgtgtggta ccctggcggc atggtgagca gagtgcccta tcccagtccc acttgtgtca   1920
aaagcgaaat gggcccctgg atggatagct actccggacc ttacgggac atgcgtttgg    1980
agactgccag ggaccatgtt tgcccattg actattactt tccaccccag aagacctgcc    2040
tgatctgtgg agatgaagct tctgggtgtc actatgagc tctcacatgt ggaagctgca    2100
aggtcttctt caaaagagcc gctgaaggga acagaagta cctgtgcgcc agcagaaatg    2160
attgcactat tgataaattc cgaaggaaaa attgtccatc ttgtcgtctt cggaaatgtt   2220
atgaagcagg gatgactctg ggagcccgga agctgaagaa acttggtaat ctgaaactac   2280
aggaggaagg agaggcttcc agcaccacca gccccactga ggagacaacc cagaagctga   2340
cagtgtcaca cattgaaggc tatgaatgtc agcccatctt tctgaatgtc ctggaagcca   2400
ttgagccagg tgtagtgtgt gctggacacg acaacaacca gcccgactcc tttgcagcct   2460
tgctctctag cctcaatgaa ctgggagaga gacagcttgt acacgtggtc aagtgggcca   2520
aggccttgcc tggcttccgc aacttacacg tggacgacca gatggctgtc attcagtact   2580
cctggatggg gctcatggtg tttgccatgg gctggcgatc cttcaccaat gtcaactcca   2640
ggatgctcta cttcgcccct gatctggttt tcaatgagta ccgcatgcac aagtcccgga   2700
tgtacagcca gtgtgtccga atgaggcacc tctctcaaga gtttggatgg ctccaaatca   2760
cccccccagga attcctgtgc atgaaagcac tgctactctt cagcattatt ccagtggatg   2820
ggctgaaaaa tcaaaaattc tttgatgaac ttcgaatgaa ctacatcaag gaactcgatc   2880
gtatcattgc atgcaaaaga aaaaatccca catcctgctc aagacgcttc taccagctca   2940
ccaagctcct ggactccgtg cagcctattg cgagagagct gcatcagttc acttttgacc   3000
tgctaatcaa gtcacacatg gtgagcgtgg actttccgga aatgatggca gagatcatct   3060
ctgtgcaagt gcccaagatc ctttctggga agtcaagcc catctatttc cacacccagt   3120
gaagcattgg aaaccctatt tccccacccc agctcatgcc ccctttcaga tgtcttctgc   3180
ctgttataac tctgcactac tcctctgcag tgccttgggg aatttcctct attgatgtac   3240
agtctgtcat gaacatgttc ctgaattcta tttgctgggc ttttttttc tctttctctc    3300
cttttttttt cttcttccct ccctatctaa ccctcccatg gcaccttcag actttgcttc   3360
ccattgtggc tcctatctgt gttttgaatg gtgttgtatg cctttaaatc tgtgatgatc   3420
ctcatatggc ccagtgtcaa gttgtgcttg tttacagcac tactctgtgc cagccacaca   3480
aacgtttact tatcttatgc cacgggaagt ttagagagct aagattatct ggggaaatca   3540
aaacaaaaaa caagcaaaca aaaaaaaaa                                     3569
```

<210> SEQ ID NO 3
<211> LENGTH: 31
<212> TYPE: DNA
<213> ORGANISM: Artificial Sequence
<220> FEATURE:
<223> OTHER INFORMATION: chemically synthesized oligonucleotide

<400> SEQUENCE: 3
cattcagtac tcctgcatgg ggctcatggt g                                  31

<210> SEQ ID NO 4
<211> LENGTH: 31
<212> TYPE: DNA
<213> ORGANISM: Artificial Sequence
<220> FEATURE:
<223> OTHER INFORMATION: chemically synthesized oligonucleotide

```
<400> SEQUENCE: 4
caccatgagc cccatgcagg agtactgaat g                              31

<210> SEQ ID NO 5
<211> LENGTH: 35
<212> TYPE: DNA
<213> ORGANISM: Artificial Sequence
<220> FEATURE:
<223> OTHER INFORMATION: chemically synthesized oligonucleotide

<400> SEQUENCE: 5
gagagctgca tcagttcgct tttgacctgc taatc                          35

<210> SEQ ID NO 6
<211> LENGTH: 35
<212> TYPE: DNA
<213> ORGANISM: Artificial Sequence
<220> FEATURE:
<223> OTHER INFORMATION: chemically synthesized oligonucleotide

<400> SEQUENCE: 6
gattagcagg tcaaaagcga actgatgcag ctctc                          35

<210> SEQ ID NO 7
<211> LENGTH: 34
<212> TYPE: DNA
<213> ORGANISM: Artificial Sequence
<220> FEATURE:
<223> OTHER INFORMATION: chemically synthesized oligonucleotide

<400> SEQUENCE: 7
cgagagagct gcatcagctc acttttgacc tgct                           34

<210> SEQ ID NO 8
<211> LENGTH: 34
<212> TYPE: DNA
<213> ORGANISM: Artificial Sequence
<220> FEATURE:
<223> OTHER INFORMATION: chemically synthesized oligonucleotide

<400> SEQUENCE: 8
agcaggtcaa aagtgagctg atgcagctct ctcg                           34

<210> SEQ ID NO 9
<211> LENGTH: 35
<212> TYPE: DNA
<213> ORGANISM: Artificial Sequence
<220> FEATURE:
<223> OTHER INFORMATION: chemically synthesized oligonucleotide

<400> SEQUENCE: 9
gagagagctg catcagtgca cttttgacct gctaa                          35

<210> SEQ ID NO 10
<211> LENGTH: 35
<212> TYPE: DNA
<213> ORGANISM: Artificial Sequence
<220> FEATURE:
<223> OTHER INFORMATION: chemically synthesized oligonucleotide

<400> SEQUENCE: 10
ttagcaggtc aaaagtgcac tgatgcagct ctctc                          35
```

<210> SEQ ID NO 11
<211> LENGTH: 35
<212> TYPE: DNA
<213> ORGANISM: Artificial Sequence
<220> FEATURE:
<223> OTHER INFORMATION: chemically synthesized oligonucleotide

<400> SEQUENCE: 11
cgagagagct gcatcagatc acttttgacc tgcta                    35

<210> SEQ ID NO 12
<211> LENGTH: 35
<212> TYPE: DNA
<213> ORGANISM: Artificial Sequence
<220> FEATURE:
<223> OTHER INFORMATION: chemically synthesized oligonucleotide

<400> SEQUENCE: 12
tagcaggtca aaagtgatct gatgcagctc tctcg                    35

<210> SEQ ID NO 13
<211> LENGTH: 36
<212> TYPE: DNA
<213> ORGANISM: Artificial Sequence
<220> FEATURE:
<223> OTHER INFORMATION: chemically synthesized oligonucleotide

<400> SEQUENCE: 13
cgagagagct gcatcagtcc acttttgacc tgctaa                   36

<210> SEQ ID NO 14
<211> LENGTH: 36
<212> TYPE: DNA
<213> ORGANISM: Artificial Sequence
<220> FEATURE:
<223> OTHER INFORMATION: chemically synthesized oligonucleotide

<400> SEQUENCE: 14
ttagcaggtc aaaagtggac tgatgcagct ctctcg                   36

<210> SEQ ID NO 15
<211> LENGTH: 35
<212> TYPE: DNA
<213> ORGANISM: Artificial Sequence
<220> FEATURE:
<223> OTHER INFORMATION: chemically synthesized oligonucleotide

<400> SEQUENCE: 15
cgagagagct gcatcaggtc acttttgacc tgcta                    35

<210> SEQ ID NO 16
<211> LENGTH: 35
<212> TYPE: DNA
<213> ORGANISM: Artificial Sequence
<220> FEATURE:
<223> OTHER INFORMATION: chemically synthesized oligonucleotide

<400> SEQUENCE: 16
tagcaggtca aaagtgacct gatgcagctc tctcg                    35

<210> SEQ ID NO 17
<211> LENGTH: 38
<212> TYPE: DNA
<213> ORGANISM: Artificial Sequence
<220> FEATURE:
<223> OTHER INFORMATION: chemically synthesized oligonucleotide

```
<400> SEQUENCE: 17
tgcgagagag ctgcatcagt acacttttga cctgctaa                              38

<210> SEQ ID NO 18
<211> LENGTH: 38
<212> TYPE: DNA
<213> ORGANISM: Artificial Sequence
<220> FEATURE:
<223> OTHER INFORMATION: chemically synthesized oligonucleotide

<400> SEQUENCE: 18
ttagcaggtc aaaagtgtac tgatgcagct ctctcgca                              38

<210> SEQ ID NO 19
<211> LENGTH: 31
<212> TYPE: DNA
<213> ORGANISM: Artificial Sequence
<220> FEATURE:
<223> OTHER INFORMATION: chemically synthesized oligonucleotide

<400> SEQUENCE: 19
acagcttgta cacgtcgtca agtgggccaa g                                     31

<210> SEQ ID NO 20
<211> LENGTH: 31
<212> TYPE: DNA
<213> ORGANISM: Artificial Sequence
<220> FEATURE:
<223> OTHER INFORMATION: chemically synthesized oligonucleotide

<400> SEQUENCE: 20
acagcttgta cacgtcgtga agtgggccaa g                                     31

<210> SEQ ID NO 21
<211> LENGTH: 33
<212> TYPE: DNA
<213> ORGANISM: Artificial Sequence
<220> FEATURE:
<223> OTHER INFORMATION: chemically synthesized oligonucleotide

<400> SEQUENCE: 21
taccgcatgc acaagtcgcg gatgtacagc cag                                   33

<210> SEQ ID NO 22
<211> LENGTH: 33
<212> TYPE: DNA
<213> ORGANISM: Artificial Sequence
<220> FEATURE:
<223> OTHER INFORMATION: chemically synthesized oligonucleotide

<400> SEQUENCE: 22
taccgcatgc acaagtcgcg catgtacagc cag                                   33

<210> SEQ ID NO 23
<211> LENGTH: 20
<212> TYPE: DNA
<213> ORGANISM: Artificial Sequence
<220> FEATURE:
<223> OTHER INFORMATION: chemically synthesized oligonucleotide

<400> SEQUENCE: 23
gtcccctaca tcgtgacctg                                                  20
```

```
<210> SEQ ID NO 24
<211> LENGTH: 20
<212> TYPE: DNA
<213> ORGANISM: Artificial Sequence
<220> FEATURE:
<223> OTHER INFORMATION: chemically synthesized oligonucleotide

<400> SEQUENCE: 24
gaggttcaag ggggagagac                                                   20

<210> SEQ ID NO 25
<211> LENGTH: 23
<212> TYPE: DNA
<213> ORGANISM: Artificial Sequence
<220> FEATURE:
<223> OTHER INFORMATION: chemically synthesized oligonucleotide

<400> SEQUENCE: 25
agagacagct tgtacacgtc gtg                                               23

<210> SEQ ID NO 26
<211> LENGTH: 21
<212> TYPE: DNA
<213> ORGANISM: Artificial Sequence
<220> FEATURE:
<223> OTHER INFORMATION: chemically synthesized oligonucleotide

<400> SEQUENCE: 26
acacactggc tgtacatgcg c                                                 21

<210> SEQ ID NO 27
<211> LENGTH: 19
<212> TYPE: DNA
<213> ORGANISM: Artificial Sequence
<220> FEATURE:
<223> OTHER INFORMATION: chemically synthesized oligonucleotide

<400> SEQUENCE: 27
acatgcgttt ggagactgc                                                    19

<210> SEQ ID NO 28
<211> LENGTH: 22
<212> TYPE: DNA
<213> ORGANISM: Artificial Sequence
<220> FEATURE:
<223> OTHER INFORMATION: chemically synthesized oligonucleotide

<400> SEQUENCE: 28
tggtcgacta gatcccctat ga                                                22

<210> SEQ ID NO 29
<211> LENGTH: 20
<212> TYPE: DNA
<213> ORGANISM: Artificial Sequence
<220> FEATURE:
<223> OTHER INFORMATION: chemically synthesized oligonucleotide

<400> SEQUENCE: 29
caaggcactg cagaggagta                                                   20

<210> SEQ ID NO 30
<211> LENGTH: 20
<212> TYPE: DNA
<213> ORGANISM: Artificial Sequence
<220> FEATURE:
<223> OTHER INFORMATION: chemically synthesized oligonucleotide
```

```
<400> SEQUENCE: 30
tgtccatctt gtcgtcttcg                                          20

<210> SEQ ID NO 31
<211> LENGTH: 21
<212> TYPE: DNA
<213> ORGANISM: Artificial Sequence
<220> FEATURE:
<223> OTHER INFORMATION: chemically synthesized oligonucleotide

<400> SEQUENCE: 31
gtcctggaag ccattgagcc a                                        21

<210> SEQ ID NO 32
<211> LENGTH: 21
<212> TYPE: DNA
<213> ORGANISM: Artificial Sequence
<220> FEATURE:
<223> OTHER INFORMATION: chemically synthesized oligonucleotide

<400> SEQUENCE: 32
ccagatggct gtcattcagt a                                        21

<210> SEQ ID NO 33
<211> LENGTH: 20
<212> TYPE: DNA
<213> ORGANISM: Artificial Sequence
<220> FEATURE:
<223> OTHER INFORMATION: chemically synthesized oligonucleotide

<400> SEQUENCE: 33
gaagaccttg cagcttccac                                          20

<210> SEQ ID NO 34
<211> LENGTH: 21
<212> TYPE: DNA
<213> ORGANISM: Artificial Sequence
<220> FEATURE:
<223> OTHER INFORMATION: chemically synthesized oligonucleotide

<400> SEQUENCE: 34
acacactaca cctggctcaa t                                        21

<210> SEQ ID NO 35
<211> LENGTH: 21
<212> TYPE: DNA
<213> ORGANISM: Artificial Sequence
<220> FEATURE:
<223> OTHER INFORMATION: chemically synthesized oligonucleotide

<400> SEQUENCE: 35
caggcagaag acatctgaaa g                                        21

<210> SEQ ID NO 36
<211> LENGTH: 19
<212> TYPE: DNA
<213> ORGANISM: Artificial Sequence
<220> FEATURE:
<223> OTHER INFORMATION: chemically synthesized oligonucleotide

<400> SEQUENCE: 36
gaaggtgaag gtcggagtc                                           19
```

```
<210> SEQ ID NO 37
<211> LENGTH: 20
<212> TYPE: DNA
<213> ORGANISM: Artificial Sequence
<220> FEATURE:
<223> OTHER INFORMATION: chemically synthesized oligonucleotide

<400> SEQUENCE: 37
gaagatggtg atgggatttc                                               20

<210> SEQ ID NO 38
<211> LENGTH: 21
<212> TYPE: DNA
<213> ORGANISM: Artificial Sequence
<220> FEATURE:
<223> OTHER INFORMATION: chemically synthesized oligonucleotide

<400> SEQUENCE: 38
ggtgaccaag ttcatgctgt g                                             21

<210> SEQ ID NO 39
<211> LENGTH: 20
<212> TYPE: DNA
<213> ORGANISM: Artificial Sequence
<220> FEATURE:
<223> OTHER INFORMATION: chemically synthesized oligonucleotide

<400> SEQUENCE: 39
gtgtccttga tccacttccg                                               20

<210> SEQ ID NO 40
<211> LENGTH: 20
<212> TYPE: DNA
<213> ORGANISM: Artificial Sequence
<220> FEATURE:
<223> OTHER INFORMATION: chemically synthesized oligonucleotide

<400> SEQUENCE: 40
cactgtgcat caccttgacc                                               20

<210> SEQ ID NO 41
<211> LENGTH: 20
<212> TYPE: DNA
<213> ORGANISM: Artificial Sequence
<220> FEATURE:
<223> OTHER INFORMATION: chemically synthesized oligonucleotide

<400> SEQUENCE: 41
acacgccatc acaccagtta                                               20

<210> SEQ ID NO 42
<211> LENGTH: 20
<212> TYPE: DNA
<213> ORGANISM: Artificial Sequence
<220> FEATURE:
<223> OTHER INFORMATION: chemically synthesized oligonucleotide

<400> SEQUENCE: 42
tccctcgaat gcaactctct                                               20

<210> SEQ ID NO 43
<211> LENGTH: 20
<212> TYPE: DNA
<213> ORGANISM: Artificial Sequence
<220> FEATURE:
<223> OTHER INFORMATION: chemically synthesized oligonucleotide
```

```
<400> SEQUENCE: 43
gccacatctc tgcagtcaaa                                               20

<210> SEQ ID NO 44
<211> LENGTH: 20
<212> TYPE: DNA
<213> ORGANISM: Artificial Sequence
<220> FEATURE:
<223> OTHER INFORMATION: chemically synthesized oligonucleotide

<400> SEQUENCE: 44
gcagaaggac aggacaaagc                                               20

<210> SEQ ID NO 45
<211> LENGTH: 20
<212> TYPE: DNA
<213> ORGANISM: Artificial Sequence
<220> FEATURE:
<223> OTHER INFORMATION: chemically synthesized oligonucleotide

<400> SEQUENCE: 45
caggctcttc ggtaaactcg                                               20

<210> SEQ ID NO 46
<211> LENGTH: 24
<212> TYPE: DNA
<213> ORGANISM: Artificial Sequence
<220> FEATURE:
<223> OTHER INFORMATION: chemically synthesized oligonucleotide

<400> SEQUENCE: 46
atgttcacat tagtacacct tgcc                                          24

<210> SEQ ID NO 47
<211> LENGTH: 26
<212> TYPE: DNA
<213> ORGANISM: Artificial Sequence
<220> FEATURE:
<223> OTHER INFORMATION: chemically synthesized oligonucleotide

<400> SEQUENCE: 47
tctcagatcc aggcttgctt actgtc                                        26

<210> SEQ ID NO 48
<211> LENGTH: 22
<212> TYPE: DNA
<213> ORGANISM: Artificial Sequence
<220> FEATURE:
<223> OTHER INFORMATION: chemically synthesized oligonucleotide

<400> SEQUENCE: 48 cccccctattt taatcggagt ac                                           22

<210> SEQ ID NO 49
<211> LENGTH: 22
<212> TYPE: DNA
<213> ORGANISM: Artificial Sequence
<220> FEATURE:
<223> OTHER INFORMATION: chemically synthesized oligonucleotide

<400> SEQUENCE: 49
ttttgaagag cacagaacac ct                                            22
```

```
<210> SEQ ID NO 50
<211> LENGTH: 20
<212> TYPE: DNA
<213> ORGANISM: Artificial Sequence
<220> FEATURE:
<223> OTHER INFORMATION: chemically synthesized oligonucleotide

<400> SEQUENCE: 50
attaaccctc actaaaggga                                           20

<210> SEQ ID NO 51
<211> LENGTH: 16
<212> TYPE: DNA
<213> ORGANISM: Artificial Sequence
<220> FEATURE:
<223> OTHER INFORMATION: chemically synthesized oligonucleotide

<400> SEQUENCE: 51
gtaaaacgac ggccag                                               16

<210> SEQ ID NO 52
<211> LENGTH: 21
<212> TYPE: DNA
<213> ORGANISM: Artificial Sequence
<220> FEATURE:
<223> OTHER INFORMATION: chemically synthesized oligonucleotide

<400> SEQUENCE: 52
ccagatggct gtcattcagt a                                         21

<210> SEQ ID NO 53
<211> LENGTH: 21
<212> TYPE: DNA
<213> ORGANISM: Artificial Sequence
<220> FEATURE:
<223> OTHER INFORMATION: chemically synthesized oligonucleotide

<400> SEQUENCE: 53
aagtagagca tcctggagtt g                                         21
```

ANDROGEN RECEPTOR VARIANTS AND METHODS FOR MAKING AND USING

CROSS-REFERENCE TO RELATED APPLICATIONS

This application is a United States national phase application under 35 U.S.C. § 371 of International PCT application PCT/US2013/066982, filed Oct. 25, 2013, which claims the benefit of and priority to U.S. provisional application Ser. No. 61/719,105, filed Oct. 26, 2012, the entirety of which is incorporated herein by reference.

Government Support

This invention was made with government support under CA155169 and CA089489 awarded by The National Cancer Institute; R25-CA096945 awarded by the National Institutes of Health; and PC102106 awarded by the Department of Defense. The government has certain rights in the invention.

BACKGROUND

It is believed that one-third of all people in the United States will develop cancer. Although remarkable progress has been made in understanding the biological basis of and in treating cancer, cancer remains second only to cardiac disease as the main cause of death in the United States.

Prostate cancer is the most common form of cancer in males. It typically afflicts aging males, but it can afflict males of all ages. A significant number of males die from prostate cancer every year, and it is the second leading cause of cancer deaths in men.

SUMMARY

The present invention encompasses the recognition that reproducible and detectable changes in the Androgen Receptor (AR) polypeptide sequence are associated with incidence and/or risk of Castration Resistant Prostate Cancer (CRPC), specifically in individuals having prostate cancer and on antiandrogen therapy. The present invention provides novel AR polypeptide sequences associated with increased incidence and/or risk of CRPC. The present invention also provides technologies for identification and/or characterization of novel AR polypeptide sequences associated with increased incidence and/or risk of CRPC. The present invention also provides technologies for identification and/or characterization of agents to treat and/or reduce risk of CRPC; in some embodiments such agents alter level and/or activity of an AR. In some embodiments, provided agents alter level and/or activity of an AR whose polypeptide sequence is associated with increased incidence and/or risk of CRPC. In some embodiments, provided agents show effects on an AR's activity of regulating transcription of one or more target genes. The present invention also provides systems for using such agents, for example to treat and/or reduce risk of CRPC.

In certain embodiments, the present disclosure provides methods of providing a sample from an individual whose risk or incidence of castration resistant prostate cancer is to be identified or characterized, processing the sample to detect a sequence of an androgen receptor or portion thereof; and classifying the individual as having an elevated risk or incidence of castration resistant prostate cancer if the determined sequence encodes an androgen receptor polypeptide or portion thereof having a sequence containing a mutation relative to a reference androgen receptor polypeptide, which mutation correlates with incidence of castration resistant prostate cancer. In some embodiments, the step of processing comprises processing to detect a sequence of an androgen receptor gene or fragment thereof. In some embodiments, the mutation that correlates with incidence of castration resistant prostate cancer is selected from F876C, F876I, F876L, F876S, F876V, F876Y, C686Y, A699T, N771S, H776Y, C784R, K910E, E565K, E588K, and E668K. In some embodiments, the mutation that correlates with incidence of castration resistant prostate cancer is selected from F876C, F876I, F876L, F876S, F876V, and F876Y.

In certain embodiments, the present disclosure provides methods of treating castration resistant prostate cancer comprising the steps of providing a sample from a prostate cancer patient being treated with an antiandrogen whose risk or incidence of castration resistant prostate cancer is to be identified or characterized, processing the sample to detect a sequence of an androgen receptor or portion thereof, classifying the individual as having an elevated risk or incidence of castration resistant prostate cancer if the determined sequence encodes an androgen receptor peptide or portion thereof having a sequence containing a mutation relative to a reference androgen receptor polypeptide, which mutation correlates with incidence of castration resistant prostate cancer, and revising the treatment if the a prostate cancer patient is found to have the elevated risk or incidence of castration resistant prostate cancer according to the methods described herein. In some embodiments, revising the treatment comprises discontinuing treatment with antiandrogens. In some embodiments, revising the treatment further comprises administering treatments for castration resistant prostate cancer. In some embodiments, the method reduces severity of prostate cancer symptoms.

In certain embodiments, the present disclosure provides methods for identifying antiandrogen resistant androgen receptor mutants comprising providing a population of cells comprising a library of androgen receptor polypeptides each of which shares at least 95% overall sequence identity with a single parent androgen receptor polypeptide and a reporter, contacting the population of cells with an antiandrogen, detecting expression of the reporter, classifying cells as antiandrogen resistant androgen receptor mutants if expression of the reporter is increased. In some embodiments, members of the library are related to one another in that each is expressed by a gene found in a mutagenized preparation of the gene encoding the single parent androgen receptor polypeptide. In some embodiments, the androgen receptor-activated reporter comprises an androgen receptor-activated promoter fused to a coding sequence for a fluorescent protein. In some embodiments, detecting cells comprises flow cytometry analysis.

In certain embodiments, the present disclosure provides methods for identifying antiandrogen resistant androgen receptor mutants comprising contacting a population of cells with an antiandrogen until an increase in growth rate occurs, classifying cells as antiandrogen resistant androgen receptor mutants once an increase in growth rate occurs, and processing the cells to detect a sequence of an androgen receptor or portion thereof. In some embodiments, the population of cells is contacted with an antiandrogen in vitro. In some embodiments, the population of cells is contacted with an antiandrogen in vivo.

In certain embodiments, the present disclosure provides methods for identifying compounds for treating or reducing the risk of castration resistant prostate cancer comprising providing a population of cells comprising an androgen receptor polypeptide containing a mutation that correlates with incidence of castration resistant prostate cancer and an androgen receptor-activated reporter, contacting the population of cells with one or more agents, detecting expression of the androgen receptor-activated reporter, and classifying test agents as treating or reducing the risk of castration resistant prostate cancer if expression of the androgen receptor-activated reporter is decreased. In some embodiments, the one or more agents comprises a chemical library.

In certain embodiments, the present disclosure provides methods for treating or reducing the risk of castration resistant prostate cancer comprising administering to a subject one or more agents characterized in that transcription levels of one or more targets of androgen receptor-activated transcriptional activation are lower in the agent's presence as compared with in its absence.

In certain embodiments, the present disclosure provides isolated polypeptides whose amino acid sequence shows at least 80% overall sequence identity with a reference wild type androgen receptor polypeptide of SEQ ID NO: 1 and fragments thereof that are at least 10 amino acids in length, which polypeptide includes a residue corresponding to residue 876, which corresponding residue is not leucine. In some embodiments, the phenylalanine at amino acid 876 is substituted with an amino acid selected from cysteine, isoleucine, leucine, serine, tyrosine or valine. In some embodiments, the phenylalanine at amino acid 876 is substituted with leucine.

In certain embodiments, the present disclosure provides isolated polypeptides whose amino acid sequence shows at least 80% overall sequence identity with a reference wild type androgen receptor polypeptide of SEQ ID NO: 1 and fragments thereof that are at least 10 amino acids in length, which polypeptide includes a mutation selected from E565K, E588K, S647G, E668K, C686Y, D695E, A699T, R726H, N727I, N771S, H776Y, C784R, and/or K910E.

In certain embodiments, the present disclosure provides antibodies that bind to an androgen receptor polypeptide whose amino acid sequence shows at least 70% overall sequence identity with a reference wild type androgen receptor polypeptide of SEQ ID NO: 1, which polypeptide includes a residue corresponding to residue 876, which corresponding residue is not leucine but does not bind to an androgen receptor polypeptide whose amino acid sequence shows at least 70% overall sequence identity with a reference wild type androgen receptor polypeptide of SEQ ID NO: 1, which polypeptide includes a residue corresponding to residue 876, which corresponding residue is leucine. In some embodiments, the phenylalanine at amino acid 876 is substituted with an amino acid selected cysteine, isoleucine, leucine, serine, tyrosine or valine. In some embodiments, the phenylalanine at amino acid 876 is substituted with leucine.

In certain embodiments, the present disclosure provides antibodies that bind to an androgen receptor polypeptide whose amino acid sequence shows at least 70% overall sequence identity with a reference wild type androgen receptor polypeptide of SEQ ID NO: 1, which polypeptide includes a mutation selected from E565K, E588K, S647G, E668K, C686Y, D695E, A699T, R726H, N727I, N771S, H776Y, C784R, and/or K910E but does not bind to an androgen receptor polypeptide whose amino acid sequence shows at least 70% overall sequence identity with a reference wild type androgen receptor polypeptide of SEQ ID NO: 1, which polypeptide includes a residue corresponding to the wild type amino acid at the selected mutation site.

In certain embodiments, the present disclosure provides siRNA or antisense oligonucleotides that are specifically hybridizable to an mRNA encoding an androgen receptor polypeptide whose amino acid sequence shows at least 70% overall sequence identity with a reference wild type androgen receptor polypeptide of SEQ ID NO: 1, which polypeptide includes a residue corresponding to residue 876, which corresponding residue is not leucine but is not specifically hybridizable to an mRNA encoding to an androgen receptor polypeptide whose amino acid sequence shows at least 70% overall sequence identity with a reference wild type androgen receptor polypeptide of SEQ ID NO: 1, which polypeptide includes a residue corresponding to residue 876, which corresponding residue is leucine. In some embodiments, the phenylalanine at amino acid 876 is substituted with an amino acid selected from cysteine, isoleucine, leucine, serine, tyrosine or valine. In some embodiments, the phenylalanine at amino acid 876 is substituted with leucine.

In certain embodiments, the present disclosure provides siRNA or antisense oligonucleotides that are specifically hybridizable to an mRNA encoding an androgen receptor polypeptide whose amino acid sequence shows at least 70% overall sequence identity with a reference wild type androgen receptor polypeptide of SEQ ID NO: 1, which polypeptide includes a mutation selected from E565K, E588K, S647G, E668K, C686Y, D695E, A699T, R726H, N727I, N771S, H776Y, C784R, and/or K910E but is not specifically hybridizable to an mRNA encoding to an androgen receptor polypeptide whose amino acid sequence shows at least 70% overall sequence identity with a reference wild type androgen receptor polypeptide of SEQ ID NO: 1, which polypeptide includes a residue corresponding to the wild type amino acid at the selected mutation site.

In certain embodiments, the present disclosure provides methods for identifying and/or characterizing compounds for treating or reducing the risk of castration resistant prostate cancer comprising the steps of administering a composition comprising an agent to a system that includes tumor cells and assessing a response of the system to the administration. In some embodiments, detecting the response of the system comprises detecting a level of androgen receptor activity. In some embodiments, detecting the response of the system comprises assessing the response of the system comprises detecting a change in tumor size. In some embodiments, agents comprise agents that inhibit androgen receptor mutant activity. In some embodiments, androgen receptor mutants are selected from F876C, F876I, F876L, F876S, F876V, F876Y, E565K, E588K, S647G, E668K, C686Y, D695E, A699T, R726H, N727I, N771S, H776Y, C784R, and/or K910E. In some embodiments, androgen receptor mutants are selected from F876C, F876I, F876L, F876S, F876V, and F876Y.

BRIEF DESCRIPTION OF THE DRAWING

FIG. 5 shows a table of enrichment of F876 mutant expressing cells after enzalutamide or ARN-509 exposure.

Genomic DNA was isolated from the sorted cell populations, and qPCR was performed to test for enrichment of the W741C mutant cells.

Figure 7:
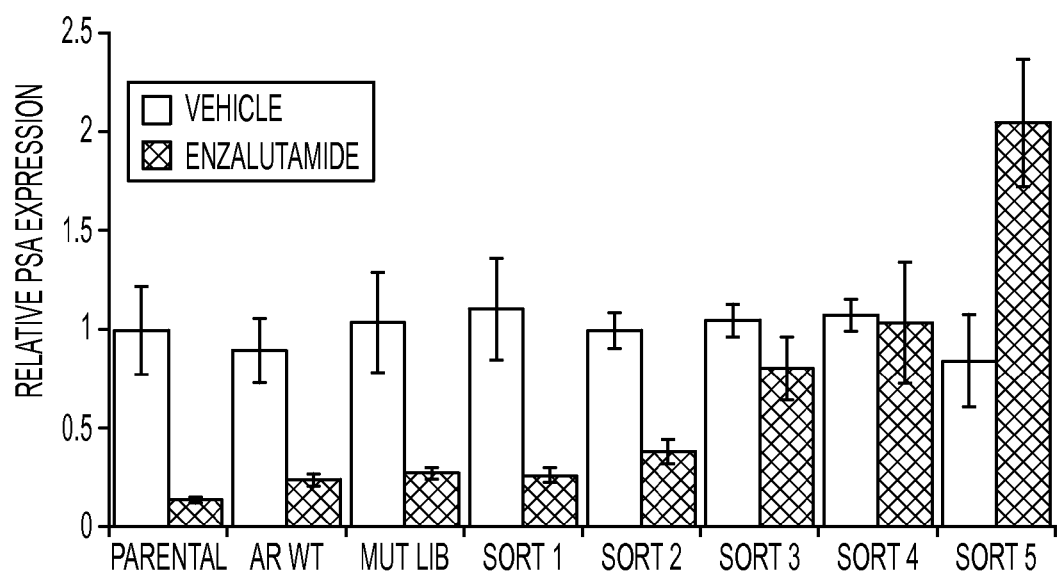

FIG. 7 shows that Endogenous AR target gene PSA is induced by enzalutamide in FACS-sorted cells. Parental LNCaP-Pb.PSE.EGFP cells, and those overexpressing AR WT, the random AR mutant library (Mut Lib), and cells after each sort were treated with 1 uM enzalutamide for 24 hours in media containing full serum. RNA was then collected, reverse transcribed, and quantitative PCR performed for AR target gene KLK3 (PSA).

FIGS. 8A-8B show expression of EGFP and endogenous AR target gene FKBP5 remains AR-dependent in FACS-sorted cells. LNCaP-Pb.PSE.EGFP cells overexpressing AR WT and cells from the fifth sort of our screen were transfected with either a non-targeting siRNA (siNT) or a siRNA against AR (siAR). They were also treated with either vehicle (V) or 1 µM enzalutamide (E). After four days of enzalutamide treatment and siRNA knockdown, cells were collected for both (A) flow cytometric analysis of EGFP expression and (B) western blot analysis of the AR target gene FKBP5, and to ensure we achieved good AR knockdown.

Figure 9:
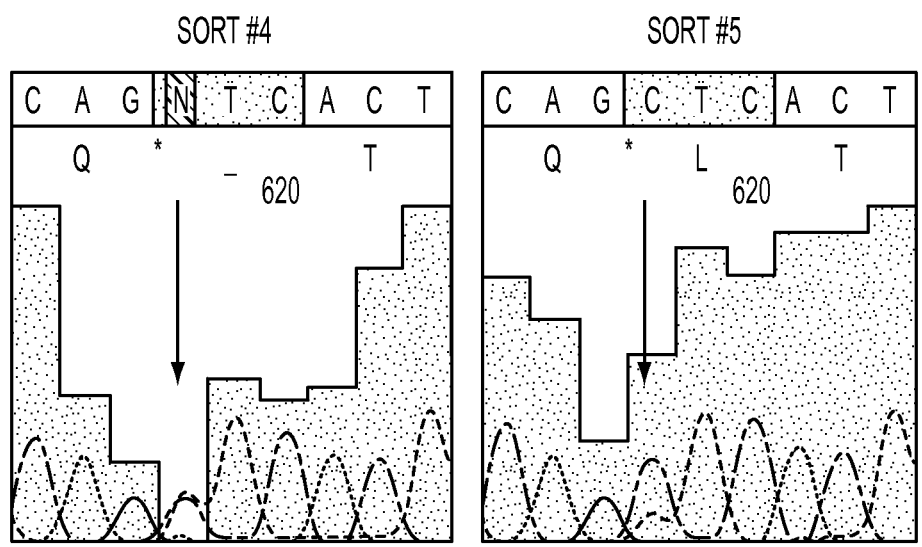

FIG. 9 shows AR F876L mutation accounts for 50% of AR in cells after $4^{th}$ sort, but further enriched after the fifth sort. AR from the mutant library LNCaP-Pb.PSE.EGFP cells was PCR amplified after four rounds of enzalutamide treatment and FACS-sorting, and Sanger sequenced the PCR product. AR F876L (T C) accounts for approximately 50% of the AR in these cells. This mutation is further enriched after the $5^{th}$ sort, and accounts for approximately 80% of AR in that population of cells.

Figure 10:
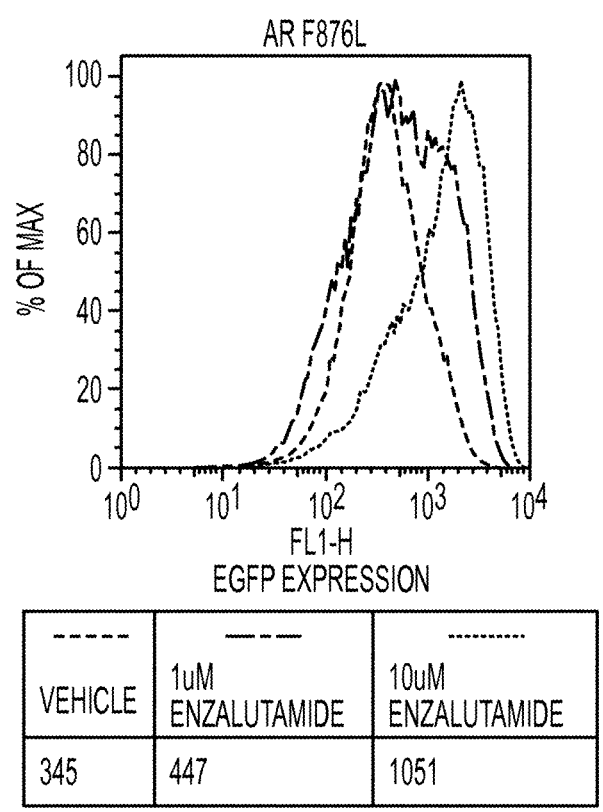

FIG. 10 shows dose-dependent induction of EGFP expression by enzalutamide in LNCaP-Pb.PSE.EGFP cells expressing AR F876L. LNCaP-Pb.PSE.EGFP cells ectopically expressing AR F876L were treated with vehicle, 1 µM enzalutamide, or 10 µM enzalutamide for 4 days. Cells were then collected for FACS-analysis of EGFP expression. Geometric-mean fluorescence intensity is indicated in the table.

FIGS. 11A-11B show enzalutamide induces AR F876L nuclear translocation and DNA binding to AR enhancer elements. (A) LNCaP cells were transfected with EYFP tagged wild-type AR or AR F876L in androgen depleted media containing vehicle, 1 µM enzalutamide, or 1 nM DHT. Representative confocal images are shown. Average nuclear-to-cytoplasmic ratios for EYFP are displayed (±SD, n=3). (B) LNCaP cells stably overexpressing either AR WT or AR F876L were cultured in androgen-depleted media for 4 days, then treated with vehicle, 10 µM enzalutamide, or 1 nM DHT for 4 hours. AR chromatin immuoprecipitation was performed, and real-time PCR quantification of PSA enhancer and FKBP5 enhancer is shown (percent input mean±SD, n=3).

Figure 12:
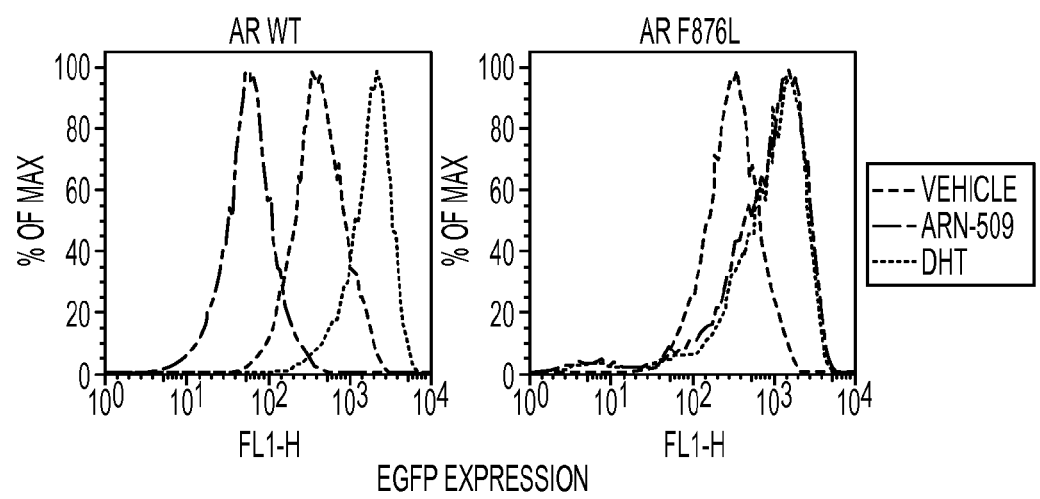

FIG. 12 shows AR F876L mutation also converts ARN-509 into an AR agonist. LNCaP-Pb.PSE.EGFP cells ectopically expressing either AR WT or AR F876L were treated with vehicle, 10 µM ARN-509, or 1 nM DHT. After four days of treatment, cells were collected for analysis of EGFP expression (FL1-H). Geometric mean fluorescence intensity (MFI) for WT treated cells: vehicle (398), ARN-509 (51.7), DHT (1641); for F876L cells: vehicle (322), ARN-509 (986), DHT (1215).

FIGS. 13A-13B show ectopic expression of AR F876L in CWR22PC cells confers resistance to enzalutamide and rescues growth in androgen-depleted media. (A) CWR22PC cells stably expressing either AR WT or AR F876L were plated in full serum media containing vehicle, 1 µM enzalutamide, or 10 µM bicalutamide. CellTiterGLO assay was performed on days 1, 4, and 7 to measure cell viability. (B) CWR22PC cells stably expressing either AR WT or AR F876L were plated in full serum media containing vehicle, 1 µM enzalutamide, or 0.1 nM DHT. CellTiterGLO assay was performed on days 1, 4, and 7 to measure cell viability.

FIGS. 14A-14B show other amino acid substitutions at Phe876 modify the pharmacology of second generation antiandrogens. (A) ARE(4X)-luciferase assay for additional F876 substitutions. CV1 cells were cotransfected with an ARE(4X)-firefly luciferase construct, SV40 Renilla luciferase construct and one of the designated AR constructs. The cells were then treated with 10 µM of the indicated antiandrogens and a dual luciferase assay was performed on the lysates (normalized to Renilla luciferase). (B) EGFP reporter assay for additional F876 substitutions. LNCaP-Pb.PSE.EGFP cells transduced with the indicated AR F876 substitutions were treated with 10 uM of antiandrogens or 1 nM DHT and subjected to flow cytometry analysis of EGFP expression. The table provides geometric-mean fluorescence intensity (MFI) calculations.

FIGS. 15A-15C show an EGFP reporter assay for AR activity with DR series compounds. LNCaP-Pb.PSE.EGFP cells ectopically expressing either AR WT or AR F876L were treated with vehicle (DMSO) or 10 µM of the indicated DR-series compound. After 4 days of treatment, cells were collected and FACS analysis for EGFP expression was performed. Geometric-mean fluorescence intensity is indicated in the adjacent table.

Figure 16:
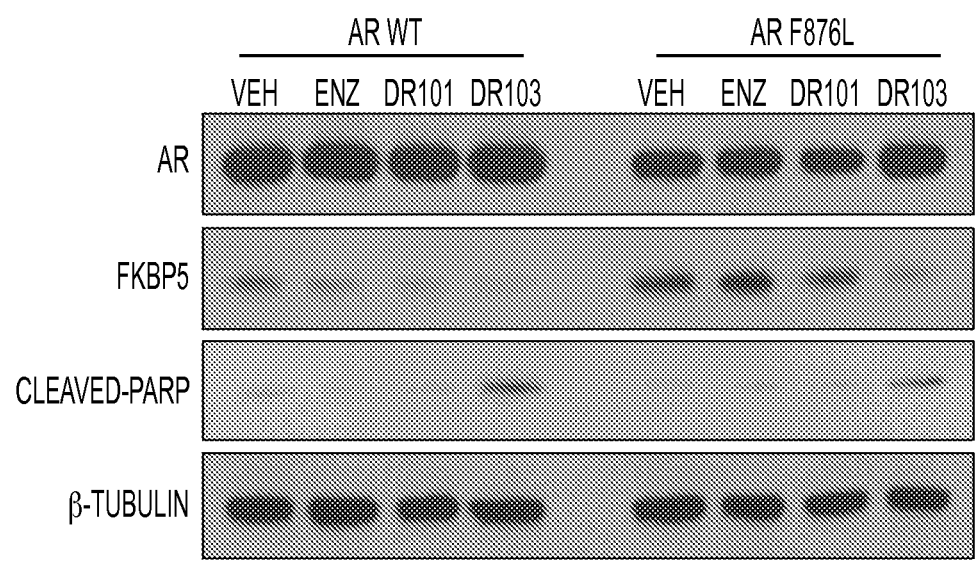

FIG. 16 shows a novel antiandrogen, DR103, efficiently inhibits AR signaling and induces PARP cleavage in cells expressing both AR WT and AR F876L. VCaP cells were treated for 4 days with vehicle or 10 µM of the indicated antiandrogen (ENZ=enzalutamide) in media containing FBS. Whole-cell lysates were analyzed by Western blot.

Figure 17:
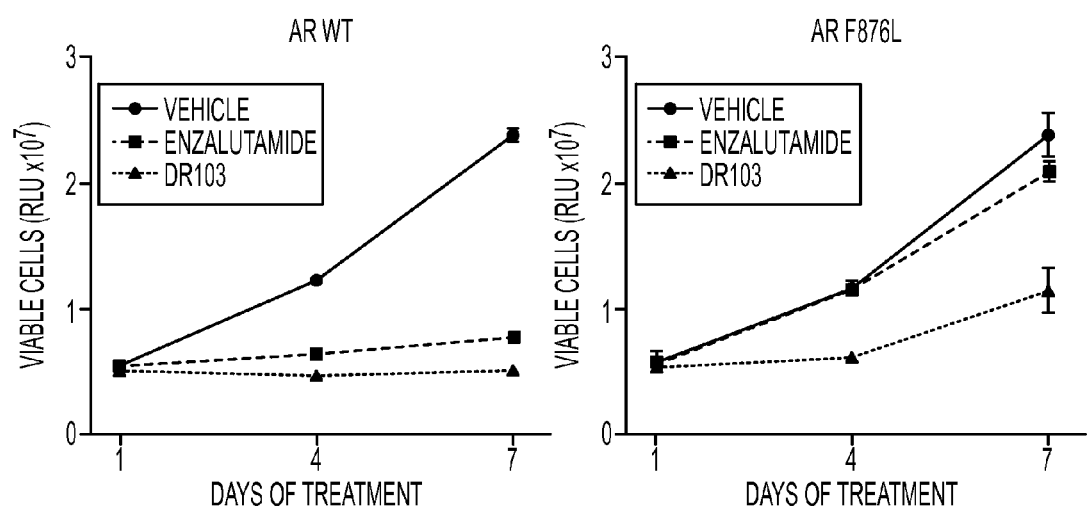

FIG. 17 shows growth inhibition of CWR22PC cells overexpressing AR WT or AR F876L with DR103 treatment. CWR22PC cells ectopically expressing wild-type AR or AR F876L, cultured in full-serum containing media, were treated with vehicle (DMSO) or 10 µM of enzalutamide or DR103. CellTiterGLO assay was performed on days 1, 4, and 7 to determine cell viability. RLU=relative light units.

Figure 18:
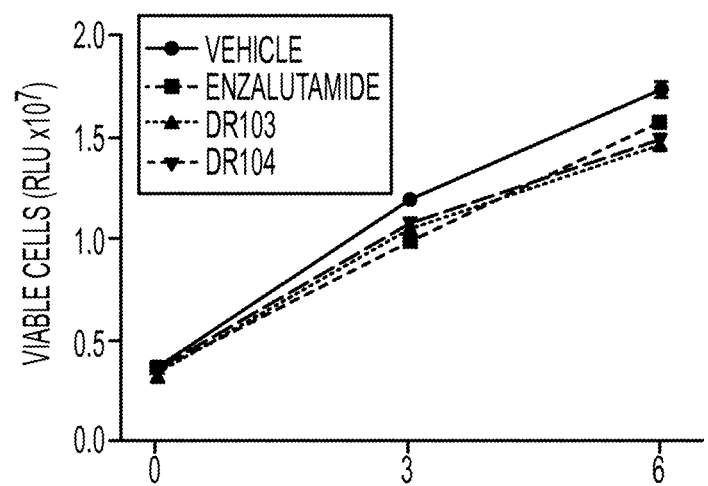

FIG. 18 shows that U145 cells treated with DR103 and DR104 display no significant growth inhibition. DU145 cells were cultured in full serum containing media with 10 uM of the indicated antiandrogens. CellTiterGLO assay was performed on days 0, 3, and 6 to determine cell viability. RLU=relative light units.

Figure 19:
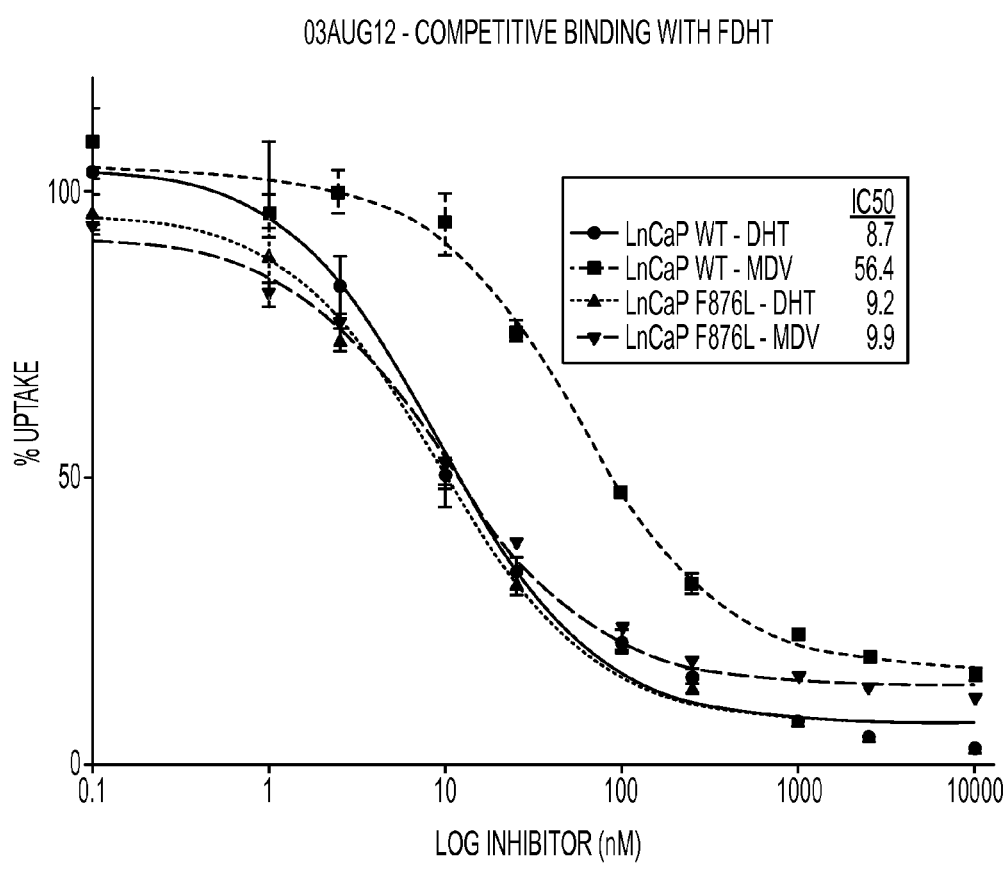

FIG. 19 shows the relative binding affinity of DHT and MDV3100 in LNCaP cells ectopically expressing AR WT or AR F876L.

Figure 20:
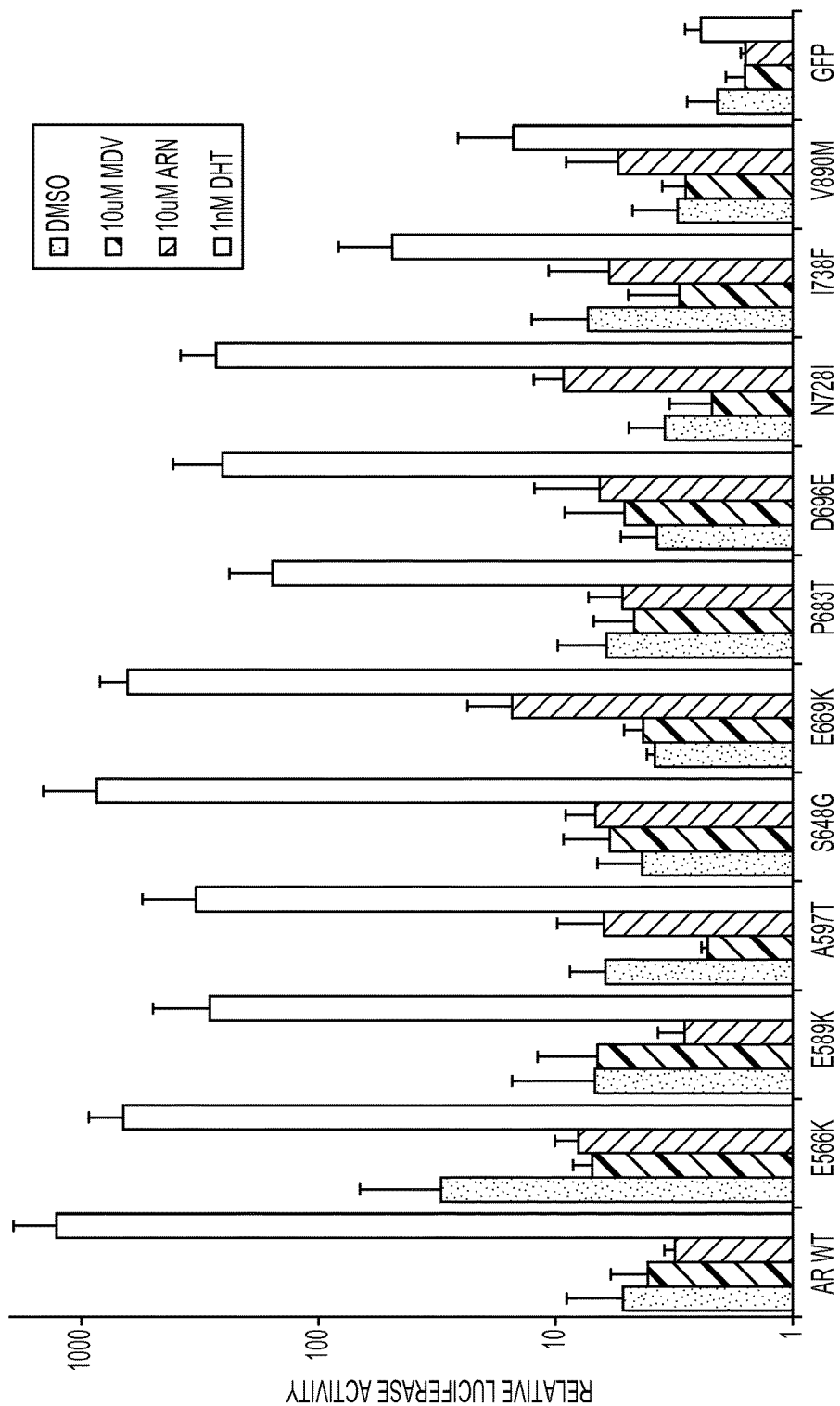

FIG. 20 shows a luciferase reporter assay of AR activity in androgen depleted media. None of the mutants conferred agonism on either MDV3100 (enzalutamide) or ARN-509.

Figure 21A:
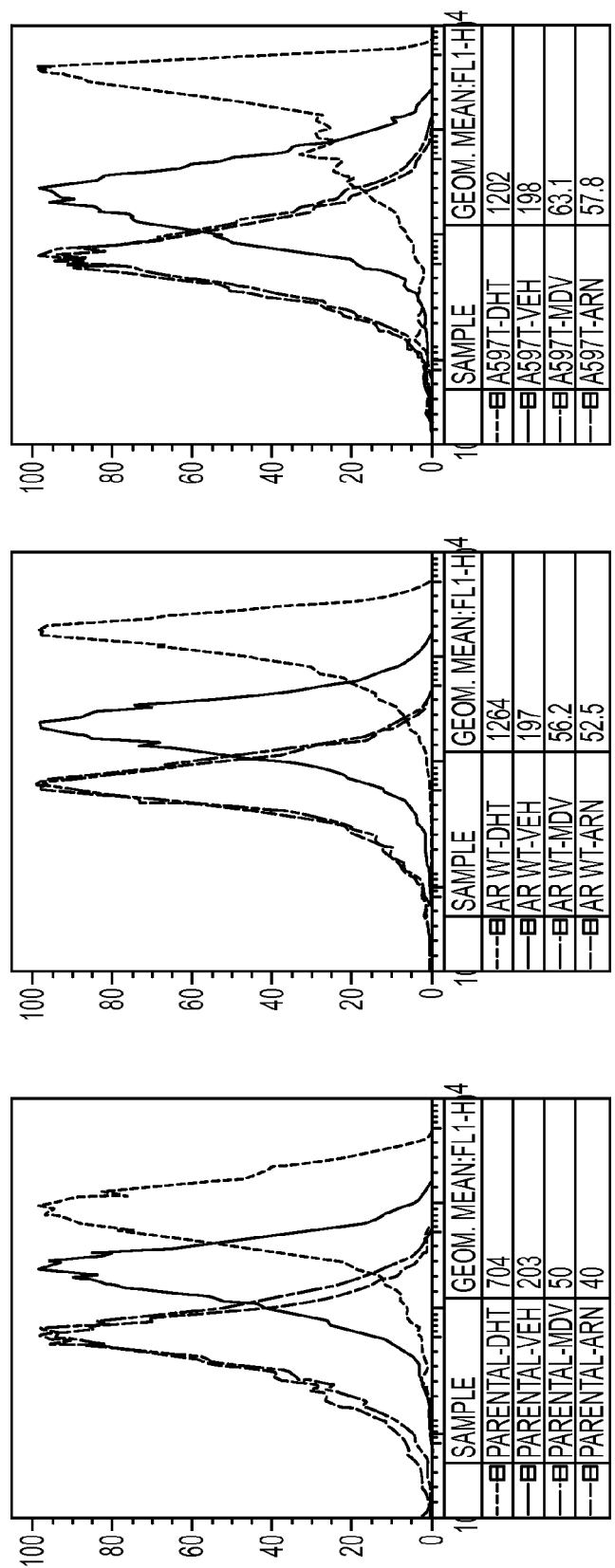
Figure 21A:
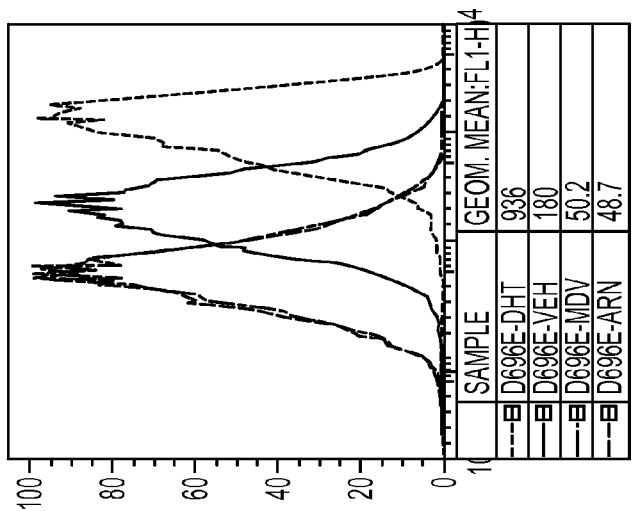
Figure 21A:
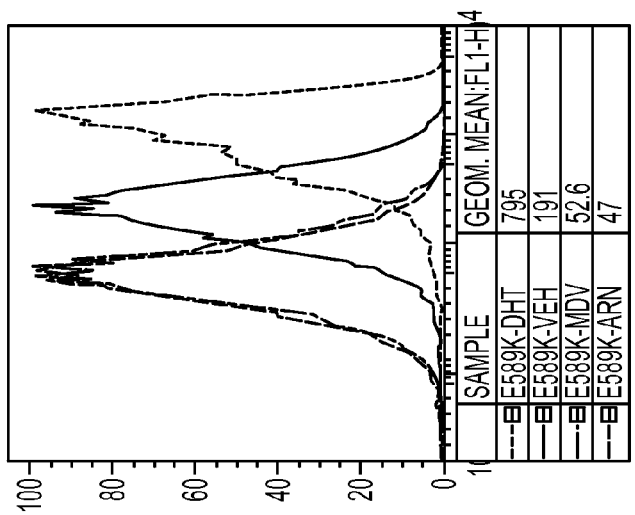
Figure 21A:
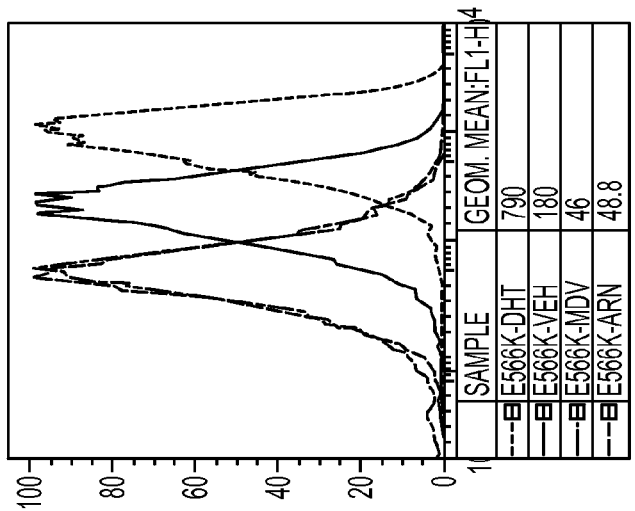
Figure 21B:
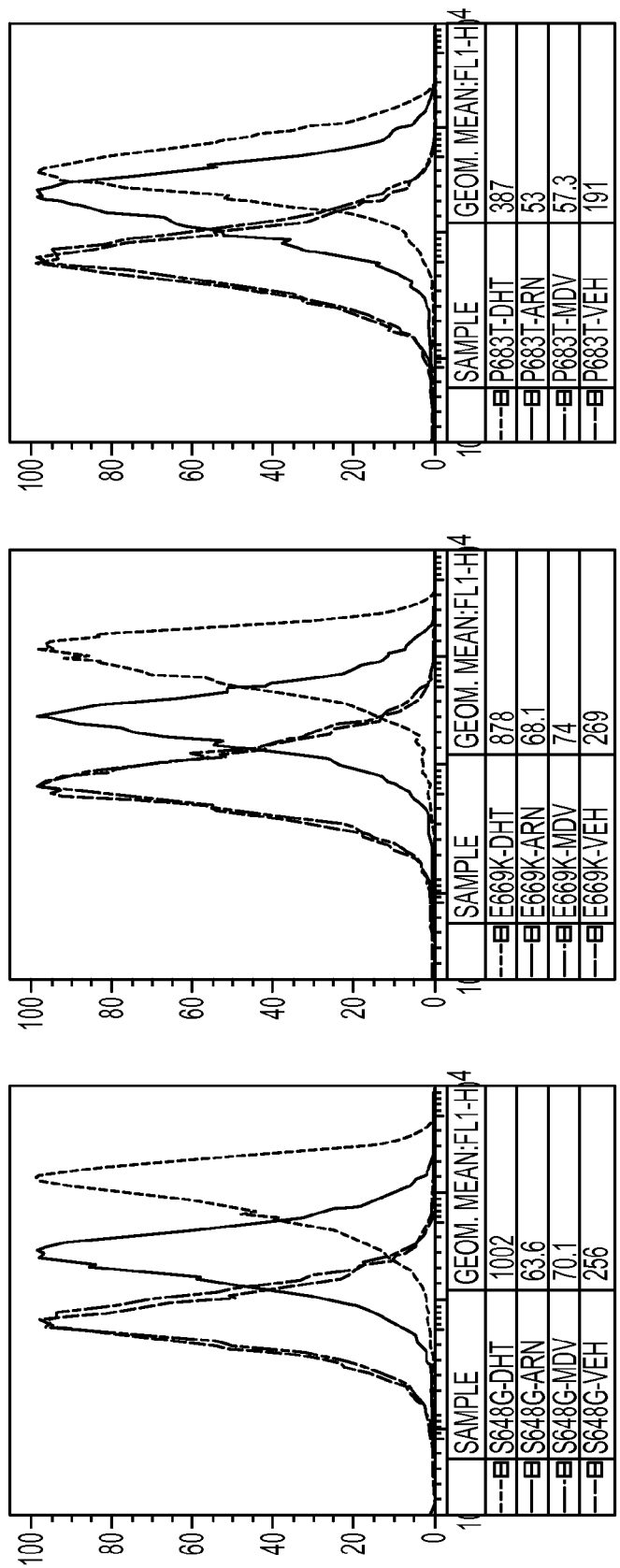
Figure 21B:
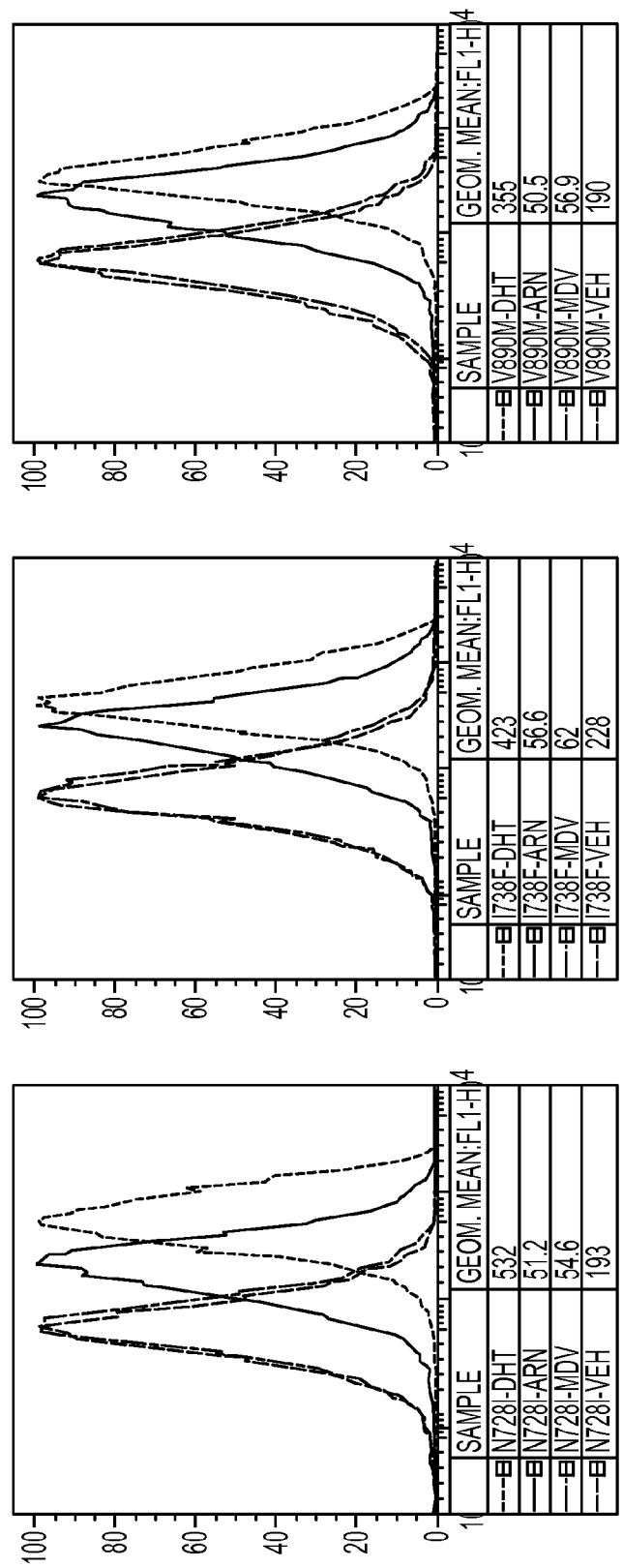

FIGS. 21A-21B show data from EGFP reporter assays of AR activity in cells expressing the indicated AR mutants. All of the mutants remained sensitive to enzalutamide and ARN-509.

Figure 22:
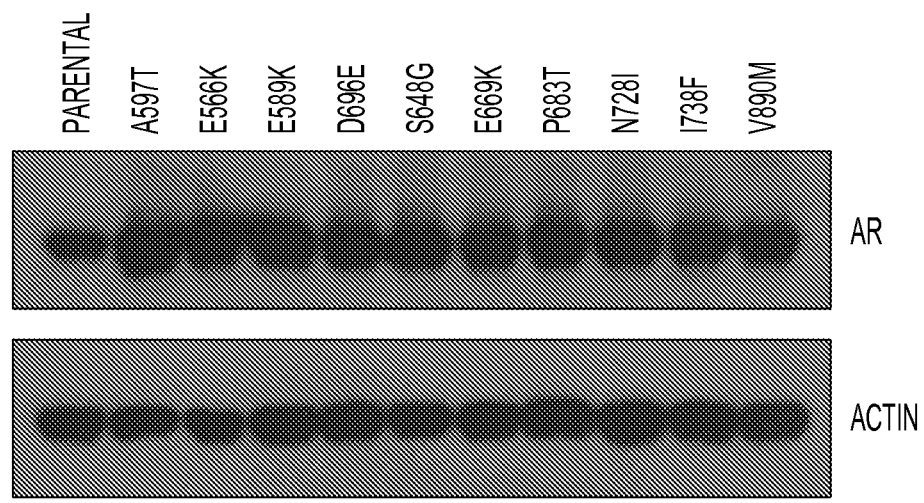

FIG. 22 shows Western blots of LNCaP/Pb.PSE.EGFP cells expressing the indicated AR mutants were cultured in media containing FBS. These data indicate that all of the mutants were expressed at comparable levels in LNCaP/Pb.PSE.EGFP cells. Also, these results indicate that compared to wild-type, some of these mutants altered the responsiveness of the receptor to DHT.

Figure 23:
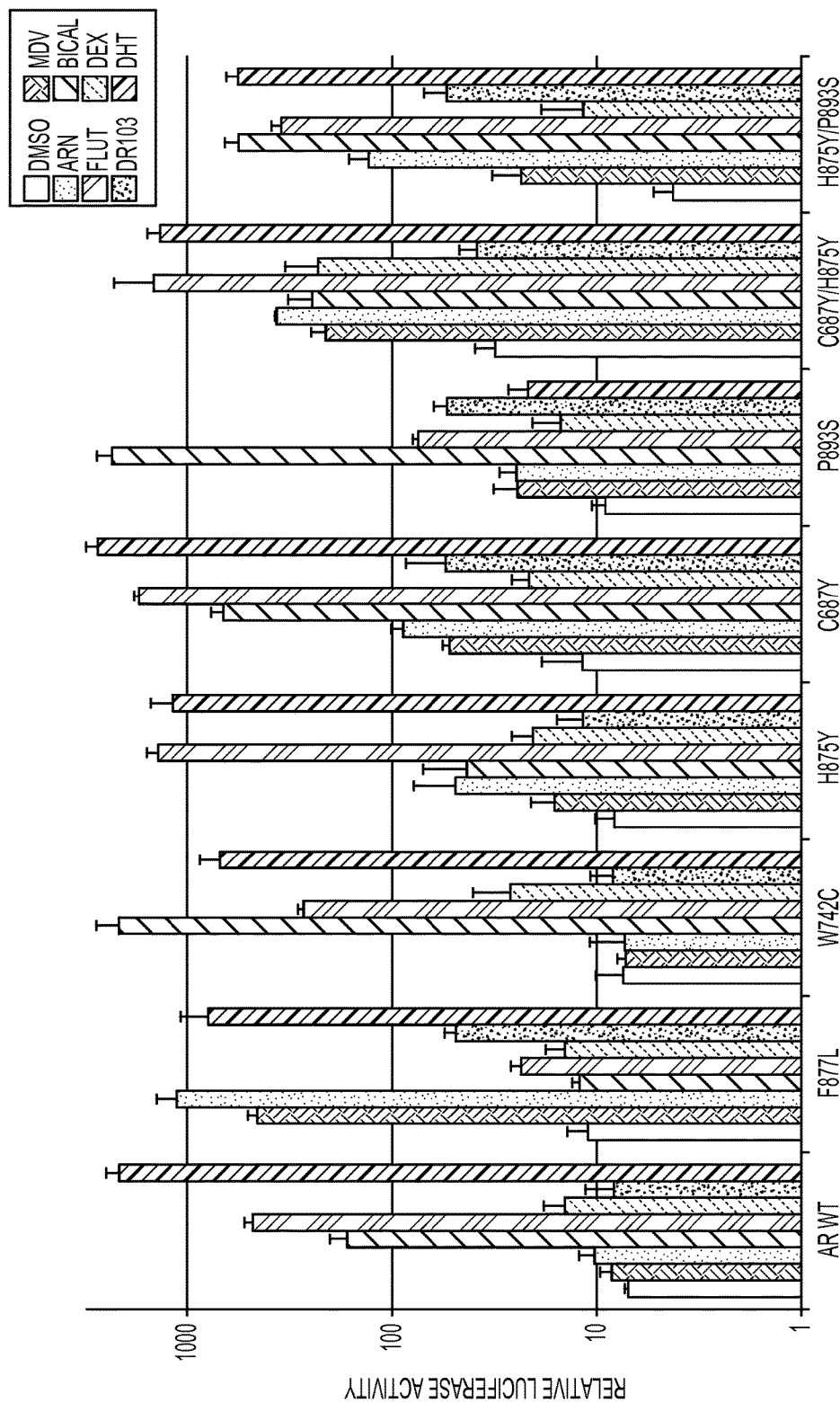

FIG. 23 shows a luciferase reporter of AR activity in androgen depleted media. These data indicate that P893S conferred agonism on Bicalutamide, comparable to the previously described W742C mutant; this P893S mutant also lost DHT responsiveness.

Figure 24:
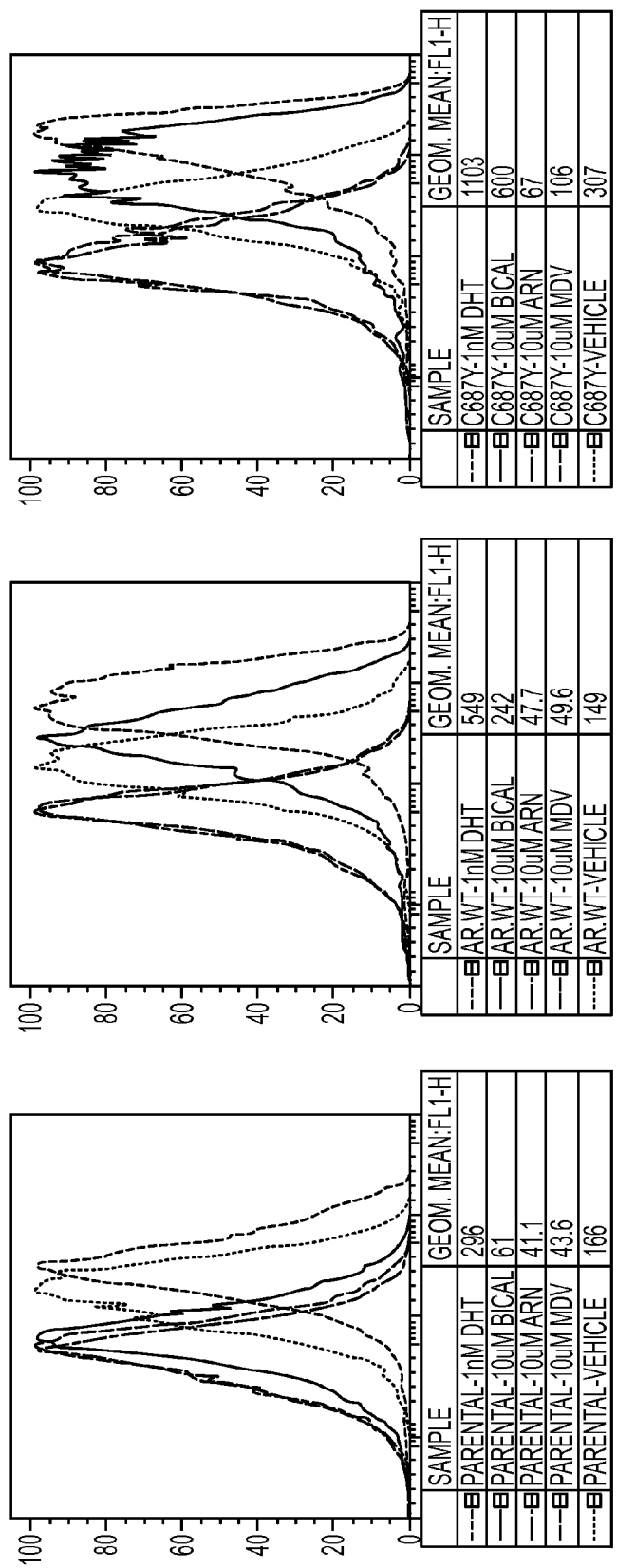
Figure 24:
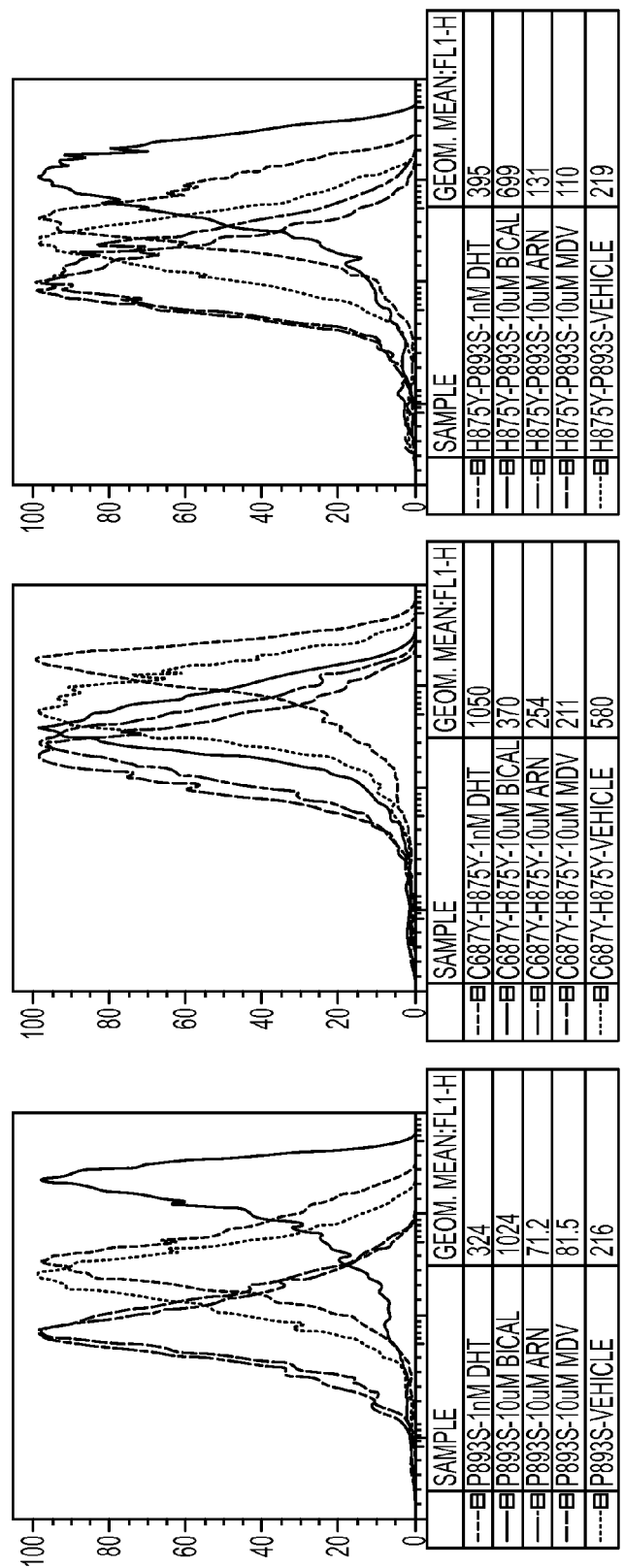

FIG. 24 shows data from LNCaP/Pb.PSE.EGFP cells that were cultured in androgen containing media and treated with either vehicle (Veh), 10 μM antiandrogen or 1 nM DHT. These data also suggest that all of these mutants still remained sensitive to enzalutamide and ARN-509, although to variable degrees and with gene-specific differences.

Figure 25:
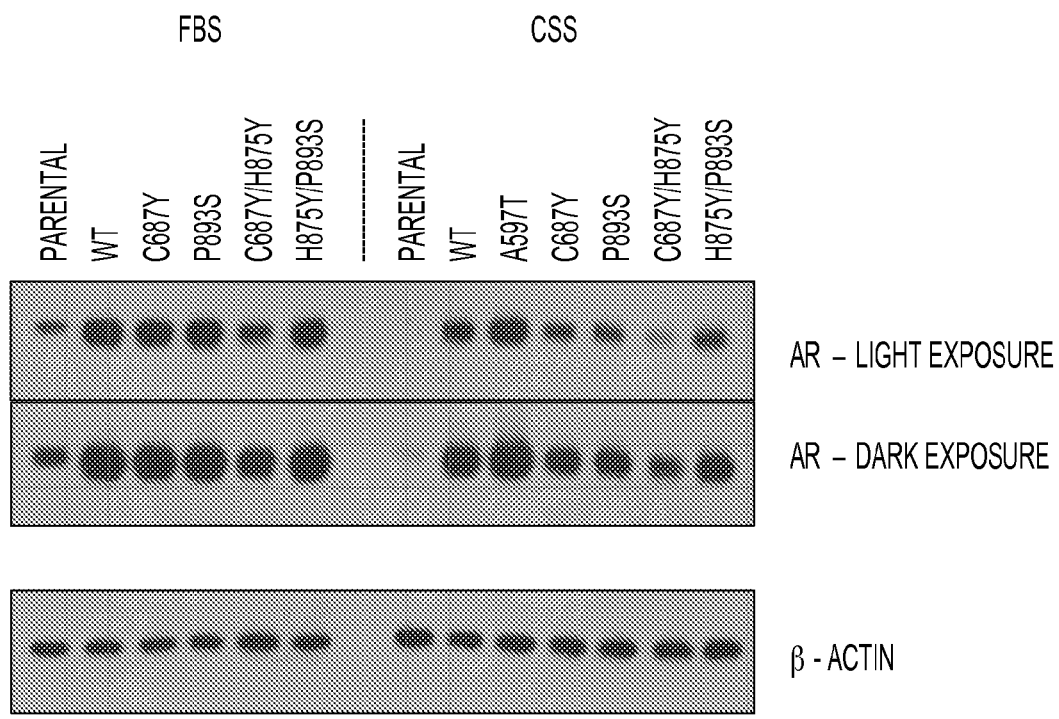

FIG. 25 shows Western blots of LNCaP/Pb.PSE.EGFP cells expressing the indicated AR mutants that were cultured in media containing either FBS or CSS. These mutants were not expressed at comparable levels in LNCaP/Pb.PSE.EGFP cells; in particular C687Y and C687Y/H875Y were expressed at lower levels.

Figure 26:
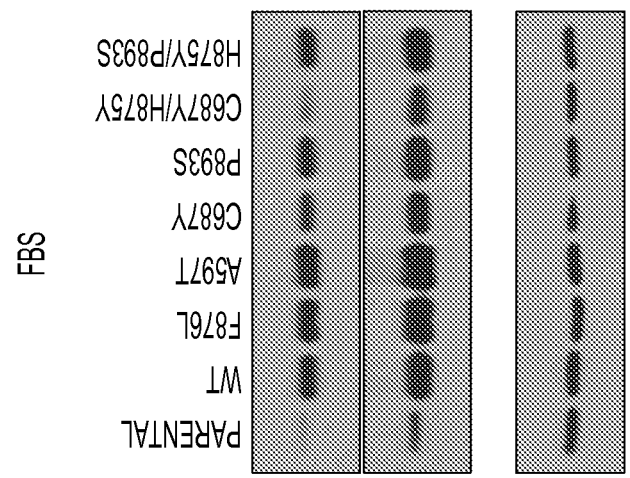
Figure 26:
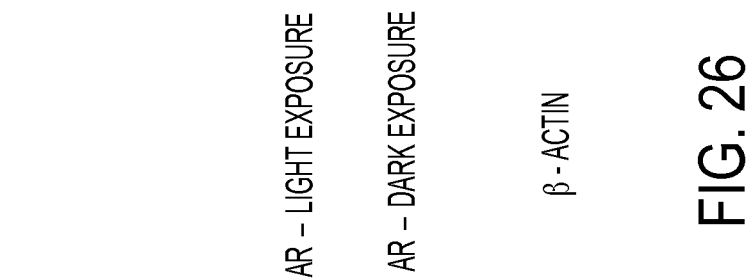
Figure 26:
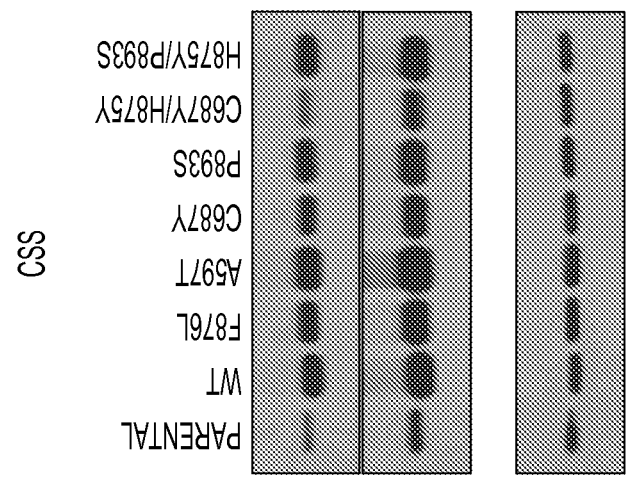

FIG. 26 shows Western blots of CWR22Pc cells expressing the indicated AR mutants that were cultured in media containing either FBS or CSS. These mutants were not expressed at comparable levels; in particular C687Y and C687Y/H875Y were expressed at lower levels.

Figure 27A:
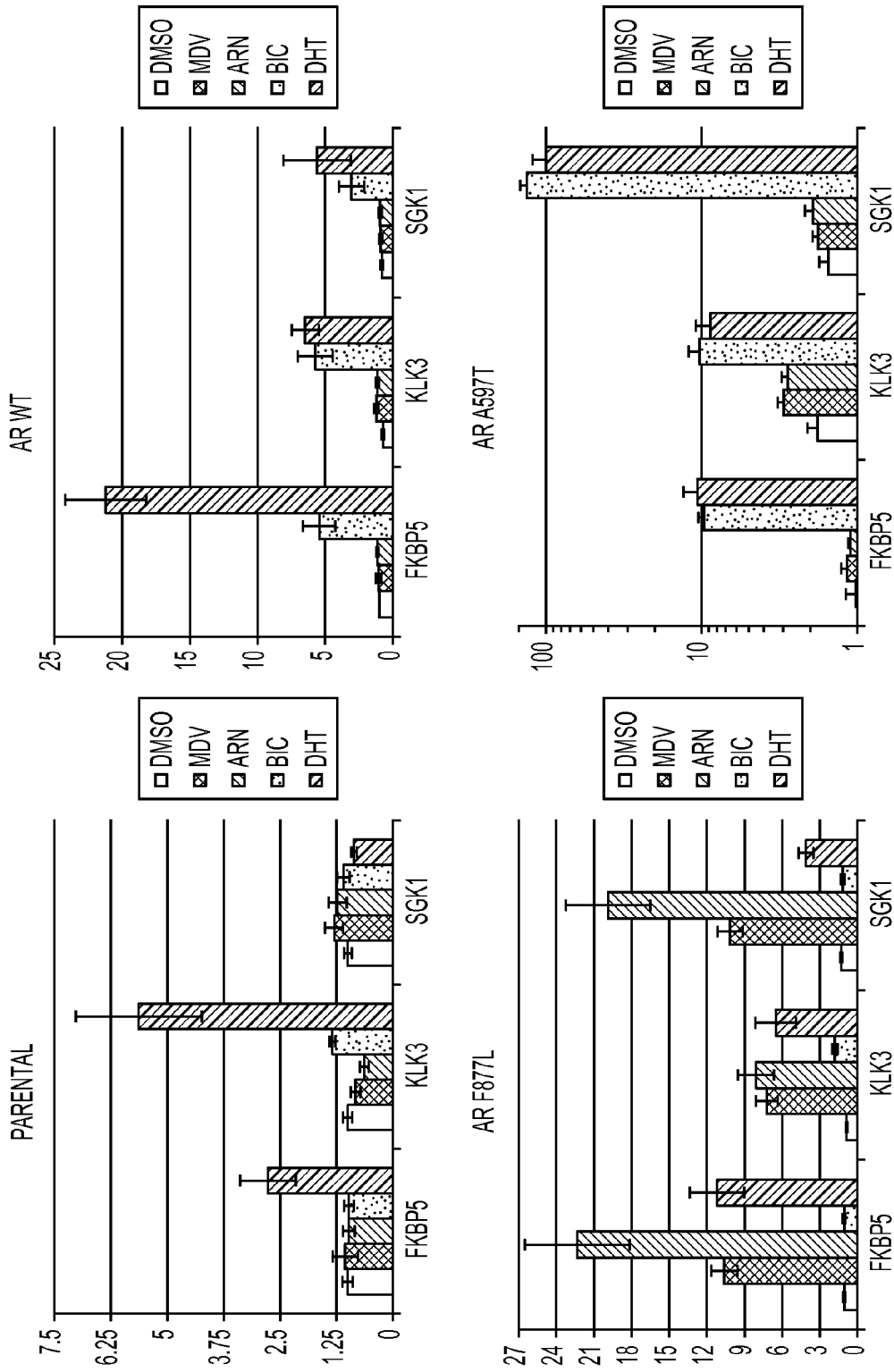
Figure 27B:
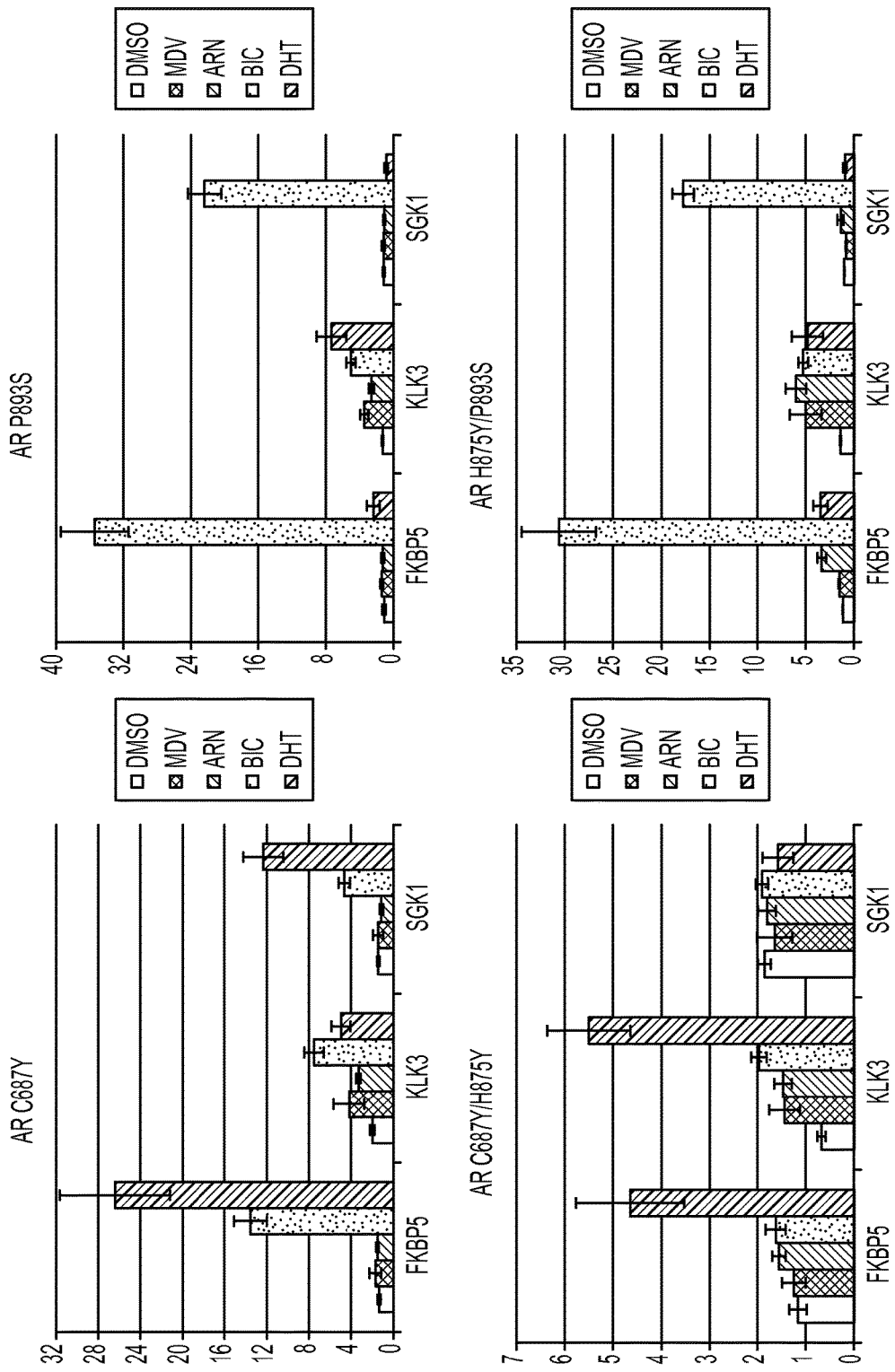

FIGS. 27A-27B show qRT-PCR data from LNCaP/Pb.PSE.EGFP cells expressing the indicated AR mutants. The cells were cultured in CSS containing media and treated with either vehicle (DMSO), 10 μM antiandrogen, or 1 nM DHT and RNA was collected 24 hours later. These data suggest that all of these mutants remained sensitive to enzalutamide and ARN-509, although to variable degrees and with gene-specific differences.

Figure 28A:
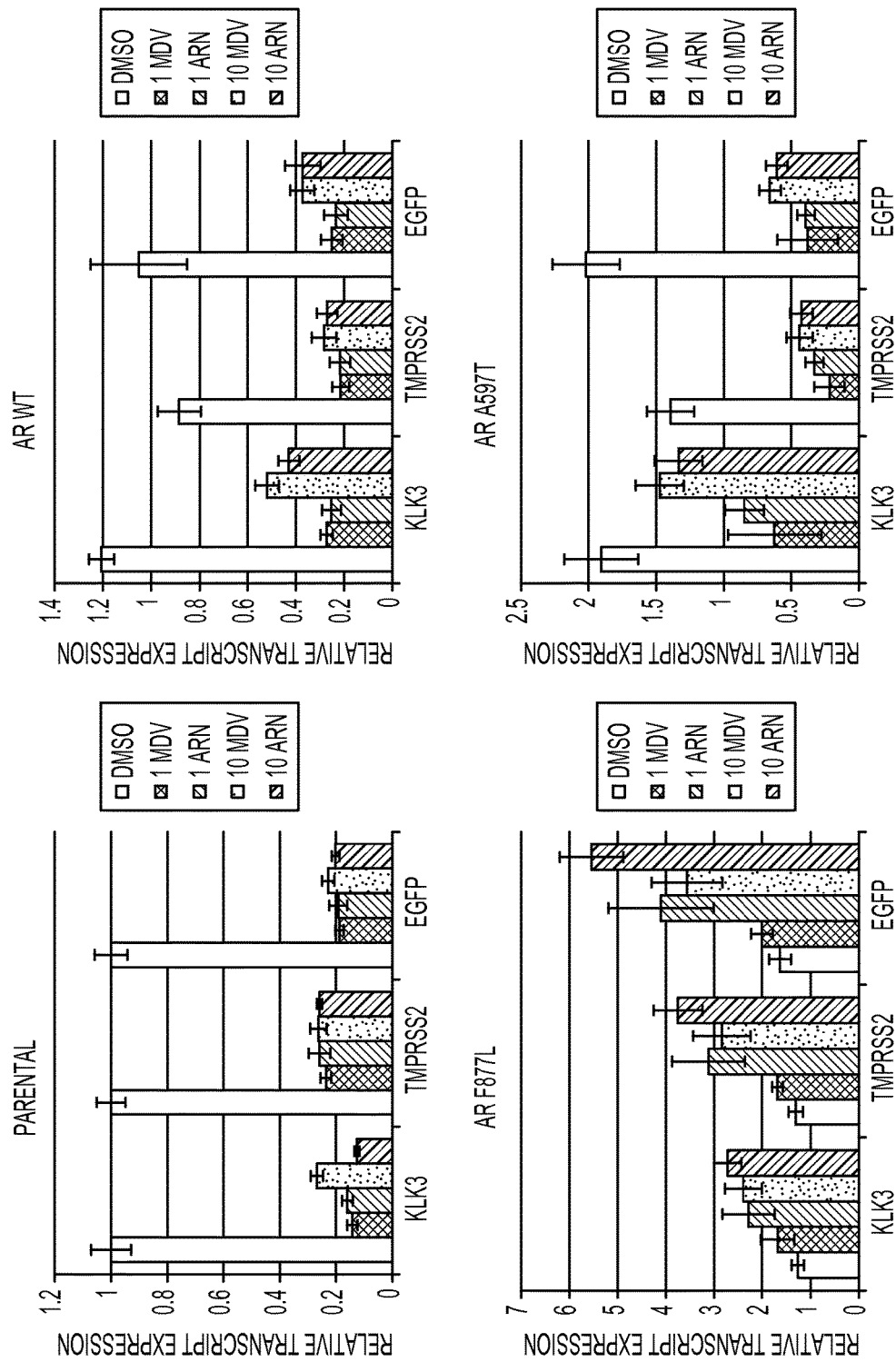
Figure 28B:
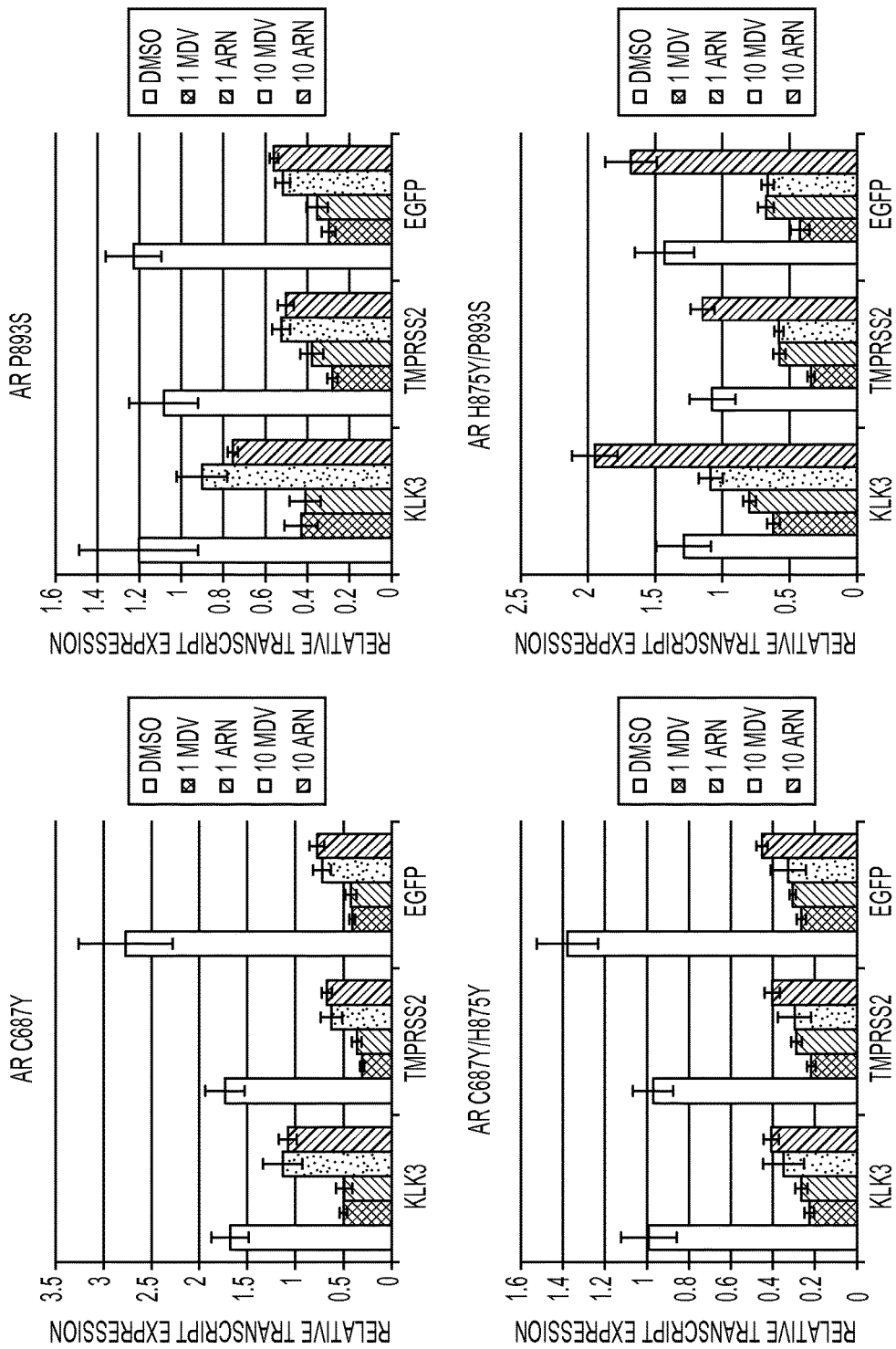

FIGS. 28A-28B show qRT-PCR data from LNCaP/Pb.PSE.EGFP cells expressing the indicated AR mutants. The cells were cultured in CSS containing media and treated with either vehicle (DMSO), 10 μM antiandrogen, or 1 nM DHT and RNA was collected 24 hours later. These data suggest that all of these mutants remained sensitive to enzalutamide and ARN-509, although to variable degrees and with gene-specific differences.

DEFINITIONS

Agents: As used herein, the term "agents" refers to any compounds or compositions that act as modulators (e.g., inhibitors or activators) and/or that contain a (directly or indirectly) detectable moiety. In general, agents can be of any chemical class including, for example, polypeptides, nucleic acids, saccharides, lipids, small molecules, metals, or combinations thereof. In some embodiments, agents can be or comprise cells or organisms, or any fraction, extract, or component thereof. In some embodiments, agents are natural products in that they are found in and/or obtained from nature. In some embodiments, agents are man-made in that they are designed, engineered, and/or produced through action of the hand of man and/or are not found in nature. In some embodiments, agents are utilized in isolated or pure form; in some embodiments, agents are utilized in crude form. In some embodiments, potential agents are provided as collections or libraries, for example that may be screened to identify active agents within them. Some particular embodiments of agents that may be utilized in accordance with the present invention include small molecules, antibodies, antibody fragments, aptamers, siRNAs, shRNAs, DNA/RNA hybrids, antisense oligonucleotides, ribozymes, peptides, peptide mimetics, etc. In some embodiments, agents are polymers. In some embodiments, agents are not polymers. In some embodiments, agents contain at least one polymeric moiety. In some embodiments, agents are non-polymeric.

Allele: The term "allele" refers to alternative forms of a gene or a portion thereof. Alleles occupy the same locus or position on homologous chromosomes. When an individual has two identical alleles of a gene, the individual is said to be homozygous for the gene or allele. When an individual has two different alleles of a gene, the individual is said to be heterozygous for the gene. Alleles of a specific gene can differ from each other in a single nucleotide or in a plurality nucleotides, and can include substitutions, deletions, and/or insertions of nucleotides with respect to each other. An allele of a gene can also be a form of a gene containing a mutation.

Androgen: The term "androgen" is used herein to refer to agents androgenic activity. Androgenic activity may be determined or characterized in any of a variety of ways, including in any of a variety of biological activity assays (e.g., in vitro or in vivo assays, for example utilizing animals and/or animal tissues) in which the agent is observed to have one or more activities similar or comparable to that of a known androgen assessed under comparable conditions (whether simultaneously or otherwise). In some embodiments, androgenic activity is or comprises transcriptional regulation (e.g., activation) of an androgen-responsive target gene. In some embodiments, androgenic activity is or comprises stimulation of prostate growth in rodents. Exemplary know androgens include, for example, androstanedione, androstenediol, androstenedione, androsterone, dehydroepiandrosterone, dihydrotestosterone (DHT), and testosterone.

Androgen receptor polypeptide: In accordance with the present invention, the term "Androgen receptor polypeptide" is used to refer to a polypeptide that 1) shares an overall level of sequence identity and/or 2) shares at least one characteristic sequence element with a reference androgen receptor protein, for example as set forth in Table 1. In some embodiments, an androgen receptor polypeptide shows an overall level of sequence identity of at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% overall sequence identity with the reference androgen receptor polypeptide. In some embodiments, a characteristic sequence element of a wild type androgen receptor is or comprises FXXLF. In some embodiments, reference androgen receptor is a wild-type androgen receptor. In some embodiments, the reference androgen polypeptide is SEQ ID NO: 1, or a characteristic fragment thereof.

Antiandrogen: As used herein, the term "antiandrogen" refers to any agent that inhibits biological activity of androgens. In some embodiments, antiandrogens inhibit biological activity of an AR. In some embodiments antiandrogens inhibit biological activity of a wild type AR. In some embodiments, antiandrogens inhibit biological activity of one or more AR. In some embodiments, antiandrogens compete with one or more androgens for binding to an AR. In some embodiments, antiandrogens compete with one or more androgens for binding to a wild type AR. In some embodiments, antiandrgens compete with one or more androgens for binding to an AR. In some embodiments, antiandrogens comprise 3,3'-diindolylmethane (DIM), ARN-509, bexlosteride, bicalutamide, dutasteride, epristeride, enzalutamide, finasteride, flutamide, izonsteride, ketoconazole, N-butylbenzene-sulfonamide, nilutamide, megestrol, steroidal antiandrogens, and/or turosteride.

Antibody: As used herein, the term "antibody" refers to an immunoglobulin, or an antigen-binding fragment (e.g., Fab, Fab', F(ab')2, etc.) or derivative (e.g., s scFv, Fv, dsFv diabody, Fd). In some embodiments, an antibody is monoclonal. In some embodiments, an antibody is polyclonal. In some embodiments, an antibody is or comprises a polypeptide whose amino acid sequence includes all or a characteristic portion of an immunoglobulin constant domain (e.g., of an IgG, IgM, IgA, IgD, or IgE constant domain); in some such embodiments, the constant domain is a human constant domain. In some embodiments, an antibody is or comprises a polypeptide whose amino acid sequence includes all or a characteristic portion of an immunoglobulin variable domain; in some such embodiments the variable domain comprises CDR1, CDR2, and/or CDR3 sequence elements sufficient to permit and achieve specific binding to an antigen. In some such embodiments, one or more of such CDR1, CDR2, and CDR3 sequence elements is a human element. In some embodiments, an antibody is produced by synthesis. In some embodiments, an antibody is produced by a cell or cell line (e.g., a hybridoma). In some embodiments, an antibody is produced by an organism.

Carrier: As used herein, the term "carrier" refers to a pharmaceutically acceptable (e.g., safe and non-toxic for administration to a human) carrier substance useful for preparation of a pharmaceutical formulation. In many embodiments, a carrier is biologically substantially inert, e.g., so that activity of a biologically active substance is not materially altered in its presence as compared with in its absence. In some embodiments, a carrier is a diluent.

Characteristic fragment As used herein, the phrase "characteristic fragment" refers to a portion of an entity or agent that represents a contiguous structural piece of the whole that is characteristic of the whole in that it shares at least one activity or attribute of the whole. In some embodiments, a characteristic fragment includes at least 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%, of the structural elements (e.g., atoms, moieties or monomer elements such as, for example, amino acids or nucleotides) present in the parent full-length entity or agent. In general, a characteristic fragment of a polymeric entity or agent (e.g., of a nucleic acid or a polypeptide) includes at least 5, 6, 7, 8, 9, 10, 11, 12, 13, 14, 15, 16, 17, 18, 19, 20, 21, 22, 23, 24, 25, 26, 27, 28, 29, 30 or more contiguous monomer elements (e.g., nucleic acids or amino acids) as found in the intact polymeric entity or agent.

Characteristic sequence element: A "characteristic sequence element" is a sequence that is found in members of a family of polypeptides or nucleic acids, such that it can be used by those of ordinary skill in the art to define members of the family. In some embodiments, a characteristic sequence is found in a wild type polypeptide sequence. Those skilled in the art will appreciate that a characteristic sequence element may involve residues that are separated from one another in a polypeptide or nucleic acid chain (i.e., are not contiguous to one another). Typically, a characteristic sequence element will include at least one stretch of 2, 3, 4, 5, 6, 7, 8, 9, 10, 11, 12, 13, 14, 15 or more contiguous residues, as well as at least one non-contiguous residue or stretch of residues.

Comparable: The term "comparable" as used herein refers to a system, set of conditions, effects, or results that is/are sufficiently similar to a test system, set of conditions, effects, or results, to permit scientifically legitimate comparison. Those of ordinary skill in the art will appreciate and understand which systems, sets of conditions, effect, or results are sufficiently similar to be "comparable" to any particular test system, set of conditions, effects, or results as described herein.

Correlates: The term "correlates", as used herein, has its ordinary meaning of "showing a correlation with". Those of ordinary skill in the art will appreciate that two features, items or values show a correlation with one another if they show a tendency to appear and/or to vary, together. In some embodiments, a correlation is statistically significant when its p-value is less than 0.05; in some embodiments, a correlation is statistically significant when its p-value is less than 0.01. In some embodiments, correlation is assessed by regression analysis. In some embodiments, a correlation is a correlation coefficient.

Corresponding to: As used herein, the term "corresponding to" is often used to designate the position/identity of a particular residue within a polymeric agent (e.g., within a nucleic acid or polypeptide). Those of ordinary skill will appreciate that, for purposes of simplicity, a canonical numbering system (based on a reference polymer) is often utilized herein in order to facilitate comparison of polymer sequences. Those of ordinary skill in the art understand how to align polymer sequences in order to determine which residues "correspond" to particular positions in a reference polymer. For example, those skilled in the art appreciate that a particular residue in a polypeptide of interest may "correspond to" a residue at a certain position in a reference polypeptide even if it is not found at the same position (relative to a terminus of the polypeptide) in the polypeptide of interest, so long as its context in the polypeptide of interest is sufficiently similar to that of the residue in the polypeptide of interest that it would be recognized by one skilled in the art as "corresponding to" that reference residue.

Differentiates: The term "differentiates", as used herein, indicates defining or distinguishing from other entities (e.g., comparable entities). In some embodiments, differentiates means distinguishing from other types with which present together in source and/or sample.

Dosage form: As used herein, the terms "dosage form" and "unit dosage form" refer to a physically discrete unit of a therapeutic composition for administration to a subject to be treated. Each unit dosage form contains a predetermined quantity of active agent calculated to produce a desired therapeutic effect when administered in accordance with a dosing regimen. It will be understood, however, that a total dosage of the active agent may be decided by an attending physician within the scope of sound medical judgment.

Dosing regimen: A "dosing regimen" (or "therapeutic regimen"), as that term is used herein, is a set of unit doses (typically more than one) that are administered individually to a subject, typically separated by periods of time. In some embodiments, a given therapeutic agent has a recommended dosing regimen, which may involve one or more doses. In some embodiments, a dosing regimen comprises a plurality of doses each of which is separated from one another by a time period of the same length; in some embodiments, a dosing regime comprises a plurality of doses and at least two different time periods separating individual doses. In some embodiments, the therapeutic agent is administered continuously over a predetermined period. In some embodiments, the therapeutic agent is administered once a day (QD) or twice a day (BID).

Identity: As used herein, the term "identity" refers to the structural relatedness between or among polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. Those skilled in the art are well familiar with strategies for comparing and determining percent identity between or among nucleic acid or polypeptide sequences. For example, a variety of mathematical algorithms are know for performing such comparisons To give but a few examples, percent identity between two (or more) nucleotide sequences can be determined using the algorithm of Meyers and Miller (CABIOS, 1989, 4: 11-17), which has been incorporated into the ALIGN program (version 2.0) using a PAM 120 weight residue table, a gap length penalty of 12 and a gap penalty of 4. Percent identity between two nucleotide sequences can, alternatively, be determined using the GAP program in the GCG software package using an NWSgapdna.CMP matrix.

Improve, increase, or reduce: As used herein, the terms "improve," "increase" or "reduce," or grammatical equivalents, indicate a change in a value relative to a comparable baseline or reference measurement. In some embodiments, a comparable baseline or reference measurement is a measurement taken in the same system (e.g., of the same individual) prior to initiation of an event of interest (e.g., of therapy). In some embodiments, a comparable baseline or reference measurement is one taken in a different system (e.g., a different individual or cell) under otherwise identical conditions (e.g., in a normal cell or individual as compared with one suffering from or susceptible to a particular disease, disorder or condition, for example due to presence of a particular genetic mutation).

In vitro: As used herein, the term "in vitro" refers to events that occur in an artificial environment, e.g., in a test tube or reaction vessel, in cell culture, etc., rather than within a multi-cellular organism.

In vivo: As used herein, the term "in vivo" refers to events that occur within a multi-cellular organism, such as a human and a non-human animal. In the context of cell-based systems, the term may be used to refer to events that occur within a living cell (as opposed to, for example, in vitro systems).

Isolated: As used herein, the term "isolated" is used to refer to a substance and/or entity that has been (1) separated from at least some of the components with which it was associated when initially produced (whether in nature and/or in an experimental setting), and/or (2) produced, prepared, and/or manufactured by the hand of man. Isolated substances and/or entities may be separated from at least about 10%, about 20%, about 30%, about 40%, about 50%, about 60%, about 70%, about 80%, about 90%, about 95%, about 98%, about 99%, substantially 100%, or 100% of the other components with which they were initially associated. In some embodiments, isolated agents are more than about 80%, about 85%, about 90%, about 91%, about 92%, about 93%, about 94%, about 95%, about 96%, about 97%, about 98%, about 99%, substantially 100%, or 100% pure. As used herein, a substance is "pure" if it is substantially free of other components. As used herein, the term "isolated cell" refers to a cell not contained in a multi-cellular organism.

Mutant: As used herein, the term "mutant" refers to an altered (as compared with a reference) nucleic acid or polypeptide, or to a cell or organism containing or expressing such an altered nucleic acid or polypeptide.

Mutation: As used herein, the term "mutation" refers to a change introduced into a parental sequence, including, but not limited to, substitutions, insertions, deletions (including truncations). The consequences of a mutation include, but are not limited to, the creation of a new character, property, function, phenotype or trait not found in the protein encoded by the parental sequence, or the reduction or elimination of an existing character, property, function, phenotype or trait not found in the protein encoded by the parental sequence.

Nucleic Acid: The terms "nucleic acid", "nucleic acid molecule", and "polynucleotide" each is used herein to refer to a polymers of nucleotide monomers or analogs thereof, such as deoxyribonucleic acid (DNA) and ribonucleic acid (RNA). Unless otherwise stated, the terms encompass nucleic acid-like structures with synthetic backbones, as well as amplification products. In some embodiments, nucleic acids involved in the present invention are linear nucleic acids.

Polypeptide: The term "polypeptide" or "peptide", as used herein, generally has its art-recognized meaning of a polymer of at least three amino acids. Those of ordinary skill in the art will appreciate that the term "polypeptide" is intended to be sufficiently general as to encompass not only polypeptides having a complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein.

Protein: The term "protein" as used herein refers to one or more polypeptides that function as a discrete unit. If a single polypeptide is the discrete functioning unit and does not require permanent or temporary physical association with other polypeptides in order to form the discrete functioning unit, the terms "polypeptide" and "protein" may be used interchangeably. If the discrete functional unit is comprised of more than one polypeptide that physically associate with one another, the term "protein" may be used to refer to the multiple polypeptides that are physically associated and function together as the discrete unit.

Risk: As will be understood from context, a "risk" of a disease, disorder or condition (e.g., CRPC) comprises a likelihood that a particular individual will develop the disease, disorder, or condition. In some embodiments, risk is expressed as a percentage. In some embodiments, risk is from 0, 1, 2, 3, 4, 5, 6, 7, 8, 9, 10 up to 100%. In some embodiments risk is expressed as a risk relative to a risk associated with a reference sample or group of reference samples. In some embodiments, a reference sample or group of reference samples have a known risk of a disease, disorder, or condition (CRPC). In some embodiments a reference sample or group of reference samples are from individuals comparable to a particular individual. In some embodiments, relative risk is 0, 1, 2, 3, 4, 5, 6, 7, 8, 9, 10 or more.

Reference: As will be understood from context, a reference sequence, sample, population, agent or individual is one that is sufficiently similar to a particular sequence, sample, population, agent or individual of interest to permit a relevant comparison (i.e., to be comparable). In some embodiments, information about a reference sample is obtained simultaneously with information about a particular sample. In some embodiments, information about a reference sample is historical. In some embodiments, information about a reference sample is stored for example in a computer-readable medium. In some embodiments, comparison of a particular sample of interest with a reference sample establishes identity with, similarity to, or difference of a particular sample of interest relative to a reference.

Sample: As used herein, the term "sample" typically refers to a biological sample obtained or derived from a source of interest, as described herein. In some embodiments, a source of interest comprises an organism, such as an animal or human. In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid; peritoneal fluid; pleural fluid; feces; lymph; gynecological fluids; skin swabs; vaginal swabs; oral swabs; nasal swabs; washings or lavages such as a ductal lavages or broncheoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Suffering from: An individual who is "suffering from" a disease, disorder, and/or condition has been diagnosed with or displays one or more symptoms of the disease, disorder, and/or condition.

Therapeutically effective amount: As used herein, the term "therapeutically effective amount" refers to an amount of an agent which confers a therapeutic effect on a treated subject, at a reasonable benefit/risk ratio applicable to any medical treatment. A therapeutic effect may be objective (i.e., measurable by some test or marker) or subjective (i.e., subject gives an indication of or feels an effect). In particular, a "therapeutically effective amount" refers to an amount of a therapeutic agent effective to treat, ameliorate, or prevent a desired disease or condition, or to exhibit a detectable therapeutic or preventative effect, such as by ameliorating symptoms associated with a disease, preventing or delaying onset of a disease, and/or also lessening severity or frequency of symptoms of a disease. A therapeutically effective amount is commonly administered in a dosing regimen that may comprise multiple unit doses. For any particular therapeutic agent, a therapeutically effective amount (and/or an appropriate unit dose within an effective dosing regimen) may vary, for example, depending on route of administration, on combination with other agents. Also, a specific therapeutically effective amount (and/or unit dose) for any particular patient may depend upon a variety of factors including what disorder is being treated; disorder severity; activity of specific agents employed; specific composition employed; age, body weight, general health, and diet of a patient; time of administration, route of administration; treatment duration; and like factors as is well known in the medical arts.

Treatment: As used herein, the term "treat," "treatment," or "treating" refers to any method used to partially or completely alleviate, ameliorate, relieve, inhibit, prevent, delay onset of, reduce severity of and/or reduce incidence of one or more symptoms or features of a particular disease, disorder, and/or condition. Treatment may be administered to a subject who does not exhibit signs of a disease and/or exhibits only early signs of the disease for the purpose of decreasing the risk of developing pathology associated with the disease.

Vector: As used herein, the term "vector" refers to a nucleic acid molecule capable of transporting another nucleic acid to which it has been linked and can include a plasmid, cosmid or viral vector. The vector can be capable of autonomous replication or it can integrate into a host DNA. Viral vectors include, e.g., replication defective retroviruses, adenoviruses and adeno-associated viruses.

Wild type: As used herein, the term "wild-type" refers to a typical or common form existing in nature; in some embodiments it is the most common form.

DETAILED DESCRIPTION OF CERTAIN EMBODIMENTS

Androgen Receptor

The androgen receptor (AR), located on Xq1 1-12, is a 110 kD nuclear receptor that, upon activation by androgens, mediates transcription of target genes that modulate growth and differentiation of prostate epithelial cells. Similar to other steroid receptors, unbound AR is mainly located in cytoplasm and associated with a complex of heat shock proteins (HSPs) through interactions with its ligand-binding domain. Upon agonist binding, AR undergoes a series of conformational changes: heat shock proteins dissociate from AR, and transformed AR undergoes dimerization, phosphorylation, and nuclear translocation, which is mediated by its nuclear localization signal. Translocated receptor then binds to androgen response elements (ARE), which are characterized by a six-nucleotide half-site consensus sequence 5'-TGTTCT-3' spaced by three random nucleotides and are located in promoter or enhancer regions of AR gene targets. Recruitment of other transcription co- regulators (including co-activators and co-repressors) and transcriptional machinery further ensures transactivation of AR-regulated gene expression. All of these processes are initiated by the ligand-induced conformational changes in the ligand-binding domain.

"Androgen-dependent disorder" refers to any disorder that can benefit from a decrease in androgen stimulation and includes pathological conditions that depend on androgen stimulation. An "androgen-dependent disorder" can result from an excessive accumulation of testosterone or other androgenic hormone, increased sensitivity of androgen receptors to androgen, or an increase in androgen-stimulated transcription. Examples of "androgen-dependent disorders" include prostate cancer and skin disorders such as, for example, acne, seborrhea, hirsutism, alopecia, or hidradenitis suppurativa.

Prostate Cancer

Prostate cancer is the second most common cause of cancer death in men in the US, and approximately one in every six American men will be diagnosed with the disease during his lifetime. Treatment aimed at eradicating the tumor is unsuccessful in 30% of men, who develop recurrent disease that is usually manifest first as a rise in plasma prostate-specific antigen (PSA) followed by spread to distant sites.

AR signaling is crucial for development and maintenance of male reproductive organs including prostate glands, as genetic males harboring loss of function AR mutations and mice engineered with AR defects do not develop prostates or prostate cancer. This dependence of prostate cells on AR signaling continues even upon neoplastic transformation.

Given that prostate cancer cells depend on AR for their proliferation and survival, these men are treated with agents that block production of testosterone (e.g. GnRH agonists), alone or in combination with antiandrogens, which antagonize effects of any residual testosterone. This approach is effective as evidenced by a drop in PSA and regression of any visible tumor.

Antiandrogens

Anti-androgens are useful for the treatment of prostate cancer during its early stages. However, prostate cancer often advances to a hormone-refractory state in which the disease progresses despite continued androgen ablation or anti-androgen therapy. Antiandrogens include but are not limited to flutamide, nilutamide, bicalutamide, and/or megestrol.

Recently, more effective second generation antiandrogens have been developed. These include but are not limited to ARN-509 and enzalutamide, which are thought to function both by inhibiting AR nuclear translocation and DNA binding.

Castration Resistant Prostate Cancer

This hormone-refractory state to which most patients eventually progresses in the presence of continued androgen ablation or anti-androgen therapy is known as "castration resistant" prostate cancer (CRPC).

Compelling data demonstrates that AR is expressed in most prostate cancer cells and overexpression of AR is necessary and sufficient for androgen-independent growth of prostate cancer cells. Failure in hormonal therapy, resulting from development of androgen-independent growth, is an obstacle for successful management of advanced prostate cancer. Instances of antiandrogen withdrawal syndrome have also been reported after prolonged treatment with antiandrogens. Antiandrogen withdrawal syndrome is commonly observed clinically and is defined in terms of tumor regression or symptomatic relief observed upon cessation of antiandrogen therapy. AR mutations that result in receptor promiscuity and the ability of these antiandrogens to exhibit agonist activity might at least partially account for this phenomenon. For example, hydroxyflutamide and bicalutamide act as AR agonists in T877A, W741L and W741C AR mutants, respectively.

Treatment options for CRPC are an unmet need. Until recently, docetaxel was the only agent shown to prolong survival. More recently, four newer treatments have come onto the market, including sipuleucel-T, an immunotherapeutic agent; cabazitaxel, a novel microtubule inhibitor; abiraterone acetate, a new androgen biosynthesis inhibitor; and denosumab. Interestingly, while a small minority of CRPC does bypass the requirement for AR signaling, the vast majority of CRPC, though frequently termed "androgen independent prostate cancer" or "hormone refractory prostate cancer," retains its lineage dependence on AR signaling.

AR Peptides and Production

AR has been purified, characterized, cloned and sequenced from both mouse and human sources. The AR protein contains 920 amino acid residues. Exemplary amino acid and nucleotide sequences from a full-length human AR polypeptide are shown below as SEQ IDs NO: 1 and 2. In some embodiments, an AR polypeptide includes at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, 300, 350, or 400 consecutive amino acids of a AR polypeptide sequence, e.g., at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, 300, 350, or 400 consecutive amino acids of the sequence shown in SEQ ID NO: 1 or of a sequence at least 60% (e.g., at least 65%, 70%, 75%, 80%, 85%, 90%, 95%, or 98%) identical to SEQ ID NO: 1. In some embodiments, an AR polypeptide comprises an amino acid sequence that is at least 60% (e.g., at least 65%, 70%, 75%, 80%, 85%, 90%, 95%, or 98%) identical to at least 7, 8, 9, 10, 11, 12, 13, 14, 15, 16, 17, 18, 19, 20, 25, 30, 35, 45, 50, 60, 65, 70, 75, 80, 85, 90, 95, 100, 150, 200, 250, 300, 350, or 400 consecutive amino acids of the sequence shown in SEQ ID NO: 1. In some embodiments, an AR polypeptide is a full-length AR polypeptide (e.g., the polypeptide comprises the amino acid sequence of SEQ ID NO: 1).

TABLE 1

I.

| | |
|---|---|
| Human AR Protein Sequence (GenBank: AAA51729.1) | MEVQLGLGRVYPRPPSKTYRGAFQNLFQSVREVIQNP GPRHPEAASAAPPGASLLLLQQQQQQQQQQQQQQQQQ QQQQETSPRQQQQQQGEDGSPQAHRRGPTGYLVLDEE QQPSQPQSALECHPERGCVPEPGAAVAASKGLPQQLP APPDEDDSAAPSTLSLLGPTFPGLSSCSADLKDILSE ASTMQLLQQQQQEAVSEGSSSGRAREASGAPTSSKDN YLGGTSTISDNAKELCKAVSVSMGLGVEALEHLSPGE QLRGDCMYAPLLGVPPAVRPTPCAPLAECKGSLLDDS AGKSTEDTAEYSPFKGGYTKGLEGESLGCSGSAAAGS SGTLELPSTLSLYKSGALDEAAAYQSRDYYNFPLALA GPPPPPPPPHPHARIKLENPLDYGSAWAAAAAQCRYG DLASLHGAGAAGPGSGSPSAAASSSWHTLFTAEEGQL YGPCGGGGGGGGGGGGGGGGGGGGGGGEAGAVAPYG YTRPPQGLAGQESDFTAPDVWYPGGMVSRVPYPSPTC VKSEMGPWMDSYSGPYGDMRLETARDHVLPIDYYFPP QKTCLICGDEASGCHYGALTCGSCKVFFKRAAEGKQK YLCASRNDCTIDKFRRKNCPSCRLRKCYEAGMTLGAR KLKKLGNLKLQEEGEASSTTSPTEETTQKLTVSHIEG YECQPIFLNVLEAIEPGVVCAGHDNNQPDSFAALLSS LNELGERQLVHVVKWAKALPGFRNLHVDDQMAVIQYS WMGLMVFAMGWRSFTNVNSRMLYFAPDLVFNEYRMHK SRMYSQCVRMRHLSQEFGWLQITPQEFLCMKALLLFS IIPVDGLKNQKFFDELRMNYIKELDRIIACKRKNPTS CSRRFYQLTKLLDSVQPIARELHQFTFDLLIKSHMVS VDFPEMMAEIISVQVPKILSGKVKPIYFHTQ (SEQ ID NO: 1) |

TABLE 1-continued

I.

Human AR
mRNA
Sequence
(GenBank:
M20132.1)

TAATAACTCAGTTCTTATTTGCACCTACTTCAGTGGA
CACTGAATTTGGAAGGTGGAGGATTTTGTTTTTTCT
TTTAAGATCTGGGCATCTTTTGAATCTACCCTTCAAG
TATTAAGAGACAGACTGTGAGCCTAGCAGGGCAGATC
TTGTCCACCGTGTGTCTTCTTCTGCACGAGACTTTGA
GGCTGTCAGAGCGCTTTTTGCGTGGTTGCTCCCGCAA
GTTTCCTTCTCTGGAGCTTCCCGCAGGTGGGCAGCTA
GCTGCAGCGACTACCGCATCATCACAGCCTGTTGAAC
TCTTCTGAGCAAGAGAAGGGGAGGCGGGGTAAGGGAA
GTAGGTGGAAGATTCAGCCAAGCTCAAGGATGGAAGT
GCAGTTAGGGCTGGGAAGGGTCTACCCTCGGCCGCCG
TCCAAGACCTACCGAGGAGCTTTCCAGAATCTGTTCC
AGAGCGTGCGCGAAGTGATCCAGAACCCGGGCCCCAG
GCACCCAGAGGCCGCGAGCGCAGCACCTCCCGGCGCC
AGTTTGCTGCTGCTGCAGCAGCAGCAGCAGCAGCAGC
AGCAGCAGCAGCAGCAGCAGCAGCAGCAGCAGCAGCA
GCAAGAGACTAGCCCCAGGCAGCAGCAGCAGCAGCAG
GGTGAGGATGGTTCTCCCCAAGCCCATCGTAGAGGCC
CCACAGGCTACCTGGTCCTGGATGAGGAACAGCAACC
TTCACAGCCGCAGTCGGCCCTGGAGTGCCACCCCGAG
AGAGGTTGCGTCCCAGAGCCTGGAGCCGCCGTGGCCG
CCAGCAAGGGGCTGCCGCAGCAGCTGCCAGCACCTCC
GGACGAGGATGACTCAGCTGCCCCATCCACGTTGTCC
CTGCTGGGCCCCACTTTCCCCGGCTTAAGCAGCTGCT
CCGCTGACCTTAAAGACATCCTGAGCGAGGCCAGCAC
CATGCAACTCCTTCAGCAACAGCAGCAGGAAGCAGTA
TCCGAAGGCAGCAGCAGCGGGAGAGCGAGGGAGGCCT
CGGGGGCTCCCACTTCCTCCAAGGACAATTACTTAGG
GGGCACTTCGACCATTTCTGACAACGCCAAGGAGTTG
TGTAAGGCAGTGTCGGTGTCCATGGGCCTGGGTGTGG
AGGCGTTGGAGCATCTGAGTCCAGGGGAACAGCTTCG
GGGGGATTGCATGTACGCCCCACTTTTGGGAGTTCCA
CCCGCTGTGCGTCCCACTCCTTGTGCCCCATTGGCCG
AATGCAAAGGTTCTCTGCTAGACGACAGCGCAGGCAA
GAGCACTGAAGATACTGCTGAGTATTCCCCTTTCAAG
GGAGGTTACACCAAAGGGCTAGAAGGCGAGAGCCTAG
GCTGCTCTGGCAGCGCTGCAGCAGGGAGCTCCGGGAC
ACTTGAACTGCCGTCTACCCTGTCTCTCTACAAGTCC
GGAGCACTGGACGAGGCAGCTGCGTACCAGAGTCGCG
ACTACTACAACTTTCCACTGGCTCTGGCCGGACCGCC
GCCCCCTCCGCCGCCTCCCCATCCCCACGCTCGCATC
AAGCTGGAGAACCCGCTGGACTACGGCAGCGCCTGGG
CGGCTGCGGCGGCGCAGTGCCGCTATGGGGACCTGGC
GAGCCTGCATGGCGCGGGTGCAGCGGGACCCGGTTCT
GGGTCACCCTCAGCCGCCGCTTCCTCATCCTGGCACA
CTCTCTTCACAGCCGAAGAAGGCCAGTTGTATGGACC
GTGTGGTGGTGGTGGGGGTGGTGGCGGCGGCGGCGGC
GGCGGCGGCGGCGGCGGCGGCGGCGGCGGCGGCGGCG
GCGAGGCGGGAGCTGTAGCCCCCTACGGCTACACTCG
GCCCCCTCAGGGGCTGGCGGGCCAGGAAAGCGACTTC
ACCGCACCTGATGTGTGGTACCCTGGCGGCATGGTGA
GCAGATGCCCTATCCCAGTCCCACTTGTGTCAAAAG
CGAAATGGGCCCCTGGATGGATAGCTACTCCGGACCT
TACGGGGACATGCGTTTGGAGACTGCCAGGGACCATG
TTTTGCCCATTGACTATTACTTTCCACCCCAGAAGAC
CTGCCTGATCTGTGGAGATGAAGCTTCTGGGTGTCAC
TATGGAGCTCTCACATGTGGAAGCTGCAAGGTCTTCT
TCAAAAGAGCCGCTGAAGGGAAACAGAAGTACCTGTG
CGCCAGCAGAAATGATTGCACTATTGATAAATTCCGA
AGGAAAAATTGTCCATCTTGTCGTCTTCGGAAATGTT
ATGAAGCAGGGATGACTCTGGGAGCCCGGAAGCTGAA
GAAACTTGGTAATCTGAAACTACAGGAGGAAGGAGAG
GCTTCCAGCACCACCAGCCCCACTGAGGAGACAACCC
AGAAGCTGACAGTGTCACACATTGAAGGCTATGAATG
TCAGCCCATCTTTCTGAATGTCCTGGAAGCCATTGAG
CCAGGTGTAGTGTGTGCTGGACGACAACAACCAGC
CCGACTCCTTTGCAGCCTTGCTCTCTAGCCTCAATGA
ACTGGGAGAGAGACAGCTTGTACACGTGGTCAAGTGG
GCCAAGGCCTTGCCTGGCTTCCGCAACTTACACGTGG
ACGACCAGATGGCTGTCATTCAGTACTCCTGGATGGG
GCTCATGGTGTTTGCCATGGGCTGGCGATCCTTCACC
AATGTCAACTCCAGGATGCTCTACTTCGCCCCTGATC
TGGTTTTCAATGAGTACCGCATGCACAAGTCCCGGAT
GTACAGCCAGTGTGTCCGAATGAGGCACCTCTCTCAA
GAGTTTGGATGCTCCAAATCACCCCCAGGAATTCC
TGTGCATGAAAGCACTGCTACTCTTCAGCATTATTCC
AGTGGATGGGCTGAAAAATCAAAATTCTTTGATGAA
CTTCGAATGAACTACATCAAGGAACTCGATCGTATCA

TTGCATGCAAAAGAAAAAATCCCACATCCTGCTCAAG
ACGCTTCTACCAGCTCACCAAGCTCCTGGACTCCGTG
CAGCCTATTGCGAGAGAGCTGCATCAGTTCACTTTTG
ACCTGCTAATCAAGTCACACATGGTGAGCGTGGACTT
TCCGGAAATGATGGCAGAGATCATCTCTGTGCAAGTG
CCCAAGATCCTTTCTGGGAAAGTCAAGCCCATCTATT
TCCACACCCAGTGAAGCATTGGAAACCCTATTTCCCC
ACCCCAGCTCATGCCCCCTTTCAGATGTCTTCTGCCT
GTTATAACTCTGCACTACTCCTCTGCAGTGCCTTGGG
GAATTTCCTCTATTGATGTACAGTCTGTCATGAACAT
GTTCCTGAATTCTATTTGCTGGGCTTTTTTTTTCTCT
TTCTCTCCTTTCTTTTTCTTCTTCCCTCCCTATCTAA
CCCTCCCATGGCACCTTCAGACTTTGCTTCCCATTGT
GGCTCCTATCTGTGTTTTGAATGGTGTTGTATGCCTT
TAAATCTGTGATGATCCTCATATGGCCCAGTGTCAAG
TTGTGCTTGTTTACAGCACTACTCTGTGCCAGCCACA
CAAACGTTTACTTATCTTATGCCACGGGAAGTTTAGA
GAGCTAAGATTATCTGGGGAAATCAAAACAAAAAACA
AGCAAACAAAAAAAAAA (SEQ ID NO: 2)

Nucleic Acid Compositions and Polypeptide Expression

Polynucleotides (e.g., DNA fragments) encoding an AR protein can be generated by any of a variety of procedures. They can be cleaved from larger polynucleotides (e.g., genomic sequences, cDNA, or the like) with appropriate restriction enzymes, which can be selected, for example, on the basis of published sequences of human AR. The mRNA sequence for human AR is shown in SEQ ID NO: 2.

In some embodiments, polynucleotides encoding an AR protein can be generated by PCR amplification by selecting appropriate primers based on published sequences such as those above. Methods of PCR amplification, including the selection of primers, conditions for amplification, and cloning of the amplified fragments, are conventional. See, e.g., Innis, M. A. et al., eds. PCR Protocols: a guide to methods and applications, 1990, Academic Press, San Diego, Calif. and Wu et al., eds., Recombinant DNA Methodology, 1989, Academic Press, San Diego, Calif. In some embodiments, polynucleotide fragments encoding an AR protein can be generated by chemical synthesis. Combinations of the above recombinant or non-recombinant methods, or other conventional methods, can also be employed.

An isolated polynucleotide encoding an AR protein or a fragment thereof can be cloned into any of a variety of expression vectors, under the control of a variety of regulatory elements, and expressed in a variety of cell types and hosts, including prokaryotes, yeast, and mammalian, insect or plant cells, or in a transgenic, non-human animal.

Various types of vectors are suitable for expression of AR polypeptides in an expression system (e.g., in a host cell). In some embodiments, a composition includes a vector suitable for expression in vitro (whether in a cell or in a cell-free system). The term "vector" refers to a nucleic acid molecule capable of transporting another nucleic acid to which it has been linked and can include, for example, a plasmid, cosmid or viral vector. The vector can be capable of autonomous replication or it can integrate into a host DNA. Viral vectors include, e.g., replication defective retroviruses, adenoviruses and adeno-associated viruses. Other types of viral vectors are known in the art.

A vector can include a nucleic acid encoding an AR polypeptide in a form suitable for expression of the nucleic acid in a host cell. A recombinant expression vector typically includes one or more regulatory sequences operatively linked to the nucleic acid sequence to be expressed. Regulatory sequences include promoters, enhancers and other expression control elements (e.g., polyadenylation signals). Regulatory sequences include those which direct constitutive expression of a nucleotide sequence, as well as tissue-specific regulatory and/or inducible sequences. A sequence encoding an AR polypeptide can include a sequence encoding a signal peptide (e.g., a heterologous signal peptide) such that the antigen is secreted from a host cell. The design of the expression vector can depend on such factors as the choice of the host cell to be transformed, the level of expression of protein desired, and the like.

Recombinant expression vectors can be designed for expression and production of AR polypeptides in prokaryotic or eukaryotic cells. For example, polypeptides can be expressed in *E. coli*, insect cells (e.g., using baculovirus expression vectors), yeast cells or mammalian cells. Suitable host cells are discussed further in Goeddel, *Gene Expression Technology: Methods in Enzymology* 185, Academic Press, San Diego, Calif., 1990. Alternatively, a recombinant expression vector can be transcribed and translated in vitro, for example using T7 promoter regulatory sequences and T7 polymerase.

Expression of polypeptides in prokaryotes is often carried out in *E. coli* with vectors containing constitutive or inducible promoters directing the expression of either fusion or non-fusion proteins. Fusion vectors add a number of amino acids to a protein encoded therein, e.g., to the amino terminus or carboxy terminus of the recombinant protein, e.g., to increase expression of recombinant protein; to increase the solubility of the recombinant protein; and/or to aid in the purification of the recombinant antigen by acting as a ligand in affinity purification. Often, a proteolytic cleavage site is introduced at the junction of the fusion moiety and the recombinant antigen to enable separation of the recombinant antigen from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. *Gene* 67:31-40, 1988), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

An expression vector for use in mammalian cells can include viral regulatory elements. For example, commonly used promoters are derived from polyoma, Adenovirus 2, cytomegalovirus and Simian Virus 40. A vector can include an inducible promoter, e.g., a promoter regulated by a steroid hormone, by a polypeptide hormone (e.g., by means of a signal transduction pathway), or by a heterologous polypeptide (e.g., the tetracycline-inducible systems, "Tet-On" and "Tet-Off"; see, e.g., Clontech Inc., CA, Gossen and Bujard, Proc. Natl. Acad. Sci. USA 89:5547, 1992, and Paillard, Human Gene Therapy 9:983, 1989).

A host cell can be any prokaryotic or eukaryotic cell. For example, an AR polypeptide can be expressed in bacterial cells (such as *E. coli*), insect cells, yeast or mammalian cells (such as Chinese hamster ovary cells (CHO) or COS cells (African green monkey kidney cells CV-1 origin SV40 cells; Gluzman, *Cell* 23:175-182, 1981). Other suitable host cells are known to those skilled in the art.

Vector DNA can be introduced into host cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, gene gun, or electroporation.

A host cell can be used to produce (i.e., express) an AR polypeptide. Accordingly, the invention further provides methods for producing an AR polypeptide using host cells. In one embodiment, the method includes culturing a host cell (into which a recombinant expression vector encoding an AR polypeptide has been introduced) in a suitable medium such that an AR polypeptide is produced. In some embodiments, the method further includes isolating an AR polypeptide from the medium or the host cell.

Anti-Androgen Resistant AR Mutants

The present invention encompasses the recognition that mutations in the AR polypeptide can render the AR polypeptide resistant to anti-androgens or convert anti-androgens to androgen agonists.

The amino acid sequence of an AR polypeptide described herein can be modified to produce an AR polypeptide variant at least one (e.g., 1, 2, 3, 4, 5, 6, 7, 8, 9, 10, or more) additions, substitutions, or deletions of a wild-type amino acid residue.

In some embodiments, the AR polypeptide variants described herein result in a loss of inhibition of AR activity by one or more antiandrogens of 0, 1, 2, 3, 4, 5, 6, 7, 8, 9, 10 up to 100%. In some embodiments, the AR polypeptide variants described herein convert anti-androgens to androgen receptor agonists.

Specific, nonlimiting amino acid residues that can be modified include, e.g., E565, E588, E668, C686, A699, N771, H776, C784, F876, K910, of the AR polypeptide. These amino acid residues can be substituted with any amino acid or amino acid analog. For example, the substitutions at the recited positions can be made with any of the naturally-occurring amino acids (e.g., alanine, aspartic acid, asparagine, arginine, cysteine, glycine, glutamic acid, glutamine, histidine, leucine, valine, isoleucine, lysine, methionine, proline, threonine, serine, phenylalanine, tryptophan, or tyrosine). In particular instances, an amino acid substitution is F876C, F876I, F876L, F876S, F876V, and/or F876Y. In some instances, an amino acid substitution is E565K, E588K, S647G, E668K, C686Y, D695E, A699T, R726H, N727I, N771S, H776Y, C784R, and/or K910E.

AR polypeptide variants as described herein can include additional modifications of the AR polypeptide previously described in the art, including but not limited to, e.g., A596T, S647G, P682T, D695E, R726H, N727I, I737F, W741L, W741C, W741L, M742V, G750S, A870V, H874Y, T877A, T877S, and P914S.

AR polypeptides having one or more amino acid residue modifications described herein can be produced according to molecular biology and recombinant gene expression methods known in the art and described herein.

Antibodies

This invention provides, inter alia, antibodies, or antigen-binding fragments thereof, to a novel AR polypeptide described herein. In some embodiments, an antibody binds to an androgen receptor polypeptide whose amino acid sequence shows at least 60% (e.g., at least 65%, 70%, 75%, 80%, 85%, 90%, 95%, or 98%) overall sequence identity with a reference wild type androgen receptor polypeptide of SEQ ID NO 1, which polypeptide includes a residue corresponding to residue 876, which corresponding residue is not leucine but does not bind to an androgen receptor polypeptide whose amino acid sequence shows at least 60% (e.g., at least 65%, 70%, 75%, 80%, 85%, 90%, 95%, or 98%) overall sequence identity with a reference wild type androgen receptor polypeptide of SEQ ID NO 1, which polypeptide includes a residue corresponding to residue 876, which corresponding residue is leucine. In some embodiments the antibodies, or antigen-binding fragments thereof, bind to a novel AR polypeptide e.g., an AR F876C polypeptide, an AR F876I polypeptide, an AR F876L polypeptide, an AR F876S polypeptide, an AR F876V polypeptide, an AR F876Y polypeptide.

In some embodiments, an antibody binds to an androgen receptor polypeptide whose amino acid sequence shows at least 60% (e.g., at least 65%, 70%, 75%, 80%, 85%, 90%, 95%, or 98%) overall sequence identity with a reference wild type androgen receptor polypeptide of SEQ ID NO 1, which polypeptide includes a mutation selected from E565K, E588K, S647G, E668K, C686Y, D695E, A699T, R726H, N727I, N771S, H776Y, C784R, and/or K910E but does not bind to an androgen receptor polypeptide whose amino acid sequence shows at least 60% (e.g., at least 65%, 70%, 75%, 80%, 85%, 90%, 95%, or 98%) overall sequence identity with a reference wild type androgen receptor polypeptide of SEQ ID NO 1, which polypeptide includes a residue corresponding to the wild type residue at the selected mutation.

The antibodies can be of the various isotypes, including: IgG (e.g., IgG1, IgG2, IgG3, IgG4), IgM, IgA1, IgA2, IgD, or IgE. In some embodiments, an antibody is an IgG isotype, e.g., IgG1. An antibody against AR can be full-length (e.g., an IgG1 or IgG4 antibody) or can include only an antigen-binding fragment (e.g., a Fab, F(ab)2, Fv or a single chain Fv fragment). These include monoclonal antibodies, recombinant antibodies, chimeric antibodies, human antibodies, and humanized antibodies, as well as antigen-binding fragments of the foregoing.

Monoclonal antibodies can be produced by a variety of techniques, including conventional monoclonal antibody methodology, e.g., the standard somatic cell hybridization technique of Kohler and Milstein, Nature 256: 495, 1975. Polyclonal antibodies can be produced by immunization of animal or human subjects. See generally, Harlow, E. and Lane, D. *Antibodies: A Laboratory Manual, Cold Spring Harbor Laboratory Press, Cold Spring Harbor, N.Y.,* 1988. Antibodies against AR described herein can be used, e.g., for diagnostic assays, or for therapeutic applications.

RNAi

Inhibitory nucleic acids are well known in the art. For example, siRNA, shRNA and double-stranded RNA have been described in U.S. Pat. Nos. 6,506,559 and 6,573,099, as well as in U.S. Patent Publications 2003/0051263, 2003/0055020, 2004/0265839, 2002/0168707, 2003/0159161, and 2004/0064842, all of which are herein incorporated by reference in their entirety.

RNA interference refers to sequence-specific inhibition of gene expression and/or reduction in target RNA levels mediated by an at least partly double-stranded RNA, which RNA comprises a portion that is substantially complementary to a target RNA. Typically, at least part of the substantially complementary portion is within the double stranded region of the RNA. In some embodiments, RNAi can occur via selective intracellular degradation of RNA. In some embodiments, RNAi can occur by translational repression. In some embodiments, RNAi agents mediate inhibition of gene expression by causing degradation of target transcripts. In some embodiments, RNAi agents mediate inhibition of gene expression by inhibiting translation of target transcripts. Generally, an RNAi agent includes a portion that is substantially complementary to a target RNA. In some embodiments, RNAi agents are at least partly double-stranded. In some embodiments, RNAi agents are single-stranded. In some embodiments, exemplary RNAi agents can include small interfering RNA (siRNA), short hairpin RNA (shRNA), and/or microRNA (miRNA). In some embodiments, an agent that mediates RNAi includes a blunt-ended (i.e., without overhangs) dsRNA that can act as a Dicer substrate. For example, such an RNAi agent may comprise a blunt-ended dsRNA which is >25 base pairs length. RNAi mechanisms and the structure of various RNA molecules known to mediate RNAi, e.g. siRNA, shRNA, miRNA and their precursors, are described, e.g., in Dykxhhorn et al., 2003, Nat. Rev. Mol. Cell. Biol., 4:457; Hannon and Rossi, 2004, Nature, 431:3761; and Meister and Tuschl, 2004, Nature, 431:343; all of which are incorporated herein by reference.

An inhibitory nucleic acid may inhibit the transcription of a gene or prevent the translation of a gene transcript in a cell. An inhibitory nucleic acid may be from 16 to 1000 nucleotides long, and in certain embodiments from 18 to 100 nucleotides long. In certain embodiments, the inhibitory nucleic acid is an isolated nucleic acid that binds or hybridizes to a nucleotide sequence such as the AR coding sequence of SEQ ID NO: 2. In some embodiments, An siRNA or antisense oligonucleotide that is specifically hybridizable to an mRNA encoding an androgen receptor polypeptide whose amino acid sequence shows at least 60% (e.g., at least 65%, 70%, 75%, 80%, 85%, 90%, 95%, or 98%) overall sequence identity with a reference wild type androgen receptor polypeptide of SEQ ID NO 1, which polypeptide includes a residue corresponding to residue 876, which corresponding residue is not leucine but is not specifically hybridizable to an mRNA encoding to an androgen receptor polypeptide whose amino acid sequence shows at least 60% (e.g., at least 65%, 70%, 75%, 80%, 85%, 90%, 95%, or 98%) overall sequence identity with a reference wild type androgen receptor polypeptide of SEQ ID NO 1, which polypeptide includes a residue corresponding to residue 876, which corresponding residue is leucine. In certain embodiments, the inhibitory nucleic acid is an isolated nucleic acid that binds or hybridizes to a nucleotide sequence encoding the novel AR polypeptide fragments thereof, e.g., an AR F876C polypeptide, an AR F876I polypeptide, an AR F876L polypeptide, an AR F876S polypeptide, an AR F876V polypeptide, and/or an AR F876Y polypeptide.

In some embodiments, An siRNA or antisense oligonucleotide that is specifically hybridizable to an mRNA encoding an androgen receptor polypeptide whose amino acid sequence shows at least 60% (e.g., at least 65%, 70%, 75%, 80%, 85%, 90%, 95%, or 98%) overall sequence identity with a reference wild type androgen receptor polypeptide of SEQ ID NO 1, which polypeptide includes a mutation selected from E565K, E588K, S647G, E668K, C686Y, D695E, A699T, R726H, N727I, N771S, H776Y, C784R, and/or K910E but is not specifically hybridizable to an mRNA encoding to an androgen receptor polypeptide whose amino acid sequence shows at least 60% (e.g., at least 65%, 70%, 75%, 80%, 85%, 90%, 95%, or 98%) overall sequence identity with a reference wild type androgen receptor polypeptide of SEQ ID NO 1, which polypeptide includes a residue corresponding to the wild type residue at the selected mutation.

AR Mutant Detection

In certain embodiments, the present invention comprises a method of identifying an elevated risk or incidence of CRPC comprising providing a sample from an individual whose risk or incidence of CRPC is to be identified or characterized, processing the sample to detect a presence, level, or activity of an androgen receptor or portion thereof, and classifying the individual as having an elevated risk or incidence of CRPC if the determined presence, level, or activity correlates with incidence of castration resistant prostate cancer In some embodiments, the determined presence, level, or activity that correlates with incidence of castration resistant prostate cancer is an increased transcriptional activity at AR regulated promoters as described herein. In some embodiments, the determined presence, level, or activity that correlates with incidence or level of castration resistant prostate cancer is a presence or level of a mutant polypeptide sequence or fragment thereof. In some embodiments, the determined presence, level, or activity that correlates with incidence of castration resistant prostate cancer is a presence or level of a mutant AR gene sequence or fragment thereof.

In some embodiments, an individual is a non-human animal. In some embodiments, a non-human animal is a mouse. In some embodiments, a non-human animal is a rat. In some embodiments, a non-human animal is a dog. In some embodiments, a non-human animal is a non-human primate. In some embodiments, an individual is a human. In some embodiments, an individual is a human with prostate cancer.

In some embodiments, an elevated risk of CRPC comprises a risk of incidence that is 1, 2, 3, 4, 5, 6, 7, 8, 9, 10, 15, 20, 25, 30, 35, 40, 45, 50, 55, 60, 65, 70, 75, 80, 85, 90, 95, 100, 1000% or more higher than a reference level. In some embodiments, the reference level is an average occurrence of CRPC observed in a population.

In some embodiments, a sample is any sample comprising an AR polypeptide or nucleic acid. In some embodiments, a sample comprises cells from which DNA (e.g., genomic DNA) or RNA (e.g., pre-mRNA or mRNA) is or can be obtained. In some embodiments, a sample comprises isolated nucleic acids. In some embodiments, a sample comprises RNA. In some embodiments, a sample comprises cDNA. In some embodiments, a sample comprises DNA. In some embodiments, a sample comprises genomic DNA. In some embodiments, a sample comprises human genomic DNA.

In some embodiments, a sample is obtained from an individual harboring an AR mutation. In some embodiments, a sample is obtained from an individual harboring an androgen resistant AR. In some embodiments, a sample is obtained from an individual whose AR gene includes the sequence element FXXLF.

In some embodiments, processing a sample comprises isolating nucleic acids and/or polypeptides from cells in a sample. Methods of isolating DNA and RNA are well known in the art. Examples of methods for isolating DNA include but are not limited to phenol-chloroform extraction and a wide variety of commercially available kits, including QIAamp DNA Mini Kit (Qiagen, Valencia, Calif.). Examples of methods for isolating RNA include guanidinium isothiocyanate-ultracentrifugation isolation, guanidinium and phenol-chloroform isolation, lithium chloride-SDS-urea isolation or poly A+/mRNA isolation from tissue lysates using oligo(dT) cellulose. Methods of quantifying protein levels are well known in the art and include but are not limited to western analysis and mass spectrometry. (Ausubel F M, Brent R, Kingston R E, Moore D D, Seidman J G, Smith J A, Struhl K (eds). 1998. *Current Protocols in Molecular Biology*. Wiley: New York)

In some embodiments, processing a sample comprises determining a sequence or level of an AR polypeptide or portion thereof. In some embodiments, processing a sample comprises immunological methods. In some embodiments, processing a sample comprises contacting a sample with an anti-AR antibody described herein that discriminates between androgen receptors containing mutations that correlate with incidence of CRPC as compared with the reference androgen receptor. In some embodiments, the mutations comprise the mutations in the AR described herein. In some embodiments the reference AR polypeptide comprises the reference AR polypeptide described herein.

In some embodiments, an individual is classified as having an elevated risk or incidence of CRPC if antibody-antigen binding is increased in the individual whose risk or incidence of CRPC is to be identified or characterized relative to antibody-antigen interaction in a reference. In some embodiments an individual is classified as having an elevated risk or incidence of CRPC if antibody-antigen binding is increased 1, 2, 3, 4, 5, 6, 7, 8, 9, 10, 15, 20, 25, 30, 35, 40, 45, 50, 55, 60, 65, 70, 75, 80, 85, 90, 95, 100% or more relative to a reference. In some embodiments, a reference is a sample comprising a wild type AR polypeptide or fragment thereof. In some embodiments, a reference is a sample from an individual without CRPC. In some embodiments, a reference is a sample from an individual without prostate cancer. In some embodiments, a reference is a sample from an individual known to have a wild type AR polypeptide sequence. In some embodiments a reference antibody-antigen interaction level is determined. In some embodiments a reference antibody-antigen interaction level is determined concurrently with the determined antibody-antigen interaction level. In some embodiments, a reference antibody-antigen interaction level is determined historically relative to the determined antibody-antigen interaction level.

A number of methods for measuring antibody-antigen binding are known in the art, including ELISA (enzyme-linked immunosorbent assay), Western blotting, competition assay, immunoprecipitation, immunohistochemistry, and spot-blot. The detection step may be, for instance, chemiluminescent, fluorescent, or colorimetric.

In some embodiments, processing comprises processing to detect a sequence of an androgen receptor gene or fragment thereof. In some embodiments, processing a sample comprises amplifying a target nucleic acid region of human genomic DNA encompassing region of the AR polypeptide comprising the mutation. In some embodiments, amplifying comprises contacting the human genomic DNA with a 5' primer under conditions such that hybridization and extension of the target nucleic acid region occur in a forward direction. In some embodiments, amplifying further comprises contacting the human genomic DNA with a 3' primer under conditions such that hybridization and extension of the target nucleic acid region occur in a reverse direction.

Nucleic acid amplification methods are well known in the art and include, but are not limited to, the Polymerase Chain Reaction (or PCR, described, for example, in U.S. Pat. Nos. 4,683,195, 4,683,202 and 4,889,818, each of which is incorporated herein by reference in its entirety); and reverse transcriptase polymerase chain reaction (or RT-PCR, described in, for example, U.S. Pat. Nos. 5,322,770 and 5,310,652). In its simplest form, PCR is an in vitro method for the enzymatic synthesis of specific DNA sequences, using two primers that hybridize to opposite strands and flank the region of interest in the target DNA. A plurality of reaction cycles, each cycle comprising: a denaturation step, an annealing step, and a polymerization step, results in the exponential accumulation of a specific DNA fragment. The termini of the amplified fragments are defined as the 5' ends of the primers. Examples of DNA polymerases capable of producing amplification products in PCR reactions include, but are not limited to: *E. coli* DNA polymerase I, Klenow fragment of DNA polymerase I, T4 DNA polymerase, thermostable DNA polymerases isolated from *Thermus aquaticus* (Taq) which are available from a variety of sources (for example, Perkin Elmer), *Thermus thermophilus* (United States Biochemicals), *Bacillus stereothermophilus* (Bio-Rad), or *Thermococcus litoralis* ("Vent" polymerase, New England Biolabs). RNA target sequences may be amplified by reverse transcribing the mRNA into cDNA, and then performing PCR (RT-PCR), as described above. Alternatively, a single enzyme may be used for both steps as described in U.S. Pat. No. 5,322,770.

In some embodiments, processing a sample comprises genotyping a nucleic acid (e.g., an amplified nucleic acid). In some embodiments, an individual is classified as having an elevated risk or incidence of CRPC if they are determined by genotyping to have one or more mutant alleles. In some embodiments, mutant alleles comprise gene sequence encoding an AR mutation whose presence and/or level correlates with incidence and/or risk of CRPC. In some embodiments, the AR mutant alleles encodes a mutation in F876. In some embodiments, the AR mutation encodes a F876C, F876I, F876L, F876S, F876V or F876Y mutation. In some embodiments, the AR mutation encodes a E565K, E588K, S647G, E668K, C686Y, D695E, A699T, R726H, N727I, N771S, H776Y, C784R, and/or K910E mutation.

Common genotyping methods are known in the art and include, but are not limited to, quantitative PCR, molecular beacon assays, nucleic acid arrays, allele-specific primer extension, allele-specific PCR, arrayed primer extension, homogeneous primer extension assays, primer extension with detection by mass spectrometry, pyrosequencing, multiplex primer extension sorted on genetic arrays, ligation with rolling circle amplification, homogeneous ligation, OLA, multiplex ligation reaction sorted on genetic arrays, restriction-fragment length polymorphism, single base extension-tag assays, and the Invader assay. Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection.

In some embodiments genotyping a nucleic acid sample comprises a primer extension reaction. Several such methods have been described in the patent and scientific literature and include the "Genetic Bit Analysis" method (WO92/15712) and the ligase/polymerase mediated genetic bit analysis (U.S. Pat. No. 5,679,524). Related methods are disclosed in WO91/02087, WO90/09455, WO95/17676, U.S. Pat. Nos. 5,302,509, and 5,945,283. In some embodiments a primer extension reaction comprises contacting the amplified nucleic acid with one or more primers which specifically hybridize to a region of the isolated nucleic acid containing a mutation, and amplifying the hybridized amplified nucleic acid to detect the nucleotide present at the position of interest. In some embodiments detecting the presence or absence of an amplification product (assays can be designed so that hybridization and/or amplification will only occur if a particular mutation is present or absent).

In some embodiments, genotyping a nucleic acid sample comprises hybridizing a nucleic acid probe to the amplified human genomic DNA, wherein the nucleic acid probe comprises sequence that is complimentary to the sequence of the at least one mutation. In some embodiments, hybridization of the nucleic acid probe to the amplified human genomic DNA is detected by quantitative PCR. "Quantitative" PCR which are also referred to as "real-time PCR" and "real-time RT-PCR," respectively, involves detecting PCR products via a probe that provides a signal (typically a fluorescent signal) that is related to the amount of amplified product in the sample. Examples of commonly used probes used in quantitative include the following probes: TAQMAN® probes, Molecular Beacons probes, SCORPION® probes, and SYBR® Green probes. Briefly, TAQMAN® probes, Molecular Beacons, and SCORPION® probes each have a fluorescent reporter dye (also called a "fluor") attached on or around the 5' end of the probes and a quencher moiety attached on or around the 3' end of the probes. In the unhybridized state, the proximity of the fluor and the quench molecules prevents the detection of fluorescent signal from the probe. During PCR, when the polymerase replicates a template on which a probe is bound, the 5'-nuclease activity of the polymerase cleaves the probe at a site between the fluor and quencher thus, increasing fluorescence with each replication cycle. SYBR® Green probes bind double-stranded DNA and upon excitation emit light; thus as PCR product accumulates, fluorescence increases.

In some embodiments genotyping a nucleic acid sample comprises sequencing the amplified human genomic DNA. In some embodiments, any of a variety of sequencing reactions known in the art can be used to directly sequence at least a portion of amplified DNA. Exemplary sequencing reactions include those based on techniques developed by Maxam and Gilbert, *Proc. Natl. Acad. Sci USA*, 74:560 (1977) or Sanger, *Proc. Nat. Acad. Sci* 74:5463 (1977). It is also contemplated that any of a variety of automated sequencing procedures may be utilized when performing the subject assays, e.g., see Venter et al., *Science*, 291:1304-1351 (2001); Lander et al., Nature, 409:860-921 (2001), including sequencing by mass spectrometry, e.g., see U.S. Pat. No. 5,547,835 and PCT Patent Publication No. WO 94/16101 and WO 94/21822; U.S. Pat. No. 5,605,798 and PCT Patent Application No. PCT/US96/03651; Cohen et al., *Adv. Chromatogr.* 36:127-162 (1996); and Griffin et al., *Appl. Biochem. Biotechnol.* 38:147-159 (1993). It will be evident to one skilled in the art that, for some embodiments, the occurrence of only one, two or three of the nucleic acid bases need be determined in the sequencing reaction. Yet other sequencing methods are disclosed, e.g., in U.S. Pat. Nos. 5,580,732; 5,571,676; 4,863,849; 5,302,509; PCT Patent Application Nos. WO 91/06678 and WO 93/21340; Canard et al., Gene 148:1-6 (1994); Metzker et al., *Nucleic Acids Research* 22:4259-4267 (1994) and U.S. Pat. Nos. 5,740,341 and 6,306,597. In some embodiments, sequencing reactions comprise deep sequencing.

In some embodiments genotyping a nucleic acid sample comprises the use of two oligonucleotide probes in an OLA (see, e.g., U.S. Pat. No. 4,988,617). In this method, one probe hybridizes to a segment of a target nucleic acid with its 3' most end aligned with the mutant site. A second probe hybridizes to an adjacent segment of the target nucleic acid molecule directly 3' to the first probe. The two juxtaposed probes hybridize to the target nucleic acid molecule, and are ligated in the presence of a linking agent such as a ligase if there is perfect complementarity between the 3' most nucleotide of the first probe with the mutant site. If there is a mismatch, ligation would not occur. After the reaction, the ligated probes are separated from the target nucleic acid molecule, and detected as indicators of the presence of a mutation.

In some embodiments, an individual is classified as having an elevated risk or incidence of CRPC if transcriptional activity at AR regulated promoters is increased in the individual whose risk or incidence of CRPC is to be identified or characterized relative to transcriptional activity at AR regulated promoters in a reference. In some embodiments an individual is classified as having an elevated risk or incidence of CRPC if transcriptional activity at AR regulated promoters is increased 1, 2, 3, 4, 5, 6, 7, 8, 9, 10, 15, 20, 25, 30, 35, 40, 45, 50, 55, 60, 65, 70, 75, 80, 85, 90, 95, 100% or more relative to a reference. In some embodiments, a reference is a sample comprising a wild type AR gene or fragment thereof. In some embodiments, a reference is a sample from an individual without CRPC. In some embodiments, a reference is a sample from an individual without prostate cancer. In some embodiments, a reference is a sample from an individual known to have a wild type AR gene. In some embodiments a reference transcriptional activity at AR regulated promoters is determined. In some embodiments a reference transcriptional activity at AR regulated promoters is determined concurrently with the determined transcriptional activity at AR regulated promoters. In some embodiments, transcriptional activity at AR regulated promoters is determined historically relative to the determined transcriptional activity at AR regulated promoters.

In some embodiments, a reporter is an AR target gene and levels of gene expression are directly assayed. Methods of quantifying levels of RNA transcripts are well known in the art and include but are not limited to northern analysis, semi-quantitative reverse transcriptase PCR, quantitative reverse transcriptase PCR, and microarray analysis. These and other basic RNA transcript detection procedures are described in Ausebel et al. (Ausubel F M, Brent R, Kingston R E, Moore D D, Seidman J G, Smith J A, Struhl K (eds). 1998. *Current Protocols in Molecular Biology*. Wiley: New York).

Patient Diagnosis

In some embodiments, the present invention provides technologies for identifying and/or characterizing individuals suffering from or susceptible to CRPC. In some such embodiments, the identifying and/or characterizing comprises detecting an AR mutant in a sample from the individual. In some embodiments, the identifying and/or characterizing comprises detecting an AR mutation whose presence and/or level correlates with incidence and/or risk of CRPC. In some embodiments, the AR mutation is a mutation in F876. In some embodiments, the AR mutation is a F876C, F876I, F876L, F876S, F876V or F876Y mutation. In some embodiments, the AR mutation is a E565K, E588K, S647G, E668K, C686Y, D695E, A699T, R726H, N727I, N771S, H776Y, C784R, and/or K910E mutation. Such detecting can be direct or indirect. For example, such detecting can involve determining level and/or activity of an AR polypeptide, of a nucleic acid encoding an AR polypeptide and/or of one or more downstream targets modulated by activity of an AR polypeptide as described herein.

In some embodiments, an AR mutant is detected by obtaining a sample from the individual to be tested and detecting presence/level, and/or activity of the AR mutant in the sample. In some embodiments, the presence or level of the AR mutant is a presence or level of a mutant polypeptide sequence or fragment thereof as described herein. In some embodiments, the presence or level of a mutant AR gene sequence or fragment thereof as described herein. In some embodiments, the activity of the AR mutant is a level of transcription of an AR regulated promoter as described herein.

In some embodiments provided methodologies for identifying and/or characterizing patients are used to select patients likely to be responsive or unresponsive to a particular therapy. In some embodiments, patients with AR mutations in F876 are unlikely to be responsive to antiandrogens. In some embodiments, patients with F876C, F876I, F876L, F876S, F876V or F876Y AR mutations are unlikely to be responsive to antiandrogens. In some embodiments, patients with E565K, E588K, S647G, E668K, C686Y, D695E, A699T, R726H, N727I, N771S, H776Y, C784R, and/or K910E AR mutations are unlikely to be responsive to antiandrogens. In some embodiments, patients with AR mutations in F876 are likely to be responsive to agents described herein. In some embodiments, patients with F876C, F876I, F876L, F876S, F876V or F876Y AR mutations are likely to be responsive to agents described herein. In some embodiments, patients with E565K, E588K, S647G, E668K, C686Y, D695E, A699T, R726H, N727I, N771S, H776Y, C784R, and/or K910E AR mutations are likely to be responsive to agents described herein.

In some embodiments, the method further embodies revising the treatment. In some embodiments revising the treatment comprises discontinuing treatment with anti-androgens. In some embodiments, revising the treatment comprises administering a therapeutically effective amount of docetaxel. In some embodiments, revising the treatment comprises administering a therapeutically effective amount of sipuleucel-T. In some embodiments, revising the treatment comprises administering a therapeutically effective amount of cabazitaxel. In some embodiments, revising the treatment comprises administering a therapeutically effective amount of abiraterone acetate. In some embodiments, revising the treatment comprises administering a therapeutically effective amount of denosumab. Methods for administering docetaxel, sipuleucel-T, cabazitaxel, abiraterone acetate, and denosumab as a treatment for CRPC are known in the art, as shown, for example, by Felici et al. in "A changing landscape in castration-resistant prostate cancer treatment," (Front Endocrinol (Lausanne). 2012; 3:85). In some embodiments, revising the treatment comprises administering a novel treatment for CRPC according to the methods described herein.

In some embodiments revising the treatment comprises administering a treatment that reduces tumor volume by 1, 2, 3, 4, 5, 6, 7, 8, 9, 10, 15, 20, 25, 30, 35, 40, 45, 50, 55, 60, 65, 70, 75, 80, 85, 90, 95, 100% or more.

Patient Population Stratification

Identifying and/or characterizing AR mutations in patient populations, as described herein can be used as biomarkers alone or in combination, or alternatively, together with clinical diagnostic markers, such as tumor size, to stratify patients based on severity of prostate cancer, selecting proper therapy or dosing regimen, evaluating the effectiveness of a therapy, monitoring responsiveness to therapy, prognosis for disease course, and measurement of disease progression in a subject. Typically, in such methods, levels of suitable biomarkers (e.g., such as those selected from various differentially expressed AR regulated genes such as probasin or presence of AR mutations described herein) determined for a biological sample obtained from the subject from one or more time points are compared to the levels from the subject from one or more other time points. For example, biomarker levels may be measured before or at the beginning of a treatment course. Biomarker levels may be measured at one or more time points throughout the course of treatment and compared with the level before the treatment or from an earlier time point of a treatment course.

Identification or selection of appropriate treatment, determining if a patient has positive response to a treatment and/or optimization of the treatment can be determined based on the evaluation of biomarkers.

New Mutant Identification

Among other things, the present invention identifies and/or characterizes one or more AR alleles or mutants whose presence correlates with incidence of particular diseases, disorders, or conditions. In some embodiments, identifying alleles whose presence correlates with incidence of particular diseases, disorders, or condition comprises identifying alleles whose presence correlates with incidence of CRPC. In some embodiments, identifying alleles whose presence correlates with incidence of CRPC comprises identifying alleles correlated with increased transcription from AR activated promoter in the presence of antiandrogens. In some embodiments, identifying alleles whose presence correlates with incidence of CRPC comprises identifying alleles correlated with increased tumor cell growth in the presence of antiandrogens.

The present invention encompasses the recognition that identification of mutations in the AR polypeptide that correlate with increased transcriptional activation of AR target genes in the presence of antiandrogens is potentially useful in identifying novel mutations causing incidence or increased risk of CRPC. In some embodiments, methods of the current invention comprise providing a population of cells comprising a library of androgen receptor polypeptides each of which shares at least X % overall sequence identity with a single parent androgen receptor polypeptide and a reporter, contacting the population of cells with an antiandrogen, detecting expression of the reporter, and classifying cells as antiandrogen resistant androgen receptor mutants if expression of the reporter is increased. In some embodiments, X comprises 1, 2, 3, 4, 5, 6, 7, 8, 9, 10, 15, 20, 25, 30, 35, 40, 45, 50, 55, 60, 65, 70, 75, 80, 85, 90, 95 up to 100% sequence identity.

In some embodiments, a library of AR comprises a library of plasmids encoding the AR polypeptides. In some embodiments, a library of plasmids is generated by mutagenesis from a single plasmid containing an AR polypeptide as described herein. In some embodiments, mutagenesis comprises random mutagenesis. Techniques for site directed mutagenesis are well known in the art and are described in described in Ausebel et al. (Ausubel F M, Brent R, Kingston R E, Moore D D, Seidman J G, Smith J A, Struhl K (eds). 1998. *Current Protocols in Molecular Biology*. Wiley: New York).

In some embodiments, a library of AR polypeptides and a reporter are transformed or transfected into cultured cells using methods described herein. In some embodiments, cultured cells comprise any cell type capable of expressing AR. In some embodiments, cultured cells comprise human cell lines. In some embodiments, cultured cells comprise mouse cell lines. In some embodiments, cultured cells comprise human prostate adenocarcinoma cells. In some embodiments, cultured cells comprise LNCaP/AR cells. In some embodiments, cultured cells comprise CWR22PC cells. In some embodiments, cultured cells comprise CV1 cells. In some embodiments, cultured cells comprise VCaP cells.

In some embodiments, contacting the population of cells with an antiandrogen comprises contacting cells with any antiandrogen that inhibits AR activity, as described herein. In some embodiments, contacting the population of cells with an antiandrogen comprises contacting the population of cells with flutamide. In some embodiments, contacting the population of cells with an antiandrogen comprises contacting the population of cells with nilutamide. In some embodiments, contacting the population of cells with an antiandrogen comprises contacting the population of cells with bicalutamide. In some embodiments, contacting the population of cells with an antiandrogen comprises contacting the population of cells with megestrol. In some embodiments, contacting the population of cells with an antiandrogen comprises contacting the population of cells with ARN-509. In some embodiments, contacting the population of cells with an antiandrogen comprises contacting the population of cells with enzalutamide. In some embodiments, contacting the population of cells with antiandrogens comprises contacting the cells with 0.001, 0.01, 0.1, 1, 10, 100, 1000 or more µM antiandrogens. In some embodiments, contacting the population of cells with antiandrogens comprises contacting the cells with antiandrogens for 1, 2, 3, 4, 5, 6, 7, 8, 9, 10 or more days.

Techniques for culturing a wide variety of cell types are well known in the art. See, for example, Current Protocols in Molecular Biology (N.Y., John Wiley & Sons; Davis et al. 1986). Cell culture media utilized in accordance with the present invention is or comprises serum-free cell culture media. In certain embodiments, utilized cell culture media is fully defined synthetic cell culture media. In some embodiments, utilized cell culture media is Roswell Park Memorial Institute medium (RPMI). In certain embodiments, utilized cell culture media is Dulbecco's Modified Eagle Medium (DMEM). In certain embodiments, utilized cell culture media is Iscove's Modified Dulbecco's Medium (IMEM). In certain embodiments, utilized cell culture media is RPMI, Ham's F-12, or Mammary Epithelial Cell Growth Media (MEGM). In some embodiments, cell culture media comprises additional components including Fetal Bovine Serum (FBS), charcoal-stripped, dextran-treated fetal bovine serum (CSS), Bovine Serum (BS), and/or Glutamine or combinations thereof. In some embodiments, utilized media are supplemented with an antibiotic to prevent contamination. Useful antibiotics in such circumstances include, for example, penicillin, streptomycin, and/or gentamicin and combinations thereof. Those of skill in the art are familiar with parameters relevant to selection of appropriate cell culture media.

A reporter gene construct is a nucleic acid molecule that includes a nucleic acid encoding a reporter operatively linked to a transcriptional control sequences. Transcription of the reporter gene is controlled by these sequences. Activity of at least one or more of these control sequences is directly or indirectly regulated by transcription factors and other proteins or biomolecules. Transcriptional control sequences include a promoter and other regulatory regions, such as enhancer sequences, that modulate activity of the promoter, or control sequences that modulate activity or efficiency of RNA polymerase that recognizes the promoter, or control sequences are recognized by effector molecules. Such sequences are herein collectively referred to as transcriptional regulatory elements or sequences.

In some embodiments, transcriptional control sequences comprise enhancer elements. In some embodiments, enhancer elements bind AR polypeptide. In some embodiments, enhancer elements are prostate specific antigen enhancer elements.

In some embodiments, transcriptional control sequences comprises a promoter for a gene regulated by AR polypeptide. In some embodiments, the promoter comprises a promoter for a gene transcriptionally activated by AR polypeptide. In some embodiments, the promoter comprises a probasin promoter. In some embodiments, the promoter comprises a PSA promoter. In some embodiments, the promoter comprises a Tmprss2 promoter. In some embodiments, the promoter comprises a SGK1 promoter. In some embodiments, the promoter comprises a FKBP5 promoter.

A reporter refers to any entity that allows for detection of a molecule of interest, such as a protein expressed by a cell, or a biological particle. Typical reporter entities include, include, for example, light emitting proteins such as luciferase, fluorescent proteins, such as red, blue and green fluorescent proteins (see, e.g., U.S. Pat. No. 6,232,107, which provides GFPs from Renilla species and other species), lacZ gene from E. coli, alkaline phosphatase, secreted embryonic alkaline phosphatase (SEAP), chloramphenicol acetyl transferase (CAT), hormones and cytokines and other such well-known genes. For expression in cells, nucleic acid encoding a reporter entity can be expressed as a fusion protein with a protein of interest or under control of a promoter of interest. Expression of these reporter genes can also be monitored by measuring levels of mRNA transcribed from these genes. Techniques for assessing activity level of enhancers using reporter genes are well known in the art. In some embodiments, reporter gene protein levels are assayed through ELISA, western blot, FACS, MACS, flow cytometry, β-galactosidase assays and/or immunohistochemistry.

Reporter gene constructs may be or include any vector that facilitates expression of a reporter sequence in a construct in a host cell. Any suitable vector can be used as described herein.

In some embodiments, contacting the cells with an antiandrogen results in transcriptional activation of the reporter. In some embodiments, transcription of the reporter is activated 1.1, 1.2, 1.3, 1.4, 1.5, 1.6, 1.7, 1.8, 1.9, 2, 3, 4, 5, 6, 7, 8, 9, 10, 20, 30, 40, 50, 60, 70, 80, 90, 100, 200, 300, 400, 500, 600, 700, 800, 900, 1000, or 10,000 fold or more relative to a reference AR activation level.

In some embodiments a reference AR activation level is determined concurrently with the determined AR activation level. In some embodiments, a reference AR activation level is determined historically relative to the determined AR activation level. In some embodiments, a reference AR activation level comprises an AR activation level that is observed in the system or a comparable system under identical or otherwise comparable conditions lacking the antiandrogen. In some embodiments, a reference AR activation level comprises the AR activation level that is observed in the system or a comparable system under comparable or otherwise identical conditions with a wild type AR polypeptide or fragment thereof. In some embodiments, a reference AR activation level comprises the AR activation level that is observed in the system or a comparable system under comparable otherwise identical conditions without an AR polypeptide. In some embodiments, a reference AR activation level comprises the AR activation level that is observed in the system or a comparable system under comparable or otherwise identical conditions without a reporter. In some embodiments, a reference AR activation level comprises the AR activation level that is observed in the system or a comparable system under comparable or otherwise identical conditions without a reporter or an AR polypeptide.

The present invention further encompasses the recognition that identification of mutations in the AR polypeptide that correlate with increased cellular growth rate during antiandrogen treatment is potentially useful in identifying novel mutations causing incidence or increased risk of CRPC. In some embodiments, the methods of the current invention comprise contacting a population of cells with an antiandrogen until an increase in growth rate occurs, classifying cells as antiandrogen resistant androgen receptor mutants once an increase in growth rate occurs, and processing the cells to detect a sequence of an androgen receptor or portion thereof The population of cells may comprise any suitable cell type as described herein. In some embodiments, the cells are mouse cells. In some embodiments, the cells are primate cells. In some embodiments, the cells are human cells. In some embodiments, the cells are allogeneic cells. In some embodiments, the cells express AR. In some embodiments, the cells are prostate cancer tumor cells. In some embodiments, the cells are LNCaP/AR cells. In some embodiments, the cells are CWR22Pc cells. In some embodiments, the cells are negative control cells not expressing AR.

In some embodiments, the population of cells comprises cells cultured vivo using cell culture techniques described herein. In some embodiments, an increase in growth rate comprises a decrease in cellular doubling time. In some embodiments, an increase in growth rate comprises a decrease in time to confluence in cell culture. In some embodiments, an increase in growth rate comprises a decrease in time to confluence of 1.1, 1.2, 1.3, 1.4, 1.5, 1.6, 1.7, 1.8, 1.9, 2 fold or more relative to time to confluence before treatment with antiandrogen. Confluence is the point at which adherent cells in a plate of cultured cells have substantially covered a plate bottom. In some embodiments, confluence is reached when cells cover 30%, at least 40%, at least 50%, at least 60%, at least 70%, at least 80%, at least 90%, at least 95%, or substantially 100% of the bottom of the cell culture plate.

Exemplary methods for identification of AR mutants conferring resistance to antiandrogens are described in example 2.

In some embodiments, the population of cells comprises cells are cultured vivo. In some embodiments, the population of cells is contained within an animal model. In some embodiments, the animal model is a mouse model. In some embodiments, the animal model is a rat model. In some embodiments, the animal model is a non-human primate model. In some embodiments the animal model is a model for CRPC. In some embodiments, the population of cells comprises autologous cells within the animal model. In some embodiments, the population of cells comprises allogeneic cells within the animal model. In some embodiments, the population of cells within the animal model associates to form a solid tumor.

In some embodiments, an increase in growth rate in an animal model comprises an increase in tumor size. In some embodiments, tumor size increases by 1.1, 1.2, 1.3, 1.4, 1.5, 1.6, 1.7, 1.8, 1.9, 2, 3, 4, 5, 6, 7, 8, 9, 10 fold or more relative to tumor size before treatment with antiandrogen. One example of an animal model for CRPC is the castrated mouse model shown in example 1.

In some embodiments, processing the cells comprises any mode of genotyping cells described herein.

Use

Test Agents

The present disclosure provides assays for identifying and/or characterizing one or more agents to evaluate an effect of the test agent on level or activity of an AR polypeptide. In some embodiments, AR mutation is correlated with incidence and/or risk of CRPC. In some embodiments, the AR mutation is a mutation in F876. In some embodiments, the AR mutation is a F876C, F876I, F876L, F876S, F876V or F876Y mutation. In some embodiments, the AR mutation is a E565K, E588K, S647G, E668K, C686Y, D695E, A699T, R726H, N727I, N771S, H776Y, C784R, and/or K910E mutation.

A test agent can be any chemical compound, for example, a macromolecule (e.g., a polypeptide, a protein complex, or a nucleic acid) or a small molecule (e.g., an amino acid, a nucleotide, or an organic or inorganic compound). The test agent can have a formula weight of less than about 10,000 grams per mole, less than 5,000 grams per mole, less than 1,000 grams per mole, or less than about 500 grams per mole, e.g., between 5,000 to 500 grams per mole. The test agent can be naturally occurring (e.g., a herb or a nature product), synthetic, or both. Examples of macromolecules are proteins (e.g., antibodies, antibody fragments), protein complexes, and glycoproteins, nucleic acids, e.g., DNA, RNA (e.g., siRNA), and PNA (peptide nucleic acid). Examples of small molecules are peptides, peptidomimetics (e.g., peptoids), amino acids, amino acid analogs, polynucleotides, polynucleotide analogs, nucleotides, nucleotide analogs, organic or inorganic compounds e.g., heteroorganic or organometallic compounds.

In certain embodiments, the test agent is an antibody or antibody fragment (e.g., diabody) directed to AR polypeptide. The antibody or antibody fragment may be directed to any region of the AR polypeptide. The antibody may be polyclonal or monoclonal. The antibody may be of any isotype. The antibody may be derived from any species; however, for use in humans, the antibody is typically of human origin or has been humanized. If the antibody is to be used in other species, the antibody may be adapted to that species. In certain embodiments, the antibody is a humanized monoclonal antibody. In certain specific embodiments, the antibody is a wholly human monoclonal antibody. Techniques for engineering and preparing antibodies are known in the art and are described in U.S. Pat. No. 4,816,567, issued Mar. 28, 1989; U.S. Pat. No. 5,078,998, issued Jan. 7, 1992; U.S. Pat. No. 5,091,513, issued Feb. 25, 1992; U.S. Pat. No. 5,225,539, issued Jul. 6, 1993; U.S. Pat. No. 5,585,089, issued Dec. 17, 1996; U.S. Pat. No. 5,693,761, issued Dec. 2, 1997; U.S. Pat. No. 5,693,762, issued Dec. 2, 1997; U.S. Pat. No. 5,869,619; issued 1991; U.S. Pat. No. 6,180,370, issued Jan. 30, 2001; U.S. Pat. No. 6,548,640, issued Apr. 15, 2003; U.S. Pat. No. 6,881,557, issued Apr. 19, 2005; U.S. Pat. No. 6,982,321, issued Jan. 3, 2006; incorporated herein by reference.

In some embodiments test agents are identified by chemical modeling. In certain other embodiments, the test agent may be a protein, peptide, or small molecule that mimics an antigen binding site of an antibody directed to an AR polypeptide. These agents may be designed or identified in silico based on the structure of the antigen binding site of the antibody directed to AR polypeptide. The agents may then be tested in various in vitro assays to assess the ability of the agent to inhibit AR polypeptide. The agents may also be identified using high-throughput screening methods using libraries of small molecules, peptides, or polynucleotides.

In certain embodiments, a test agent is a nucleic acid molecule, e.g., DNA or RNA. In some embodiments, a nucleic acid molecule mediates RNA interference as described herein.

In some embodiments, a test agent is the only substance assayed by a method described herein. In some embodiments, a collection of test agents are assayed either consecutively or concurrently by methods described herein. Members of a collection of test agents can be evaluated individually or in a pool, e.g., using a split-and-pool method.

In some embodiments, high throughput screening methods are used to screen a chemical or peptide library, or other collection, containing a large number of potential test compounds. Such chemical libraries" are then screened in one or more assays to identify those library members (particular chemical species or subclasses) that display a desired characteristic activity. Compounds thus identified can serve as conventional "lead compounds" or can themselves be used as potential or actual modulators (e.g., as therapeutics).

A chemical compound library typically includes a collection of diverse chemical compounds, for example, generated by either chemical synthesis or biological synthesis, by combining a number of chemical "building blocks" such as reagents. For example, a linear chemical library such as a polypeptide library may be formed by combining a set of chemical building blocks (amino acids), e.g., in particular specified arrangements or in every possible way for a given compound length (i.e., the number of amino acids in a polypeptide compound). Millions of chemical compounds can be synthesized through such combinatorial mixing of chemical building blocks.

Preparation and screening of libraries of chemical compounds or agents is well known to those of skill in the art. Such libraries include, but are not limited to, peptide libraries (see, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like). Additional examples of methods for the synthesis or preparation of compound libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and Gallop et al. (1994) J. Med. Chem. 37:1233.

Some exemplary libraries are used to generate variants from a particular lead compound. One method includes generating a combinatorial library in which one or more functional groups of the lead compound are varied, e.g., by derivatization. Thus, the combinatorial library can include a class of compounds which have a common structural feature (e.g., scaffold or framework).

Devices for the preparation of small molecule libraries (e.g., combinatorial libraries) are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous small molecule libraries are commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

Test agents can also be obtained from: biological libraries; peptoid libraries (libraries of molecules having the functionalities of peptides, but with a novel, non-peptide backbone which are resistant to enzymatic degradation but which nevertheless remain bioactive; see, e.g., Zuckermann, R. N. et al. (1994) J. Med. Chem. 37:2678-85); spatially addressable parallel solid phase or solution phase libraries; synthetic library methods requiring deconvolution; the 'one-bead one-compound' library method; synthetic library methods using affinity chromatography selection, or any other source, including assemblage of sets of compounds having a structure and/or suspected activity of interest. Biological libraries include libraries of nucleic acids and libraries of proteins. Some nucleic acid libraries provide, for example, functional RNA and DNA molecules such as nucleic acid aptamers or ribozymes. A peptoid library can be made to include structures similar to a peptide library. (See also Lam (1997) Anticancer Drug Des. 12:145). A library of proteins may be produced by an expression library or a display library (e.g., a phage display library).

Libraries of test agents may be presented in solution (e.g., Houghten (1992) Biotechniques 13:412-421), or on beads (Lam (1991) Nature 354:82-84), chips (Fodor (1993) Nature 364:555-556), bacteria (Ladner, U.S. Pat. No. 5,223,409), spores (Ladner U.S. Pat. No. 5,223,409), plasmids (Cull et al. (1992) Proc Natl Acad Sci USA 89:1865-1869) or on phage (Scott and Smith (1990) Science 249:386-390; Devlin (1990) Science 249:404-406; Cwirla et al. (1990) Proc. Natl. Acad. Sci. 87:6378-6382; Felici (1991) J. Mol. Biol. 222: 301-310; Ladner supra.).

Identifying Treatments

In some embodiments, the present invention provides technologies for identifying potential treatments for CRPC. For example, in accordance with the present invention, useful treatments modulate level and/or activity of one or more AR mutants. In some embodiments one or more AR mutants are selected any mutation at F876. In some embodiments one or more AR mutants are selected from F876C, F876I, F876L, F876S, F876V, and/or F876Y AR mutations. In some embodiments one or more AR mutants are selected from E565K, E588K, S647G, E668K, C686Y, D695E, A699T, R726H, N727I, N771S, H776Y, C784R, and/or K910E AR mutations.

In some embodiments, useful treatments decrease level of AR mutants. In some embodiments, useful treatments decrease transcriptional activity of AR mutants.

Any of a variety of assays can be used to assess AR activity. Techniques well known in the art include direct binding assays and competition assays. In some embodiments, AR activity is assessed by functional readout assay. In some embodiments, AR activity is assessed by transcriptional readout assays, as described herein.

The present invention encompasses the recognition that the level of AR transcriptional activation may correspond to risk or incidence of CRPC and that AR transcriptional activation can be relied upon to identify new agents for reducing the risk or incidence of CRPC.

In some embodiments, the current invention provides methods of identifying compounds for treating or reducing the risk of CRPC comprising providing a population of cells comprising an androgen receptor polypeptide containing a mutation that correlates with incidence of CRPC and an androgen receptor-activated reporter, contacting the population of cells with one or more test agents, detecting expression of the androgen receptor-activated reporter, and classifying test agents as treating or reducing the risk of CRPC if expression of the androgen receptor-activated reporter is decreased. In some embodiments, mutation that correlates with incidence of CRPC are described herein.

In accordance with methods of the present invention, test agents are contacted with the system described herein. Methods of contacting test agents to in vitro and in vivo systems are well known in the art. Methods of contacting test agents to in vitro systems include, but are not limited to, pipeting, mixing, or any other means of transferring a solid or liquid into cell culture or a cell free system. Methods of contacting test agents to in vivo systems include, but are not limited to direct administration to a target tissue, such as heart or muscle (e.g., intramuscular), tumor (intratumorally), nervous system (e.g., direct injection into the brain; intraventricularly; intrathecally). Alternatively, test agents can be administered by inhalation, parenterally, subcutaneously, intradermally, transdermally, or transmucosally (e.g., orally or nasally). More than one route can be used concurrently, if desired.

In some embodiments, detecting expression of the androgen receptor-activated reporter when the test agent is present comprises methods for detecting expression of the androgen receptor-activated reporter described herein.

In some embodiments a reference AR activation level is determined. In some embodiments a reference AR activation level is determined concurrently with the determined AR activation level. In some embodiments, a reference AR activation level is determined historically relative to the determined AR activation level. In some embodiments, a reference AR activation level comprises an AR activation level that is observed in the system or a comparable system under comparable conditions lacking the test agent. In some embodiments, a reference AR activation level comprises the AR activation level that is observed in the system or a comparable system under otherwise identical conditions lacking the test agent.

In some embodiments, a reference AR activation level comprises the AR activation level that is observed in the system or a comparable system under comparable conditions that includes presence of a positive control agent. In some embodiments, a positive control agent comprises an agent characterized in that level of AR activation is higher in an AR activation system when that system is contacted with the agent than under otherwise identical conditions when the system is not so contacted with the agent.

In some embodiments, a reference AR activation level comprises the AR activation level that is observed in the system or a comparable system under comparable conditions that include presence of a negative control agent. In some embodiments, a negative control agent comprises an agent characterized in that level of AR activation is lower in an AR activation system when that system is contacted with the agent than under otherwise identical conditions when the system is not so contacted with the agent. In some embodiments, a negative control agent comprises docetaxel. In some embodiments, a negative control agent comprises sipuleucel-T. In some embodiments, a negative control agent comprises cabazitaxel. In some embodiments, a negative control agent comprises abiraterone acetate. In some embodiments, a negative control agent comprises denosumab.

In some embodiments, the current invention provides methods of identifying agents for treating or reducing incidence or risk for CRPC comprising determining transcription levels of one or more targets of AR transcriptional activation contacted to a test agent and identifying the test agent as reducing incidence or risk for CRPC if the transcription levels are reduced relative to transcription levels in comparable conditions lacking the test agent.

Treatments for CRPC

The present invention encompasses the recognition that modulation of AR activity represents an effective therapy for CRPC. In some embodiments, the current invention provides methods of treating or reducing risk for CRPC comprising administering to a subject one or more AR transcriptional activation inhibitors. In some embodiments, the current invention provides methods of treating or reducing risk for CRPC comprising administering to a subject one or more agents characterized in that transcription levels of one or more targets of AR transcriptional activation are lower in the agent's presence as compared with in its absence.

In some embodiments, AR transcriptional activation inhibitors comprise agents characterized in that level AR transcriptional activation inhibitors is lower in an AR transcriptional activation system when that system is contacted with the agent than under otherwise identical conditions when the system is not so contacted with the agent. Novel agents for CRPC identified herein are shown in Table 2.

TABLE 2

| Compound ID | MSKCC Code | Compound Structure |
|---|---|---|
| I-1 | S-DR103 | 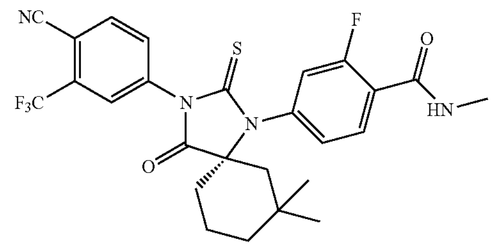 [SMILES: CNC(=O)c1ccc(N2C(=S)N(c3ccc(C#N)c(C(F)(F)F)c3)C(=O)[C@@]23CCCC(C)(C)C3)cc1F] |
| I-2 | R-DR103 | 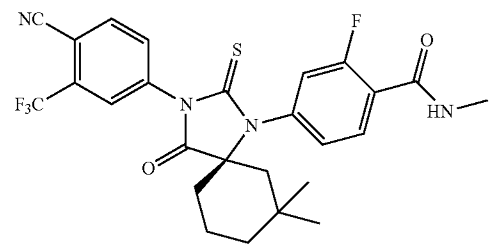 [SMILES: CNC(=O)c1ccc(N2C(=S)N(c3ccc(C#N)c(C(F)(F)F)c3)C(=O)[C@]23CCCC(C)(C)C3)cc1F] |
| I-3 | S-DR106 | 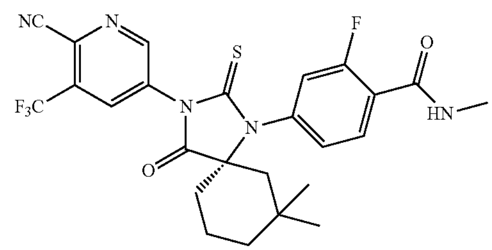 [SMILES: CNC(=O)c1ccc(N2C(=S)N(c3cnc(C#N)c(C(F)(F)F)c3)C(=O)[C@@]23CCCC(C)(C)C3)cc1F] |
| I-4 | R-DR106 | 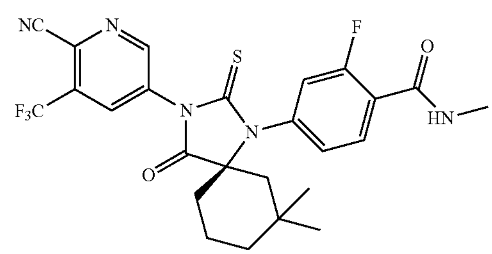 [SMILES: CNC(=O)c1ccc(N2C(=S)N(c3cnc(C#N)c(C(F)(F)F)c3)C(=O)[C@]23CCCC(C)(C)C3)cc1F] |

TABLE 2-continued

| Compound ID | MSKCC Code | Compound Structure |
|---|---|---|
| I-5 | DR105 | 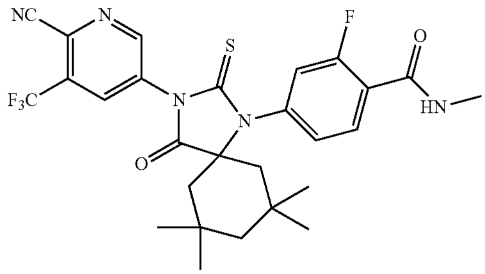 [SMILES: CNC(=O)c1ccc(N2C(=S)N(c3cnc(C#N)c(C(F)(F)F)c3)C(=O)C23CC(C)(C)CC(C)(C)C3)cc1F] |
| I-6 | DR115 | 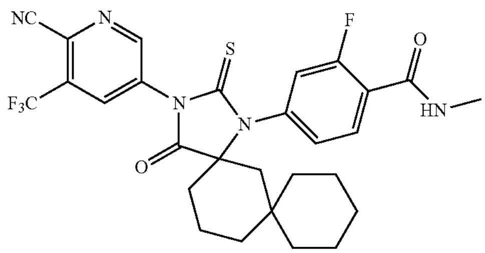 [SMILES: CNC(=O)c1ccc(N2C(=S)N(c3cnc(C#N)c(C(F)(F)F)c3)C(=O)C23CCCC2(CCCCC2)C3)cc1F] |
| I-7 | DR124 | 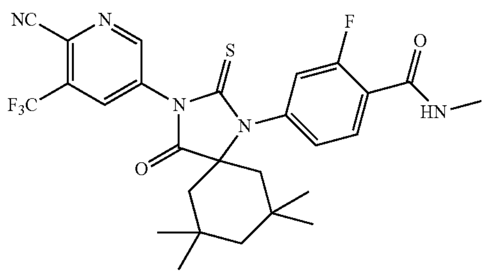 [SMILES: CNC(=O)c1ccc(N2C(=S)N(c3cnc(C#N)c(C(F)(F)F)c3)C(=O)C23CC(C)(C)CC(C)(C)C3)cc1F] |
| I-8 | DR100 | 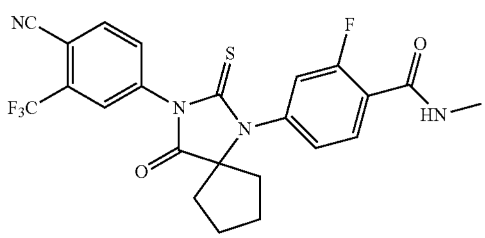 [SMILES: CNC(=O)c1ccc(N2C(=S)N(c3ccc(C#N)c(C(F)(F)F)c3)C(=O)C23CCCC3)cc1F] |
| I-9 | DR101 | 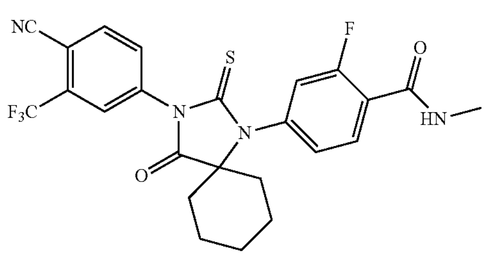 [SMILES: CNC(=O)c1ccc(N2C(=S)N(c3ccc(C#N)c(C(F)(F)F)c3)C(=O)C23CCCCC3)cc1F] |
| I-10 | DR102 | 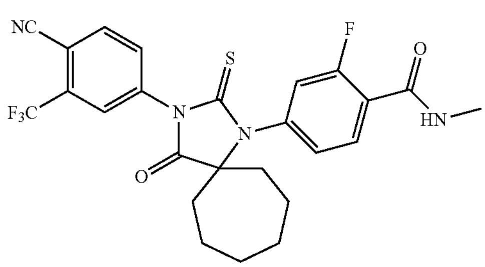 [SMILES: CNC(=O)c1ccc(N2C(=S)N(c3ccc(C#N)c(C(F)(F)F)c3)C(=O)C23CCCCCC3)cc1F] |

TABLE 2-continued

| Compound ID | MSKCC Code | Compound Structure |
|---|---|---|
| I-11 | DR104 | 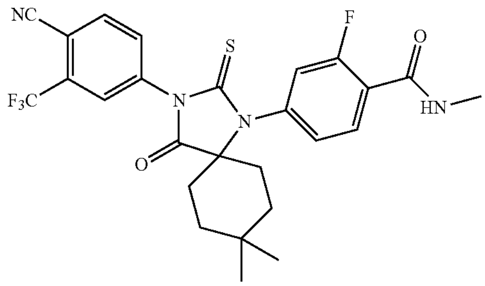 [SMILES: CNC(=O)c1ccc(N2C(=S)N(c3ccc(C#N)c(C(F)(F)F)c3)C(=O)C23CCC(C)(C)CC3)cc1F] |
| I-12 | DR108 | 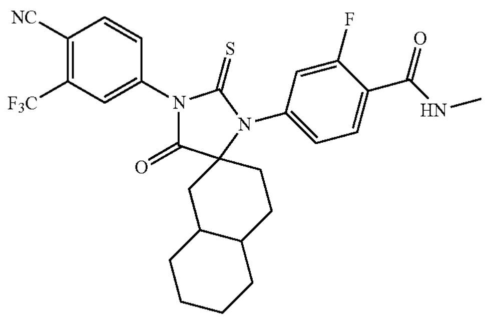 [SMILES: CNC(=O)c1ccc(N2C(=S)N(c3ccc(C#N)c(C(F)(F)F)c3)C(=O)C23CCC2CCCCC2C3)cc1F] |
| I-13 | DR109 | 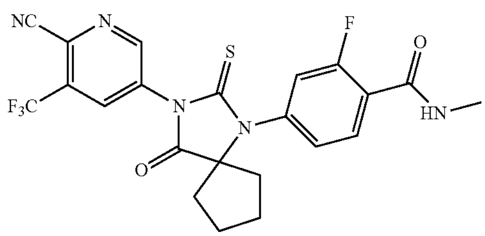 [SMILES: CNC(=O)c1ccc(N2C(=S)N(c3cnc(C#N)c(C(F)(F)F)c3)C(=O)C23CCCC3)cc1F] |
| I-14 | DR110 | 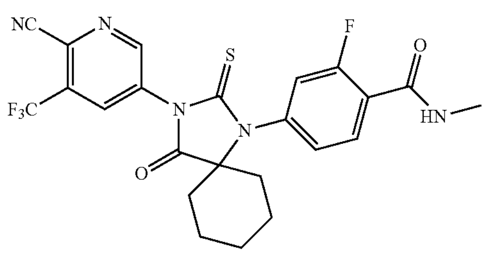 [SMILES: CNC(=O)c1ccc(N2C(=S)N(c3cnc(C#N)c(C(F)(F)F)c3)C(=O)C23CCCCC3)cc1F] |
| I-15 | DR111 | 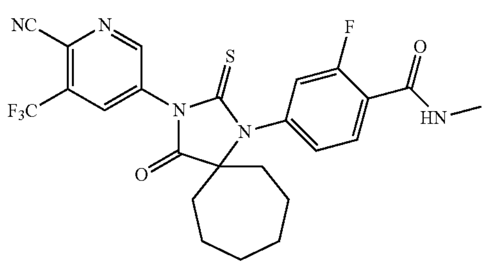 [SMILES: CNC(=O)c1ccc(N2C(=S)N(c3cnc(C#N)c(C(F)(F)F)c3)C(=O)C23CCCCCC3)cc1F] |

TABLE 2-continued

| Compound ID | MSKCC Code | Compound Structure |
| --- | --- | --- |
| I-16 | DR112 | 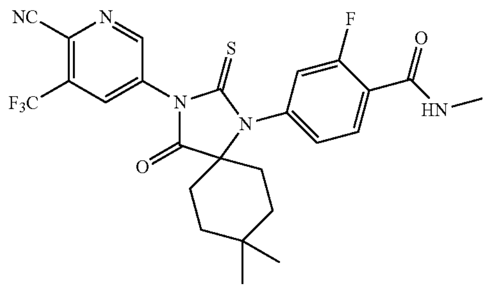 [SMILES: CNC(=O)c1ccc(N2C(=S)N(c3cnc(C#N)c(C(F)(F)F)c3)C(=O)C23CCC(C)(C)CC3)cc1F] |
| I-17 | DR113 | 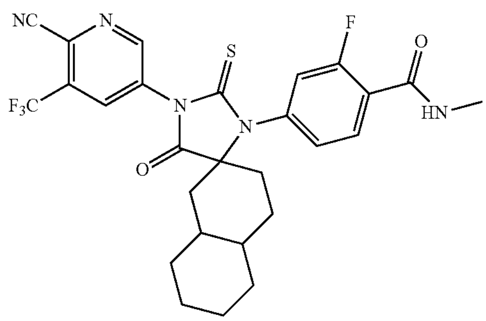 [SMILES: CNC(=O)c1ccc(N2C(=S)N(c3cnc(C#N)c(C(F)(F)F)c3)C(=O)C23CCC2CCCCC2C3)cc1F] |
| I-18 | DR116 | 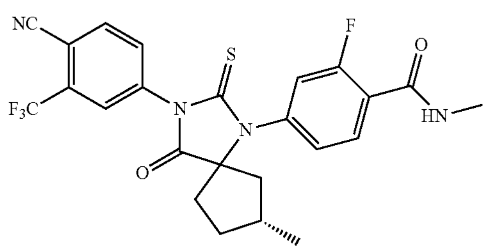 [SMILES: CNC(=O)c1ccc(N2C(=S)N(c3ccc(C#N)c(C(F)(F)F)c3)C(=O)C23CC[C@@H](C)C3)cc1F] |
| I-19 | DR117 | 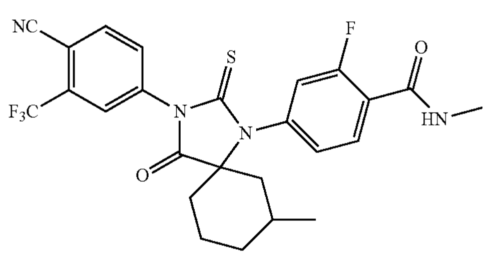 [SMILES: CNC(=O)c1ccc(N2C(=S)N(c3ccc(C#N)c(C(F)(F)F)c3)C(=O)C23CCCC(C)C3)cc1F] |
| I-20 | DR118 | 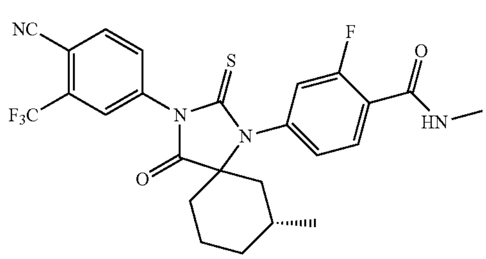 [SMILES: CNC(=O)c1ccc(N2C(=S)N(c3ccc(C#N)c(C(F)(F)F)c3)C(=O)C23CCC[C@@H](C)C3)cc1F] |

TABLE 2-continued

| Compound ID | MSKCC Code | Compound Structure |
|---|---|---|
| I-21 | DR119 | 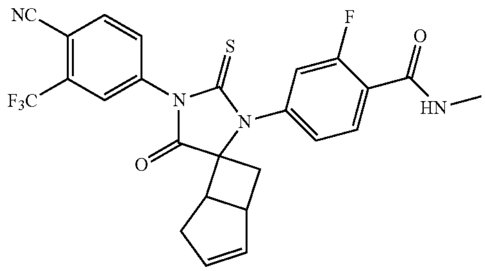 [SMILES: CNC(=O)c1ccc(N2C(=S)N(c3ccc(C#N)c(C(F)(F)F)c3)C(=O)C23CC2C=CCC23)cc1F] |
| I-22 | DR120 | 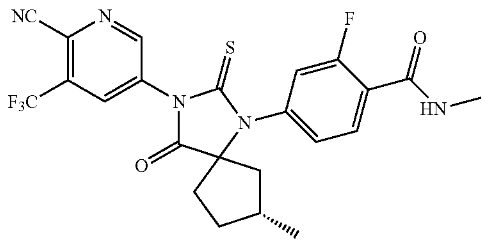 [SMILES: CNC(=O)c1ccc(N2C(=S)N(c3cnc(C#N)c(C(F)(F)F)c3)C(=O)C23CC[C@@H](C)C3)cc1F] |
| I-23 | DR121 | 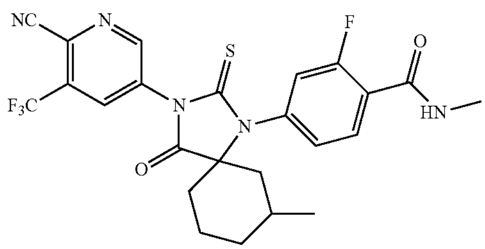 [SMILES: CNC(=O)c1ccc(N2C(=S)N(c3cnc(C#N)c(C(F)(F)F)c3)C(=O)C23CCCC(C)C3)cc1F] |
| I-24 | DR122 | 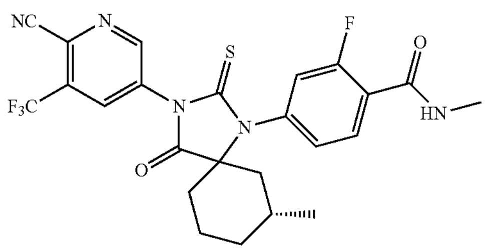 [SMILES: CNC(=O)c1ccc(N2C(=S)N(c3cnc(C#N)c(C(F)(F)F)c3)C(=O)C23CCC[C@@H](C)C3)cc1F] |
| I-25 | DR123 | 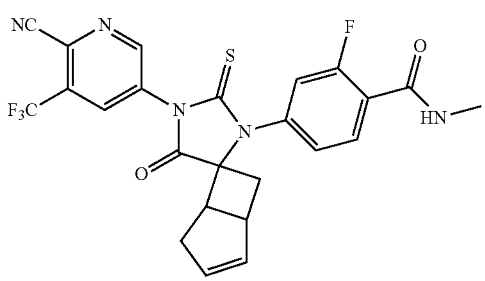 [SMILES: CNC(=O)c1ccc(N2C(=S)N(c3cnc(C#N)c(C(F)(F)F)c3)C(=O)C23CC2C=CCC23)cc1F] |
| I-26 | DR107 | 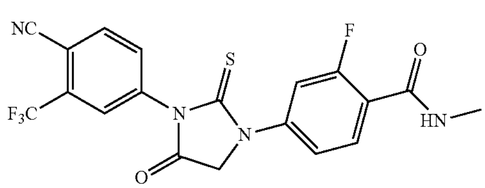 [SMILES: CNC(=O)c1ccc(N2CC(=O)N(c3ccc(C#N)c(C(F)(F)F)c3)C2=S)cc1F] |

TABLE 2-continued

| Compound ID | MSKCC Code | Compound Structure |
|---|---|---|
| I-27 | DR114 | 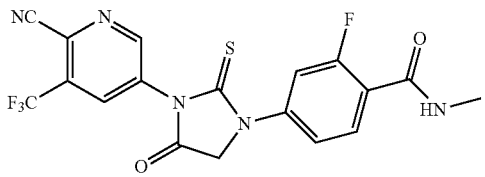 [SMILES: CNC(=O)c1ccc(N2CC(=O)N(c3cnc(C#N)c(C(F)(F)F)c3)C2=S)cc1F] |

In some embodiments, a subject is any mammalian subject at risk for a CRPC. In some embodiments, the subject is a human. In certain embodiments, the subject has prostate cancer. In some embodiments, the subject is currently being treated with anti-androgens.

In accordance with the methods of the invention, an agent described herein can be administered to a subject alone, or as a component of a composition or medicament (e.g., in the manufacture of a medicament for the prevention or treatment of CRPC), as described herein. The compositions can be formulated with a physiologically acceptable carrier or excipient to prepare a pharmaceutical composition. The carrier and composition can be sterile. The formulation should suit the mode of administration. Methods of formulating compositions are known in the art (see, e.g., Remington's Pharmaceuticals Sciences, 17$^{th}$ Edition, Mack Publishing Co., (Alfonso R. Gennaro, editor) (1989)).

Suitable pharmaceutically acceptable carriers include but are not limited to water, salt solutions (e.g., NaCl), saline, buffered saline, alcohols, glycerol, ethanol, gum arabic, vegetable oils, benzyl alcohols, polyethylene glycols, gelatin, carbohydrates such as lactose, amylose or starch, sugars such as mannitol, sucrose, or others, dextrose, magnesium stearate, talc, silicic acid, viscous paraffin, perfume oil, fatty acid esters, hydroxymethylcellulose, polyvinyl pyrolidone, etc., as well as combinations thereof. The pharmaceutical preparations can, if desired, be mixed with auxiliary agents (e.g., lubricants, preservatives, stabilizers, wetting agents, emulsifiers, salts for influencing osmotic pressure, buffers, coloring, flavoring and/or aromatic substances and the like) which do not deleteriously react with the active compounds or interference with their activity. In a preferred embodiment, a water-soluble carrier suitable for intravenous administration is used.

The composition or medicament, if desired, can also contain minor amounts of wetting or emulsifying agents, or pH buffering agents. The composition can be a liquid solution, suspension, emulsion, tablet, pill, capsule, sustained release formulation, or powder. The composition can also be formulated as a suppository, with traditional binders and carriers such as triglycerides. Oral formulations can include standard carriers such as pharmaceutical grades of mannitol, lactose, starch, magnesium stearate, polyvinyl pyrollidone, sodium saccharine, cellulose, magnesium carbonate, etc.

The composition or medicament can be formulated in accordance with the routine procedures as a pharmaceutical composition adapted for administration to human beings. For example, in a preferred embodiment, a composition for intravenous administration typically is a solution in sterile isotonic aqueous buffer. Where necessary, the composition may also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where the composition is to be administered by infusion, it can be dispensed with an infusion bottle containing sterile pharmaceutical grade water, saline or dextrose/water. Where the composition is administered by injection, an ampule of sterile water for injection or saline can be provided so that the ingredients may be mixed prior to administration.

An agent described herein can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

An agent described herein (or a composition or medicament containing an agent described herein) is administered by any appropriate route. In some embodiments, an agent is administered subcutaneously. As used herein, the term "subcutaneous tissue", is defined as a layer of loose, irregular connective tissue immediately beneath the skin. For example, the subcutaneous administration may be performed by injecting a composition into areas including, but not limited to, thigh region, abdominal region, gluteal region, or scapular region. In some embodiments, an agent is administered intravenously. In some embodiments, an agent is administered orally. In other embodiments, an agent is administered by direct administration to a target tissue, such as heart or muscle (e.g., intramuscular), tumor (intratumorallly), nervous system (e.g., direct injection into the brain; intraventricularly; intrathecally). Alternatively, an agent (or a composition or medicament containing an agent) can be administered by inhalation, parenterally, intradermally, transdermally, or transmucosally (e.g., orally or nasally). More than one route can be used concurrently, if desired.

In some embodiments, a composition is administered in a therapeutically effective amount and/or according to a dosing regimen that is correlated with a particular desired outcome (e.g., with treating or reducing risk for CRPC).

Particular doses or amounts to be administered in accordance with the present invention may vary, for example, depending on the nature and/or extent of the desired outcome, on particulars of route and/or timing of administration, and/or on one or more characteristics (e.g., weight, age, personal history, genetic characteristic, lifestyle parameter, or combinations thereof). Such doses or amounts can be determined by those of ordinary skill. In some embodiments, an appropriate dose or amount is determined in accordance with standard clinical techniques. Alternatively or additionally, in some embodiments, an appropriate dose or amount is determined through use of one or more in vitro or in vivo assays to help identify desirable or optimal dosage ranges or amounts to be administered.

In various embodiments, an agent is administered at a therapeutically effective amount. As used herein, the term "therapeutically effective amount" is largely determined based on the total amount of the therapeutic agent contained in the pharmaceutical compositions of the present invention. Generally, a therapeutically effective amount is sufficient to achieve a meaningful benefit to the subject (e.g., treating, modulating, curing, preventing and/or ameliorating the underlying disease or condition). In some particular embodiments, appropriate doses or amounts to be administered may be extrapolated from dose-response curves derived from in vitro or animal model test systems.

In some embodiments, a provided composition is provided as a pharmaceutical formulation. In some embodiments, a pharmaceutical formulation is or comprises a unit dose amount for administration in accordance with a dosing regimen correlated with achievement of the reduced incidence or risk of CPMC.

In some embodiments, provided compositions, including those provided as pharmaceutical formulations, comprise a liquid carrier such as but not limited to water, saline, phosphate buffered saline, Ringer's solution, dextrose solution, serum-containing solutions, Hank's solution, other aqueous physiologically balanced solutions, oils, esters and glycols.

In some embodiments, a formulation comprising an agent described herein administered as a single dose. In some embodiments, a formulation comprising an agent described herein is administered at regular intervals. Administration at an "interval," as used herein, indicates that the therapeutically effective amount is administered periodically (as distinguished from a one-time dose). The interval can be determined by standard clinical techniques. In some embodiments, a formulation comprising an agent described herein is administered bimonthly, monthly, twice monthly, triweekly, biweekly, weekly, twice weekly, thrice weekly, daily, twice daily, or every six hours. The administration interval for a single individual need not be a fixed interval, but can be varied over time, depending on the needs of the individual.

As used herein, the term "bimonthly" means administration once per two months (i.e., once every two months); the term "monthly" means administration once per month; the term "triweekly" means administration once per three weeks (i.e., once every three weeks); the term "biweekly" means administration once per two weeks (i.e., once every two weeks); the term "weekly" means administration once per week; and the term "daily" means administration once per day.

In some embodiments, a formulation comprising an agent described herein is administered at regular intervals indefinitely. In some embodiments, a formulation comprising an agent described herein is administered at regular intervals for a defined period. In some embodiments, a formulation comprising an agent described herein is administered at regular intervals for 5 years, 4, years, 3, years, 2, years, 1 year, 11 months, 10 months, 9 months, 8 months, 7 months, 6 months, 5 months, 4 months, 3 months, 2 months, a month, 3 weeks, 2, weeks, a week, 6 days, 5 days, 4 days, 3 days, 2 days or a day.

Combination Therapy

In some embodiments, an agent is administered in combination with one or more known therapeutic agents (e.g., anti-androgens) currently used for prostate cancer treatment and CPMC treatment as described herein. In some embodiments, the known therapeutic agent(s) is/are administered according to its standard or approved dosing regimen and/or schedule. In some embodiments, the known therapeutic agent(s) is/are administered according to a regimen that is altered as compared with its standard or approved dosing regimen and/or schedule. In some embodiments, such an altered regimen differs from the standard or approved dosing regimen in that one or more unit doses is altered (e.g., reduced or increased) in amount, and/or in that dosing is altered in frequency (e.g., in that one or more intervals between unit doses is expanded, resulting in lower frequency, or is reduced, resulting in higher frequency).

EXEMPLIFICATION

Example 1

Structure-Guided Design Identifies Antiandrogens to Overcome Enzalutamide Resistance Driven by a Novel Androgen Receptor Mutation A second-generation antiandrogen enzalutamide was recently approved for patients with CRPC. Despite its success, the duration of patient response is often limited. For previous antiandrogens, one mechanism of resistance is mutation of the androgen receptor (AR), converting antiandrogens into agonists of the mutant receptor. To identify AR mutations that might confer resistance to enzalutamide, a reporter-based mutagenesis screen was performed and novel mutation, F876L, was identified which converted enzalutamide into an agonist for AR. Ectopic expression of AR F876L rescued growth inhibition by enzalutamide treatment. Molecular dynamics simulations performed on antiandrogen-AR complexes suggested a mechanism by which the F876L substitution alleviates antagonism through repositioning of the co-activator recruiting helix 12. The simulations further suggested that chemically modifying enzalutamide to interfere with this positioning of H12 might restore antagonism. A focused chemical screen identified three compounds, ($\pm$)-DR103, DR105, and ($\pm$)-DR106 that effectively antagonized AR F876L (and AR WT) to suppress the growth of prostate cancer cells resistant to enzalutamide therapy.

Recent FDA approval of enzalutamide the critical role of AR signaling in castration-resistant prostate cancer. In spite of this milestone, patient responses to enzalutamide are variable and often short-lived. Reactivation of AR signaling has been implicated in resistance to previous antiandrogen therapy, and one well-documented mechanism of resistance is point mutation in the ligand-binding domain (LBD) of AR. Many of these mutations broaden ligand specificity and some confer resistance by converting AR antagonists into an agonist of the mutant receptor. It was speculated that one mechanism promoting resistance to enzalutamide therapy could be a mutation in AR that converts enzalutamide into an agonist.

Methods

Fetal bovine serum (FBS) and charcoal-stripped, dextran-treated fetal bovine serum (CSS) were purchased from Omega Scientific. Bicalutamide (Investigational Drug Pharmacy), hydroxyflutamide (LKT Labs), DHT (Sigma), and R1881 (Perkin Elmer) were commercially obtained; all other ligands were synthesized at MSKCC. Serial dilutions of all drugs were made using DMSO. Antibodies used for immunoblot assays were b-actin (AC-15, Sigma) PARP (#9543; Cell Signaling Technology), FKBP5 (IHC-00289, Bethyl), b-tubulin (D-10) and androgen receptor (N-20) (both from Santa Cruz Biotechnology). Protein lysates were prepared in M-PER protein extraction reagent (Pierce) or 1% SDS buffer. The chromatin immunoprecipation assay was conducted using a kit (Upstate) with an antibody for androgen receptor (PG-21, Upstate). Nontarget and mouse AR siRNA pools were from the ON-TARGETplus collection (Dharmacon).

LNCaP/AR cells were previously described (C. Tran et al., Development of a second-generation antiandrogen for treatment of advanced prostate cancer. Science 324, 787 (May 8, 2009)), and CWR22PC cells were provided by Marja T. Nevalainen (Thomas Jefferson University, Philadelphia). All other cell lines were obtained from ATCC. All LNCaP and CWR22PC derived cells were maintained in RPMI+10% FBS. All CV1 and VCaP derived cell lines were maintained in DMEM+10% FBS.

Plasmids & Cell Transduction

The human AR cDNA plasmid, pWZL-AR, was provided by William Hahn (Dana-Farber Cancer Institute, Boston). All specific mutant AR constructs were generated in the pWZL-AR vector with the QuickChange II XL site directed mutagenesis kit (Agilent)). All primers used to generate these mutants can be found in Table 3. Stable cell lines expressing the different AR cDNAs were generated by pantropic retroviral infection (Clontech) and selected with blasticidin (Invivogen).

TABLE 3

Site-Directed AR Mutagenesis Primers

| | | |
|---|---|---|
| W741C - sense | CATTCAGTACTCCTGCATGGGGCTCATGGTG |
| W741C - antisense | CACCATGAGCCCCATGCAGGAGTACTGAATG |
| T877A - sense | GAGAGCTGCATCAGTTCGCTTTTGACCTGCTAATC |
| T877A - antisense | GATTAGCAGGTCAAAAGCGAACTGATGCAGCTCTC |
| F876L - sense | CGAGAGAGCTGCATCAGCTCACTTTTGACCTGCT |
| F876L - antisense | AGCAGGTCAAAAGTGAGCTGATGCAGCTCTCTCG |
| F876C - sense | GAGAGAGCTGCATCAGTGCACTTTTGACCTGCTAA |
| F876C - antisense | TTAGCAGGTCAAAAGTGCACTGATGCAGCTCTCTC |
| F876I - sense | CGAGAGAGCTGCATCAGATCACTTTTGACCTGCTA |
| F876I - antisense | TAGCAGGTCAAAAGTGATCTGATGCAGCTCTCTCG |
| F876S - sense | CGAGAGAGCTGCATCAGTCCACTTTTGACCTGCTAA |
| F876S - antisense | TTAGCAGGTCAAAAGTGGACTGATGCAGCTCTCG |
| F876V - sense | CGAGAGAGCTGCATCAGGTCACTTTTGACCTGCTA |
| F876V - antisense | TAGCAGGTCAAAAGTGACCTGATGCAGCTCTCTCG |
| F876Y - sense | TGCGAGAGAGCTGCATCAGTACACTTTTGACCTGCTAA |

TABLE 3-continued

Site-Directed AR Mutagenesis Primers

| | | |
|---|---|---|
| F876Y - antisense | TTAGCAGGTCAAAAGTGTACTGATGCAGCTCTCTCGCA |

LNCaP cells were infected with the lentiviral AR-regulated EGFP reporter construct, Pb-PSE-EGFP (S. Chapel-Fernandes et al., Use of the PSA enhancer core element to modulate the expression of prostate- and non-prostate-specific basal promoters in a lentiviral vector context. Cancer Gene Ther 13, 919 (October, 2006)), provided by Claude Bignon (EFS Alpes Mediterranee, Marseilles, France). LNCaP-Pb.PSE.EGFP cells were single-cell cloned to reduce the heterogeneity in EGFP expression, and a clone was isolated that had a high level of EGFP expression, which was modulated effectively by antiandrogens and AR agonists. This clone was used for all flow cytometry assays and for the FACS-based resistance screens.

Flow Cytometry Analysis, and FACS-Sorting

LNCaP-Pb.PSE.EGFP cells for flow cytometric analysis were treated with antiandrogens (1 µM or 10 µM) for 4-6 days, changing media and drug every 2-3 days. Cells were collected using Accumax dissociation solution (Innovative Cell Technologies) and dead cells were counterstained using TO-PRO3-Iodide (Invitrogen). EGFP expression was measured using the BD-FACSCalibur flow cytometer using the 488 nm laser and 530/30 bandpass filter to detect EGFP expression, and the 633 nm laser and 661/16 bandpass filter to detect TO-PRO3-Iodide labeled dead cells. For each sample, 2-5×10$^4$ cell events were collected and analysis was done using FlowJo software. FACS-sorting of LNCaP-Pb.PSE.EGFP cells was performed on a BD FACSVantage cell sorter. EGFP expression was detected using the 488 nm laser and 530/30 bandpass filter, and DAPI-labeled dead cells were detected using the 355 nm laser and 450/50 bandpass filter.

FACS-Based Bicalutamide Proof-of-Concept Screen 4 additional synonymous mutations were introduced into pWZL-AR W741C to aid in distinguishing wild-type AR and AR W741C, using the QuikChange Multi Site-Directed Mutagenesis Kit (Agilent). Quantitative PCR primers across these mutation sites were then designed and optimized, so that they specifically amplified AR W741C. Wild-type (WT) AR or AR W741C in LNCaP-Pb.PSE.EGFP reporter cells were overexpressed, mixed different ratios of cells expressing either WT or W471C mutant AR, treated with 1 µM bicalutamide for 4 days, and cells that maintained/induced EGFP expression were FACS sorted. Gates for EGFP positivity were set using WT or W741C expressing cells treated bicalutamide. Sorted cells were expanded in culture (without drug) until they reached approximately 60 million cells. A small fraction of gDNA was then isolated and frozen down, and the brief bicalutamide treatment and sorting was repeated on the remainder. Primers used to introduce the additional synonymous mutations and for the subsequent quantitative PCR can be found in Table 4.

TABLE 4

Primers for W741C Proof of Concept Screen

| Synonymous Mutant Sense | |
|---|---|
| W741C-S1 | ACAGCTTGTACACGTCGTCAAGTGGGCCAAG |
| W741C-S2 | ACAGCTTGTACACGTCGTGAAGTGGGCCAAG |

TABLE 4-continued

Primers for W741C Proof of Concept Screen

Synonymous Mutant Sense

| | |
|---|---|
| W741C-S3 | TACCGCATGCACAAGTCGCGGATGTACAGCCAG |
| W741C-S4 | TACCGCATGCACAAGTCGCGCATGTACAGCCAG |

Quantitative PCR primers

| | |
|---|---|
| vector control-forward | GTCCCCTACATCGTGACCTG |
| vector control-reverse | GAGGTTCAAGGGGGAGAGAC |
| W741C-SM-forward | AGAGACAGCTTGTACACGTCGTG |
| W741C-SM-reverse | ACACACTGGCTGTACATGCGC |

FACS-Based Enzalutamide Resistance Screen

A randomly mutagenized AR cDNA library was generated as follows: the DNA-repair-deficient *Escherichia coli* strain XL-1 Red (Agilent) was transformed with the pWZL-AR plasmid and plated on ampicillin-agar bacterial plates. After a 36 hour incubation, colonies were collected by scraping, and plasmid DNA was purified using a plasmid MAXI kit (Qiagen). Subsequently, this mutagenized AR plasmid stock was used to make pantropic retrovirus (Clontech) and infect LNCaP-Pb.PSE.EGFP cells at a MOI<1. Cells were selected for stable expression of mutant pWZL-AR library using the blasticidin resistance cassette. Mutant library cells were plated in 1 µM enzalutamide for 4-6 days (refreshing media & drug every 2-3 days), collected with Accumax and resuspended in Accumax containing 0.5% BSA and 10 mM HEPES. Dead cells were counterstained with DAPI (Invitrogen). Cells were then subjected to FACS-sorting on the BD FACSVantage cell sorter, to sort out the cells that remained EGFP positive in the presence of enzalutamide. Gates for EGFP positivity were set using LNCaP-Pb.PSE.EGFP cells transduced with the wild-type AR cDNA, treated with vehicle or 1 µM enzalutamide. Sorted cells were expanded in culture (without drug) until they reached approximately 60 million cells. A small fraction of gDNA was then isolated and frozen down, and the brief enzalutamide treatment and sorting was repeated on the remainder. The screen was performed in triplicate, with 5 rounds of FACS and expansion for each replicate.

AR Mutation Detection

Exons 2 through 8 of the exogenously expressed AR cDNA were amplified from genomic DNA isolated from cells after each sort, by high-fidelity PCR (Qiagen, Hotstar) on a Mastercycler (Eppendorf). PCR product was subjected to bidirectional Sanger sequencing using several different AR primers. Primers used for PCR amplification and subsequent AR sequencing are listed in Table 5 (P. A. Watson et al., Constitutively active androgen receptor splice variants expressed in castration-resistant prostate cancer require full-length androgen receptor. *Proc Natl Acad Sci USA* 107, 16759 (Sep. 28, 2010)). Alignments were performed using SeqMan Pro (DNASTAR) and Sanger traces were analyzed using 4 Peaks software.

TABLE 5

Primers to amplify & sequence AR cDNA

PCR amplification of AR cDNA from gDNA

| | |
|---|---|
| AR-exon2-forward | ACATGCGTTTGGAGACTGC |
| AR-3UTR-reverse-1 | TGGTCGACTAGATCCCCTATGA |
| AR-3UTR-reverse-2 | CAAGGCACTGCAGAGGAGTA |

AR sequencing primers

| | |
|---|---|
| AR-F1 | TGTCCATCTTGTCGTCTTCG |
| AR-F2 | GTCCTGGAAGCCATTGAGCCA |
| AR-F3 | CCAGATGGCTGTCATTCAGTA |
| AR-R1 | GAAGACCTTGCAGCTTCCAC |
| AR-R2 | ACACACTACACCTGGCTCAAT |
| AR-R3 | CAGGCAGAAGACATCTGAAAG | qRT-PCR

Total RNA was isolated using the QiaShredder kit (Qiagen) for cell lysis and the RNeasy kit (Qiagen) for RNA purification. High Capacity cDNA Reverse Transcription Kit (Applied Biosystems) was used to synthesize cDNA according to the manufacturer's protocol. Quantitative PCR was done in the Realplex MasterCycler (Eppendorf) using the Power SYBR Green PCR Mastermix (Applied Biosystems). Quantitative PCR for each sample was run in triplicate and each reaction contained 1 µL of cDNA in a total volume of 20 µL. PCR quantification was done using the 2-ΔΔCt method with normalization to GAPDH as described (Applied Biosystems). All primers were synthesized by Operon Biotechnologies and used at a final concentration of 500 nM, sequences can be found in table 6 (D. S. Welsbie et al., Histone deacetylases are required for androgen receptor function in hormone-sensitive and castrate-resistant prostate cancer. *Cancer Res* 69, 958 (Feb. 1, 2009)).

TABLE 6

Quantitative RT-PCR primers

| Name | Sequence |
|---|---|
| GAPDH - forward | GAAGGTGAAGGTCGGAGTC |
| GAPDH - reverse | GAAGATGGTGATGGGATTTC |
| PSA - forward | GGTGACCAAGTTCATGCTGTG |
| PSA - reverse | GTGTCCTTGATCCACTTCCG |
| Tmprss2 - forward | CACTGTGCATCACCTTGACC |
| Tmprss2 - reverse | ACACGCCATCACACCAGTTA |
| FKBP5 - forward | TCCCTCGAATGCAACTCTCT |
| FKBP5 - reverse | GCCACATCTCTGCAGTCAAA |

TABLE 6-continued

Quantitative RT-PCR primers

| Name | Sequence |
| --- | --- |
| SGK1 - forward | GCAGAAGGACAGGACAAAGC |
| SGK1 - reverse | CAGGCTCTTCGGTAAACTCG |

Chromatin Immunoprecipitation

LNCaP cells (107 cells/condition) were grown in phenol red free RPMI media supplemented with 10% CSS for 4 days, then treated with DMSO, 10 uM antiandrogens, or 1 nM DHT for 4 hours. The cells were then cross-linked using 1% paraformaldehyde (Electron Microscopy Sciences) for 15 minutes. Glycine was then added, and samples were centrifuged (40° C., 4000 rpm, 5 minutes) to stop further crosslinking Chromatin immunoprecipitation was performed according to manufacturer's protocols using a chromatin immunoprecipitation assay kit (Upstate). Immunoprecipitated DNA was amplified by real-time PCR (ABI Power SYBR Green PCR mix). Primers can be found in table 7.

TABLE 7

| ChIP quantitative PCR primers | |
| --- | --- |
| PSA-Enhancer - forward (1) | ATGTTCACATTAGTACACCTTGCC |
| PSA-Enhancer - reverse (1) | TCTCAGATCCAGGCTTGCTTACT-GTC |
| FKBP5-Enhancer - forward | CCCCCTATTTTAATCGGAGTAC |
| FKBP5-Enhancer - reverse | TTTTGAAGAGCACAGAACACCT |

Fluorescence Microscopy

LNCaP cells ($10^6$ cells/well of 6-well plate) were transfected with 2 μg AR-EYFP plasmid (gift of Jeremy Jones and Marc Diamond, UCSF) or AR.F876L-EYFP plasmid (QuikChange II XL site-directed mutagenesis kit) using FUGENE HD (Roche). Six hours after transfection, media was removed and replaced with phenol red free RPMI media supplemented with 10% CSS. The next day cells were split and plated onto poly-lysine coated Nunc Labtek chamber slides in RPMI+10% CSS containing DMSO, 1 μM antiandrogens or 1 nM DHT. Twenty-four hours later the cells were counterstained with NucBlue Live Cell Stain Hoechst 33342 (Molecular Probes) fixed with 4% paraformaldehyde, and mounted with a coverslip. Images were taken on a Leica TCS SP5-II Upright confocal microscope (MSKCC Microscopy Core and were analyzed for EYFP (AR) nuclear/cytoplasmic localization using ImageJ.

AR Luciferase Reporter Assay

CV1 cells (106 cells/10 cm plate) were cotransfected with 50 ng of SV40 Renilla Luciferase, 5 ug of ARE(4X)-Luciferase, and 10 μg of one pWZL-AR expression construct using Lipofectamine 2000 (Invitrogen). Transfection media was removed 4-6 hours later and replaced with phenol red free DME-HG containing 10% charcoal stripped serum. The following day each plate was split into 24- or 48-well plates, in 10% CSS media, containing the indicated drugs in triplicate. Twenty-four to forty-eight hours later, luciferase activity was assayed using Dual-Luciferase Reporter Assay System (Promega) on a 96-well luminometer (Turner Biosystems).

Xenograft Experiments

In vivo xenograft experiments were done by subcutaneous injection of $2\times10^6$ LNCaP/AR cells ectopically expressing AR WT or AR F876L (100 μL in 50% Matrigel (BD Biosciences) and 50% growth media) into the flanks of castrated male SCID mice. Daily gavage treatment (using a formulation of 1% carboxymethyl cellulose, 0.1% Tween-80, 5% DMSO) was initiated on the day of injection. Once tumors were palpable, tumor size was measured weekly in three dimensions (l×w×d) with calipers. All animal experiments were performed in compliance with the guidelines of the Research Animal Resource Center of the Memorial Sloan-Kettering Cancer Center.

Xenograft experiments in which AR F876 mutations emerged after long-term treatment with second-generation antiandrogens were performed as follows: $2\times10^6$ LNCaP/AR cells (C. Tran et al., Development of a second-generation antiandrogen for treatment of advanced prostate cancer. *Science* 324, 787 (May 8, 2009)) were injected subcutaneously into the flanks of castrated SCID mice. Treatment with 30 mg/kg enzalutamide or ARN-509 (or vehicle) was initiated once tumors reached ~300 $mm^3$, resulting in rapid tumor regression. After several weeks of continual dosing, these tumors regain the ability to grow. Once these "resistant" tumors reached their original volume, the mice were sacrificed, and tumors collected for analysis.

Deep Sequencing of AR in Prostate Cancer Cell Lines and Xenograft Tumors Genomic DNA (gDNA) was isolated (PureGene Core Kit A, Qiagen) from CWR22PC cells or LNCaP/AR xenograft tumors. With 20 ng of gDNA as template, exon 8 of AR was PCR amplified with a proof-reading enzyme, Kapa HiFi Ready Mix (Kapa Biosystems, catalog # KK2612. RNA was extracted from LNCaP/AR xenograft tumors, reverse transcribed (High Capacity cDNA Reverse Transcription Kit, Applied Biosystems) and exons 2 through 8 of AR was PCR amplified using 200 ng cDNA as template (Qiagen, HotStar) (exon 2-forward, 3UTR-reverse-2; Table 4).

PCR reactions were cleaned up with AMPure XP (Beckman Coulter Genomics) and pooled reaction yields were quantified using the Qubit fluorometer (Invitrogen). Library preparation was done using Nextera DNA Sample Preparation kit (Illumina, catalog #FC-121-1031) and run on the Illumina MiSeq sequencer using the 2×250 paired-end cycle protocol.

Genomic DNA was aligned to the hg19 build of the human genome using BWA (Cornell, W. D., Cieplak, P., Bayly, C. I. & Kollmann, P. A. Application of RESP charges to calculate conformational energies, hydrogen bond energies, and free energies of solvation. *J Am Chem Soc.* 115, 9620-9631 (1993)) with duplicate removal using samtools (Momany, F. A. & Rone, R. Validation of the general purpose QUANTA 3.2/CHARMm force field. *J Comput Chem.* 13, 888-900 (1992)) as implemented by Illumina MiSeq Reporter. cDNA FASTQ files were processed with a windowed adaptive trimming tool sickle (https://github-.com/najoshi/sickle) using a quality threshold of 32. The reads were then mapped to the human genome build hg19 with TopHat 2 (Brooks, B. R. et al. CHARMM: A program for macromolecular energy, minimization, and dynamics calculations. *J Comput Chem.* 4, 187-217 (1983)) using known AR transcripts NM_000044 and NM_001011645. Duplicates were then removed with Picard (http://picard-.sourceforge.net). Variant detection was performed using VarScan 2 (Brooks, B. R. et al. CHARMM: The Biomolecular Simulation Program. *J Comput Chem.* 30, 1545-1614 (2009)) with thresholds of a minimum of 10 supporting variant reads and variant allele frequencies of at least 1%.

Analogue Syntheses
General Strategy

The syntheses were executed according to a general schema which involves starting from a given ketone and reacting it under Strecker reaction conditions, using Sodium cyanide and 4-amino-2-fluoro-N-methylbenzamide. The resulting cyanamine was then reacted an aniline or a 5-aminopyridine in the present of thiophosgene to give the desired thiohydantoins after acid hydrolysis of intermediate imine.

General Synthesis Schema

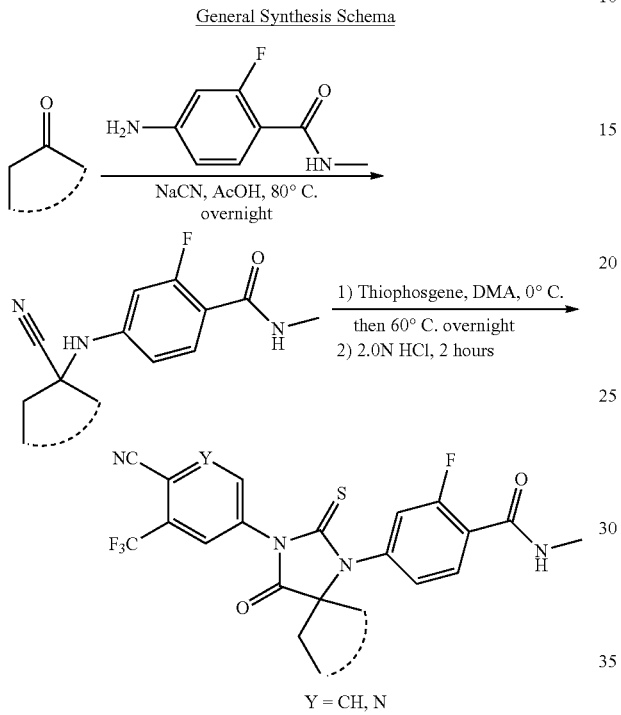

Y = CH, N

Below are two general procedures that apply to all molecules described below.

Strecker Reaction

To a mixture of 4-amino-2-fluoro-N-methylbenzamide (0.3 mmol) and desired ketone (1.0-2.0 eq) in glacial acetic acid (2 mL) was added NaCN (100 mg, 2.0 mmol, 7.0 eq), and the mixture was heated to 80° C. overnight. The solvent was then removed under reduced pressure and the residue was dissolved in water (20 mL), then pH was brought to neutrality with acqueous saturated NaHCO$_3$ solution. Extraction with ethyl acetate (3×50 ml), brief drying over Na$_2$SO$_4$ and concentration of the filtrate under reduced pressure and the residue was chromatographed on a short path silica gel column using the gradient hexane/ethyl acetate 2/1 to 1/1.5 (v/v) to yield desired product in more than 85% yield.

Thiohydantoin Synthesis

Thiophosgene (5.1 μL, 66 μmol) is added dropwise to a solution of 5-amino-2-cyano-3-trifluoromethylpyridine or 4-amino-2-(trifluoromethyl)benzonitrile (60 μmol) and the given Strecker products above N-methyl-4-(1-cyanocycloalkylamino)-2-fluorobenzamides (60 μmol) in dry DMA (0.6 mL) under Argon at 0° C. After 5 min, the solution is stirred overnight at 60° C. At room temperature, this mixture was then diluted with MeOH (1 mL) and aq. 2.0 N HCl (0.5 mL), then the reaction was brought to reflux for 2 hours. After cooling to ambient temperature, the reaction mixture was poured into ice water (10 mL) and extracted with EtOAc (3×20 mL). The organic layer was briefly dried over Mg$_2$SO$_4$, concentrated and the residue chromatographed on silica gel using the gradient system hexane/ethyl acetate 2/1 to 1.5/1 (v/v) to yield the desired thiohydantoin in up to 90%.

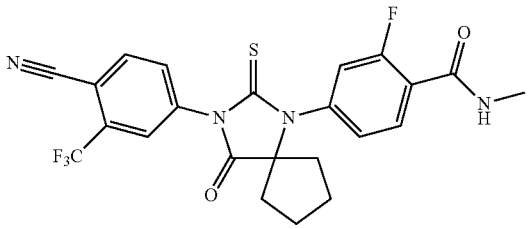 [SMILES: CNC(=O)c1ccc(N2C(=S)N(c3ccc(C#N)c(C(F)(F)F)c3)C(=O)C23CCCC3)cc1F]

DR100, 4-(3-(4-cyano-3-(trifluoromethyl)phenyl)-4-oxo-2-thioxo-1,3-diazaspiro[4.4]nonan-1-yl)-2-fluoro-N-methylbenzamide This compound was isolated as an off-white foam.
$^1$HNMR (CDCl$_3$): δ: 8.28 (t, 1 H, J=8.5 Hz), 7.79 (d, 1 H, J=8.3 Hz), 7.96 (bs, 1 H), 7.84 (dd, 1 H, J=8.3 Hz, J=1.5 Hz), 7.27 (dd, 1 H, J=8.3 Hz, J=1.8 Hz), 7.17 (dd, 1 H, J=11.7 Hz, J=1.5 Hz), 6.71 (m, 1 H), 3.07 (d, 3 H, J=4.7 Hz), 2.36 (m, 2 H), 2.16 (m, 2 H), 1.91 (m, 2 H), 1.56 (m, 2 H).
$^{19}$FNMR (CDCl$_3$) δ: −61.98, −110.64.
LRMS for C$_{23}$H$_{18}$F$_4$N$_4$O$_2$S [M+H]$^+$. found: 491.22. calculated: 491.12

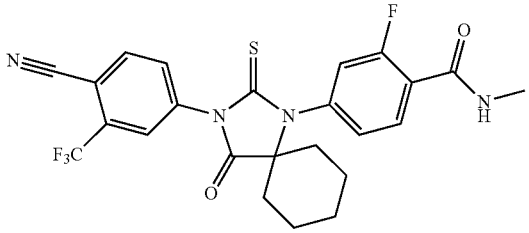 [SMILES: CNC(=O)c1ccc(N2C(=S)N(c3ccc(C#N)c(C(F)(F)F)c3)C(=O)C23CCCCC3)cc1F]

DR101, 4-(3-(4-cyano-3-(trifluoromethyl)phenyl)-4-oxo-2-thioxo-1,3-diazaspiro[4.5]decan-1-yl)-2-fluoro-N-methylbenzamide The compound was obtained as an off-white foam.
$^1$ HNMR (CDCl$_3$): δ: 8.27 (t, 1 H, J=8.4 Hz), 7.98 (d, 1 H, J=8.3 Hz), 7.93 (bs, 1 H), 7.82 (dd, 1 H, J=8.2 Hz, J=1.6 Hz), 7.19 (dd, 1 H, J=8.3 Hz, J=1.8 Hz), 7.08 (dd, 1 H, J=11.6 Hz, J=1.6 Hz), 6.70 (m, 1 H), 3.08 (d, 3 H, J=4.7 Hz), 2.07 (m, 4 H), 1.70 (m, 6 H).
$^{19}$FNMR (CDCl$_3$) δ: −61.97, −110.92.
LRMS for C$_{24}$H$_{20}$F$_4$N$_4$O$_2$S [M+H]$^+$. found: 505.30. calculated: 505.13

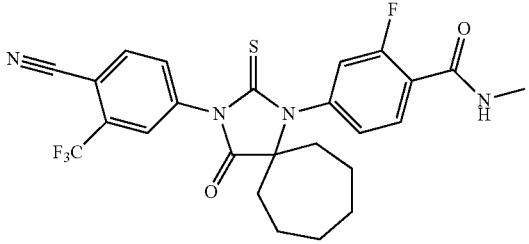 [SMILES: CNC(=O)c1ccc(N2C(=S)N(c3ccc(C#N)c(C(F)(F)F)c3)C(=O)C23CCCCCC3)cc1F]

DR102, 4-(3-(4-cyano-3-(trifluoromethyl)phenyl)-4-oxo-2-thioxo-1,3-diazaspiro[4.6]undecan-1-yl)-2-fluoro-N-methylbenzamide This compound was isolated as off-white solid.
$^1$HNMR (CDCl$_3$): δ: 8.28 (t, 1 H, J=8.4 Hz), 7.98 (d, 1 H, J=8.3 Hz), 7.93 (bs, 1 H), 7.82 (dd, 1 H, J=8.2 Hz, J=1.6 Hz), 7.24 (dd, 1 H, J=8.3 Hz, J=1.6 Hz), 7.14 (dd, 1 H, J=11.6 Hz, J=1.5 Hz), 6.72 (m, 1 H), 3.08 (d, 3 H, J=4.7 Hz), 2.28 (m, 2 H), 2.17 (m, 2 H), 1.81 (m, 2 H), 1.60 (m, 2 H), 1.44 (m, 2 H), 1.32 (m, 2 H).

$^{19}$FNMR (CDCl$_3$) δ: −61.98, −110.82.

LRMS for C$_{25}$H$_{22}$F$_4$N$_4$O$_2$S [M+H]$^+$. found: 519.38. calculated: 519.15.

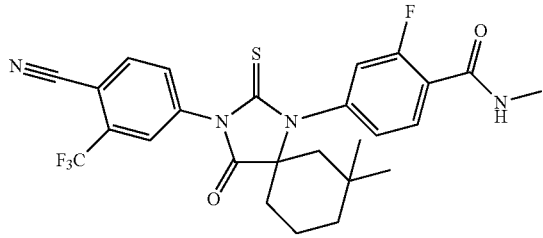 [SMILES: CNC(=O)c1ccc(N2C(=S)N(c3ccc(C#N)c(C(F)(F)F)c3)C(=O)C23CCCC(C)(C)C3)cc1F]

(±)-DR103, 4-(3-(4-cyano-3-(trifluoromethyl)phenyl)-7,7-dimethyl-4-oxo-2-thioxo-1,3-diazaspiro[4.5]decan-1-yl)-2-fluoro-N-methylbenzamide Racemic DR103 was synthesized in 70% overall yield as an off-white powder.

$^1$HNMR (CDCl$_3$): δ: 8.27 (t, 1 H, J=8.4 Hz), 7.98 (d, 1 H, J=8.3 Hz), 7.92 (bs, 1 H), 7.80 (dd, 1 H, J=8.2 Hz, J=1.7 Hz), 7.17 (dd, 1 H, J=8.3 Hz, J=1.7 Hz), 7.07 (dd, 1 H, J=11.6 Hz, J=1.6 Hz), 6.70 (m, 1 H), 3.08 (d, 3 H, J=4.7 Hz), 2.27 (m, 1 H), 2.17 (m, 1 H), 1.93 (m, 1 H), 1.67 (m, 1 H), 1.62 (m, 1 H), 1.57 (m, 1 H), 1.52 (m, 2 H), 1.20 (s, 3 H), 0.95 (s, 3 H).

$^{19}$FNMR (CDCl$_3$) δ: −61.98, −110.89.

LRMS for C$_{26}$H$_{24}$F$_4$N$_4$O$_2$S [M+H]$^+$. found: 533.33. calculated: 533.17.

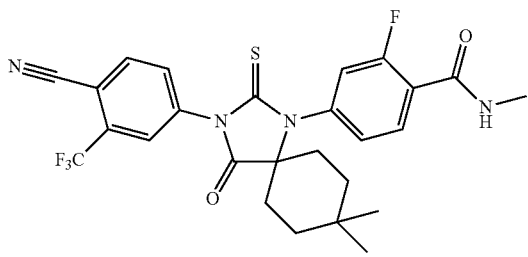 [SMILES: CNC(=O)c1ccc(N2C(=S)N(c3ccc(C#N)c(C(F)(F)F)c3)C(=O)C23CCC(C)(C)CC3)cc1F]

DR104, 4-(3-(4-cyano-3-(trifluoromethyl)phenyl)-8,8-dimethyl-4-oxo-2-thioxo-1,3-diazaspiro[4.5]decan-1-yl)-2-fluoro-N-methylbenzamide It was isolated as an off-white powder.

$^1$HNMR (CDCl$_3$): δ: 8.30 (t, 1 H, J=8.4 Hz), 7.98 (d, 1 H, J=8.3 Hz), 7.93 (bs, 1 H), 7.82 (dd, 1 H, J=8.2 Hz, J=1.6 Hz), 7.22 (dd, 1 H, J=8.3 Hz, J=1.6 Hz), 7.11 (dd, 1 H, J=11.6 Hz, J=1.5 Hz), 6.72 (m, 1 H), 3.08 (d, 3 H, J=4.7 Hz), 2.04 (m, 2 H), 1.93 (m, 4 H), 1.37 (m, 2 H), 0.99 (s, 3 H), 0.73 (s, 3 H).

$^{19}$FNMR (CDCl$_3$) δ: −61.98, −110.75.

LRMS for C$_{26}$H$_{24}$F$_4$N$_4$O$_2$S [M+H]$^+$. found: 533.33. calculated: 533.17.

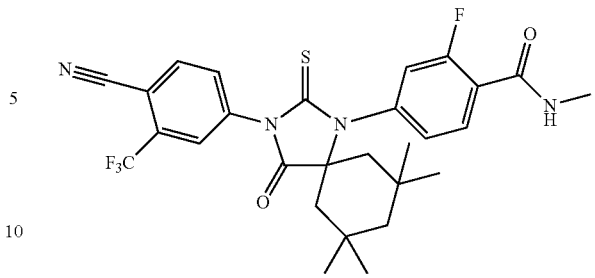

DR105, 4-(3-(4-cyano-3-(trifluoromethyl)phenyl)-7,7,9,9-tetramethyl-4-oxo-2-thioxo-1,3-diazaspiro[4.5]decan-1-yl)-2-fluoro-N-methylbenzamide This compound was isolated as a beige foam.

$^1$HNMR (CDCl$_3$): δ: 8.21 (t, 1 H, J=8.4 Hz), 7.90 (d, 1 H, J=8.3 Hz), 7.85 (bs, 1 H), 7.73 (dd, 1 H, J=8.2 Hz, J=1.2 Hz), 7.12 (dd, 1 H, J=8.3 Hz, J=1.2 Hz), 7.02 (dd, 1 H, J=11.6 Hz, J=1.2 Hz), 6.64 (m, 1 H), 3.01 (d, 3 H, J=4.7 Hz), 1.94 (d, 2H, J=14.4 Hz), 1.62 (d, 2H, J=14.4 Hz), 1.50 (s, 2 H), 1.17 (s, 6 H), 0.83 (s, 6 H).

$^{19}$FNMR (CDCl$_3$) δ: −61.98, −110.89.

LRMS for C$_{26}$H$_{24}$F$_4$N$_4$O$_2$S [M+H]$^+$. found: 561.29. calculated: 561.20.

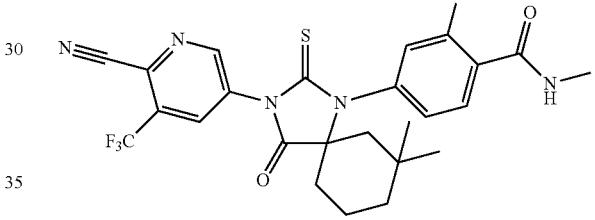

(±)-DR106, 4-(3-(6-cyano-5-(trifluoromethyl)pyridin-3-yl)-7,7-dimethyl-4-oxo-2-thioxo-1,3-diazaspiro[4.5]decan-1-yl)-2-fluoro-N-methylbenzamide This compound was isolated as an off-white foam.

$^1$HNMR (CDCl$_3$): δ: 9.06 (d, 1 H, J=1.9 Hz), 8.33 (d, 1 H, J=1.9 Hz), 8.29 (t, 1 H, J=8.4 Hz), 7.18 (dd, 1 H, J=8.4 Hz, J=1.6 Hz), 7.07 (dd, 1 H, J=11.5 Hz, J=1.5 Hz), 6.71 (m, 1 H), 3.08 (d, 3 H, J=4.7 Hz), 2.30 (m, 1 H), 2.18 (m, 1 H), 1.94 (m, 1 H), 1.72 (m, 1 H), 1.63 (m, 1 H), 1.57 (m, 1 H), 1.52 (m, 2 H), 1.20 (s, 3 H), 0.94 (s, 3 H).

$^{19}$FNMR (CDCl$_3$) δ: −61.87, −110.71.

LRMS for C$_{25}$H$_{23}$F$_4$N$_5$O$_2$S [M+H]$^+$. found: 534.31. calculated: 534.16.

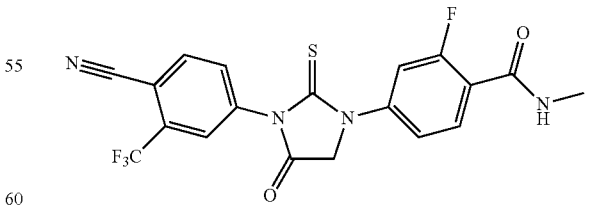

DR107, 4-(3-(4-cyano-3-(trifluoromethyl)phenyl)-4-oxo-2-thioxoimidazolidin-1-yl)-2-fluoro-N-methylbenzamide This compound was isolated as a white to off-white powder.

$^1$HNMR (CDCl$_3$): δ: 8.26 (t, 1 H, J=8.4 Hz), 8.02 (d, 1 H, J=8.3 Hz), 7.91 (bs, 1 H), 7.79 (m, 2 H), 7.45 (dd, 1 H, J=10.7 Hz, J=1.3 Hz), 6.71 (m, 1 H), 4.71 (s, 2 H), 3.06 (d, 3 H, J=4.7 Hz).

$^{19}$FNMR (CDCl$_3$) δ: −62.05, −110.31.

LRMS for C$_{19}$H$_{12}$F$_4$N$_4$O$_2$S [M+H]$^+$. found: 437.19. calculated: 437.07.

Initial Models of AR-Antiandrogen Complex Structures

No structures have been solved experimentally for enzalutamide or ARN-509 in complex with AR (agonist or antagonist conformation). Therefore, 3D structures of antiandrogens were first built using the computer program Gaussview (version 4.1.2, part of the computer program Gaussian 03 (Frisch, M. et al. Gaussian 03, Revision C.02. (Gaussian, Inc.): Wallingford, Conn., 2004)) and then geometrically optimized in a quantum mechanical force field at the level of restricted Hartree-Fock (RHF) 6-31 g* using the program Gaussian 03. The partial atomic charges were derived from the optimized structures by Restrained ElectroStatic Potential (Bayly, C. I., Cieplak, P., Cornell, W. & Kollman, P. A. A well-behaved electrostatic potential based method using charge restraints for deriving atomic charges: the RESP model. J Phys Chem. 97, 10269-10280 (1993), Cornell, W. D., Cieplak, P., Bayly, C. I. & Kollmann, P. A. Application of RESP charges to calculate conformational energies, hydrogen bond energies, and free energies of solvation. J Am Chem Soc. 115, 9620-9631 (1993)) (RESP) fitting to the RHF/6-31g* potentials. The other parameters modeling the antiandrogens were taken from the CHARMm22 (Momany, F. A. & Rone, R. Validation of the general purpose QUANTA 3.2/CHARMm force field. J Comput Chem. 13, 888-900 (1992)) force field after assigning CHARMm22 atom types to antiandrogens with an in-house program.

The initial AR-antiandrogen complex structures were then modeled with the molecular modeling program CHARMM (Brooks, B. R. et al. CHARMM: A program for macromolecular energy, minimization, and dynamics calculations. J Comput Chem. 4, 187-217 (1983), Brooks, B. R. et al. CHARMM: The Biomolecular Simulation Program. J Comput Chem. 30, 1545-1614 (2009)). Starting with the atomic coordinates of AR WT and A ring of 51 in the template crystal structure (PDB accession code, 2AXA), the side chain of residue 761 were replaced with CHARMm22-parameterized side chain of a leucine in cases of AR F876L and a CH group on the A ring was replaced with a nitrogen in cases of ARN-509. The rest of each antiandrogen was "grown" from the A ring using the ideal, unbound structures solved by geometry optimization. Missing side chain atoms were built using standard CHARMm22 parameters and hydrogen atoms were added with the HBUILD$^7$ module of CHARMM. All these newly-introduced atoms without 3D crystal coordinates treated flexible and the rest under harmonic constraints with the force constant of 100 Kcal/mol/Å$^2$, each AR-antiandrogen complex structure was energetically minimized with 1 round of 100-step steepest decent followed by 2 rounds of 100-step Adopted-Basis Newton-Raphson (ABNR) energy minimization. Harmonic constraints were reset at the beginning of each round of minimization. No nonbonded cutoff was used. Solvent effects were implicitly modeled in this stage with a distance-dependent dielectric constant.

Molecular Dynamics Simulations

The all-atom MD simulations were performed with explicit solvent atoms using the program CHARMM (version 36a1). Each initial AR-antiandrogen model was first centered and overlaid with a 50 Å×50 Å×50 Å cube of approximately 47,000 equilibrated water molecules. Any water molecule whose oxygen atom was within 2.8 Å away from any non-hydrogen atom of AR or antiandrgeon was removed. Proper amount of sodium and chloride ions were automatically added to achieve overall charge neutrality and physiological level of ion concentration (0.145 M). Their positions were optimized with 10 independent trajectories of randomly replacing water molecules and performing 50 steps of steepest decent and 125 steps of ABNR energy minimization.

The molecular system including AR, antiandrogen, waters, and ions was heated to 298 K and equilibrated with two rounds of 0.1-ns MD simulations under successively weaker harmonic constraints on AR or antiandrogen atoms. After the MD equilibration, three sets of random velocities were assigned to initiate three independent 10-ns MD productions. The MD equilibration and production were performed using the crystal form of rhombic dodecahedron (RHDO) and the canonical ensemble (NVT). A nonbonded cutoff of 10 Å, periodic boundary conditions in conjunction with Ewald summation method, the leapfrog Verlet integrator, and the Hoover thermostat for pressure and temperature were used. The timestep was set as 2 fs. Parallel jobs for MD simulations were run on a computer cluster of Intel Xeon X5650 series (2.66 GHz and 4 GB memory for each CPU).

Molecular Visualization

Structural models were visualized in a molecular graphics program, UCSF Chimera (Pettersen, E. F. et al. UCSF Chimera—a visualization system for exploratory research and analysis. J Comput Chem. 25, 1605-1612 (2004)). The default option used when aligning structures.

Results

Figure 1:
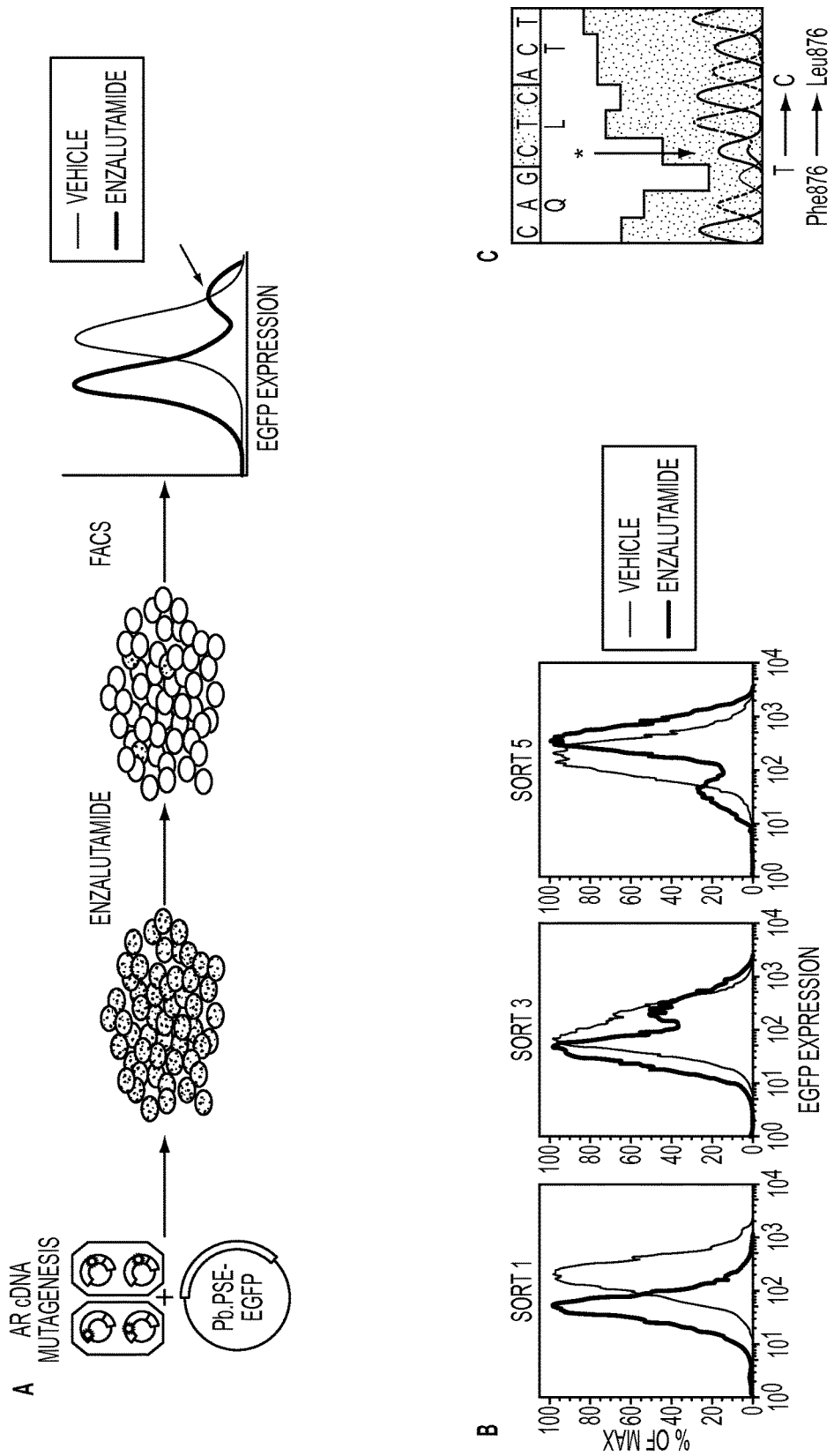
FIGS. 1A-1C show a mutagenesis screen for enzalutamide resistance to identify novel AR mutations. (A) Schematic diagram of AR mutagenesis screen strategy to identify enzalutamide resistance mutations. Briefly, cells are transduced with a randomly mutagenized AR cDNA library (in pWZL-AR) and EGFP reporter of AR activity (Pb.P-SE.EGFP), treated with 1 μM enzalutamide, and then EGFP-positive cells are sorted using fluorescence-activated cell sorting (FACS). AR was then PCR amplified and sequenced to identify relevant mutations. (B) FACS analysis histograms of LNCaP-Pb.PSE.EGFP mutant AR library cells after each of 5 subsequent sorts. After each sort, cells were expanded and a subset was treated with vehicle (dimethyl sulfoxide, DMSO) or 1 µM enzalutamide and subjected to FACS analysis for EGFP expression. (C) Sanger sequence trace of AR PCR product from cells after 5 rounds of enzalutamide treatment and FACS-sorting of EGFP-positivity. Genomic DNA was isolated from a subset of cells after each sort, the exogenous AR cDNA was PCR amplified, and then Sanger sequenced. Alignment was performed against AR wild-type using SeqMan (DNASTAR) and sequence traces were examined and captured using 4 Peaks.

Prior work with targeted therapies that inhibit oncogenic kinases has shown that unbiased mutagenesis screens can identify clinically relevant mutations that alter drug activity. To develop an analogous strategy for AR, a reporter-based mutagenesis screen was designed using the transcriptional activity of AR to discover mutations that confer resistance to enzalutamide. An AR-regulated EGFP reporter, with a probasin promoter and PSA enhancer elements driving EGFP expression (Pb.PSE-EGFP), was invoked to rapidly screen for and enrich cell populations bearing biologically active mutations (FIG. 1A).

Figure 6:
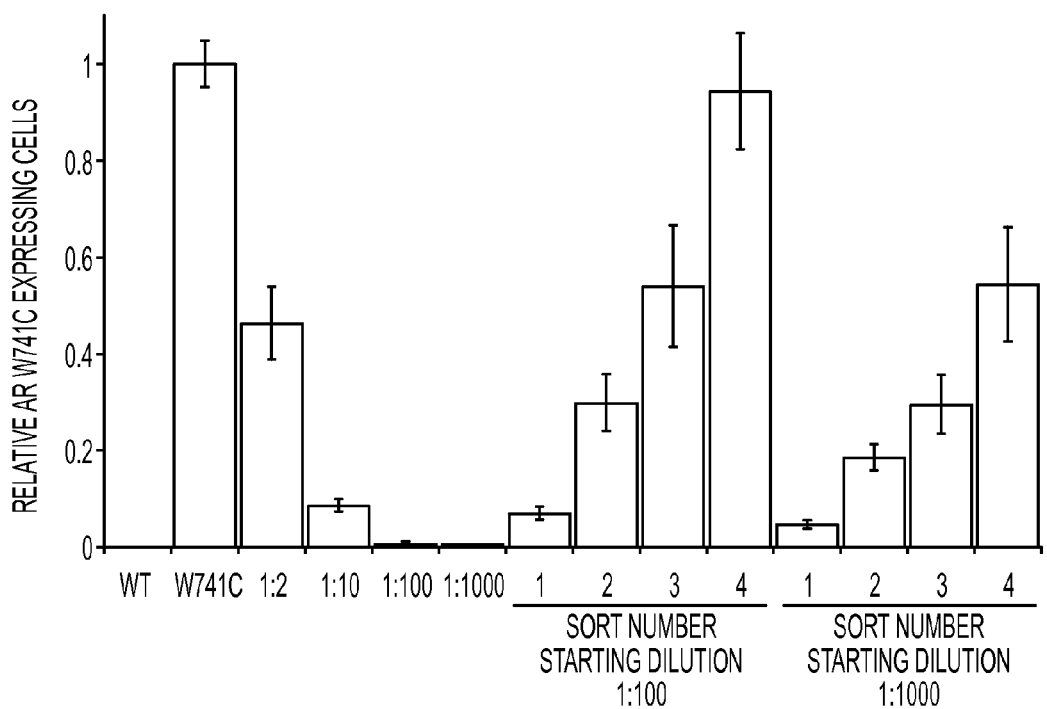
FIG. 6 shows enrichment of AR W741C mutant expressing LNCaP-Pb.PSE.EGFP cells after bicalutamide treatment and EGFP sorting. Genomic DNA was isolated from LNCaP-Pb.PSE.EGFP cells ectopically expressing either wild-type (WT) AR or mutant AR W741C, or different ratios of mutant-to-WT, and quantitative polymerase chain reaction (PCR) was performed to test the sensitivity of the W741C-specific primers. With starting ratios of 1:100 and 1:1000 mutant-to-WT, treated these cell mixtures with 1 µM bicalutamide were treated for 4 days, and those that maintained/induced EGFP expression were FACS sorted.

Proof-of-concept studies were conducted with LNCaP cells co-transduced with Pb.PSE-EGFP and AR W741C, a well-characterized mutation that converts the AR antagonist bicalutamide into an agonist. With a starting ratio of 1:100 or 1:1000 cells overexpressing AR W741C to wild-type AR respectively, cells were sorted with FACS that maintained EGFP expression after acute bicalutamide exposure. After 4 rounds of bicalutamide "selection" and sorting, LNCaP-AR cells expressing W741C overwhelmingly dominated the final population (FIG. 6).

Figure 8:
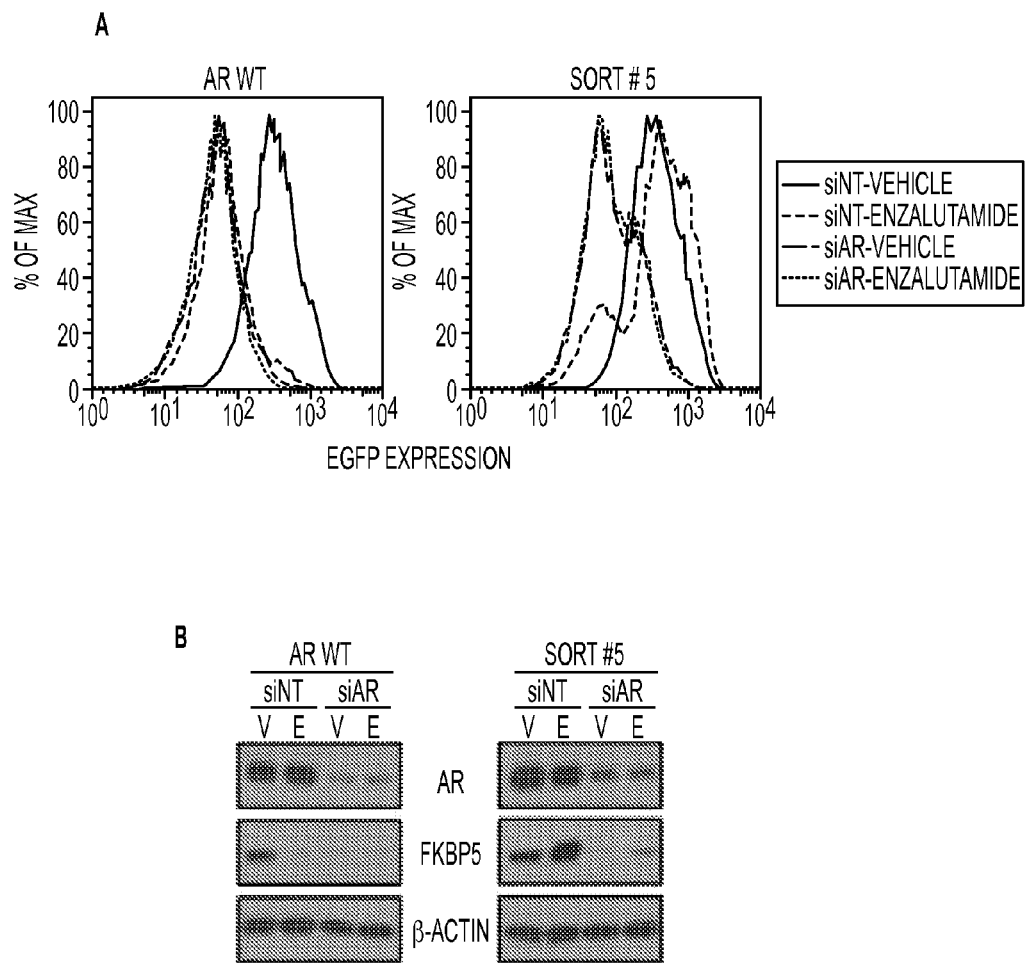

An enzalutamide resistance screen was then conducted with a Pb.PSE-EGFP reporter and a randomly mutagenized AR library. After five iterations of enzalutamide exposure and FACS sorting, a population of cells with durable EGFP expression was identified (FIG. 1B). Moreover, enzalutamide promoted AR transcriptional activity in these cells, reflected by induction of EGFP expression compared to vehicle control (FIG. 1B). Analysis of endogenous AR target gene expression confirmed that enzalutamide behaved as an agonist in the enriched cell population (FIG. 7), and siRNA knockdown of AR showed that these pharmacologically induced changes remained AR-dependent (FIG. 8).

To identify AR mutations in these cells, the exogenously expressed AR cDNA was amplified and the PCR product was Sanger sequenced. In two of three replicates, a single dominant point mutation emerged, resulting in the amino acid substitution F876L (FIG. 1C). Importantly, this mutation progressively enriched throughout the selection process (FIG. 9).

Figure 2:
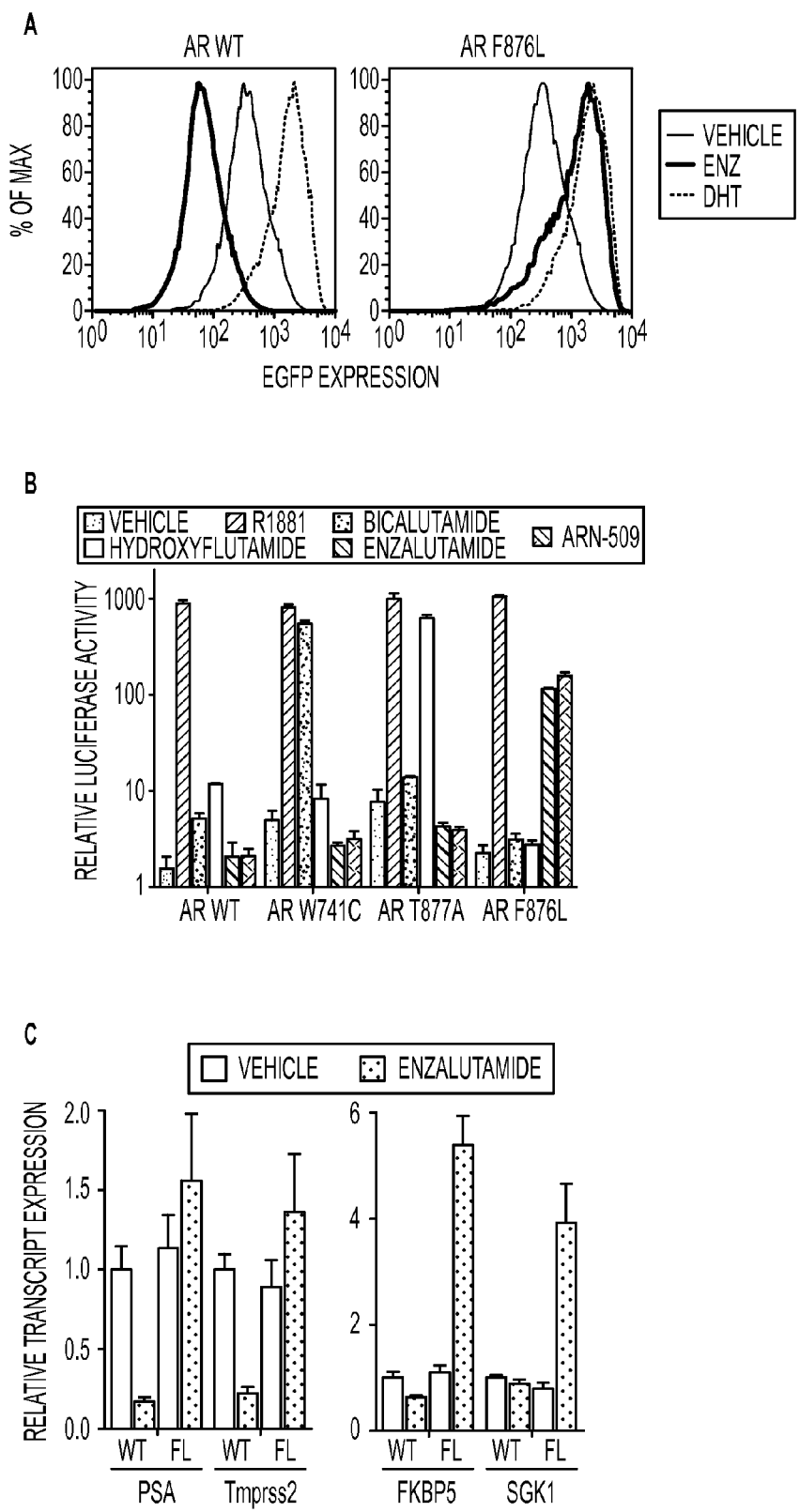
FIGS. 2A-2F demonstrate that AR F876L mutation converts enzalutamide into an agonist and rescues enzalutamide-induced growth inhibition. (A) EGFP reporter of AR F876L activity. LNCaP-Pb.PSE.EGFP cells were engineered to overexpress either AR WT or AR F876L, treated with vehicle (DMSO), 10 µM enzalutmide or 1 nM dihydrotestosterone (DHT), and FACS analysis performed for EGFP expression. Mean fluorescence intensity for WT treated cells: vehicle, enzalutmide, DHT; for F876L cells: vehicle, enzalutamide, DHT. (B) Luciferase reporter of AR F876L activity. CV1 cells were cotransduced with ARE(4X)-firefly luciferase construct, an SV40 Renilla luciferase construct, and one of the following AR constructs: wild-type (WT) AR, AR T877A, AR W741C, or AR F876L, then treated with vehicle, 10 µM antiandrogens, or 1 nM R1881. A dual luciferase assay was conducted on cell lysates, normalizing firefly to Renilla luciferase, and relative light units (RLUs) shown. (C) Quantitative reverse transcription-polymerase chain reaction (qRT-PCR) analysis of AR target genes (PSA, Tmprss2, SGK1, and FKBP5) in LNCaP cells ectopically expressing either wild-type AR or AR F876L in full-serum containing media. Cells were treated with either vehicle (DMSO) or 1 µM enzalutamide for 24 hours (normalized to GAPDH mRNA, mean±SD, n=3) (D) Enzalutamide-induced growth inhibition in VCaP cells is reversed by expression of AR F876L. VCaP cells overexpressing either AR WT or AR F876L were cultured in full-serum containing media, treated with either vehicle (DMSO) or 10 µM enzalutamide, and the viable cell fraction was determined by CellTiter-GLO (mean±SD, n=3). (E) Enzalutamide rescues the growth of VCaP cells expressing AR F876L in androgen-depleted media. VCaP cells overexpressing either AR WT or AR F876L were cultured in androgen-depleted media, treated with either vehicle (DMSO) or 10 µM enzalutamide, and the viable cell fraction was determined by CellTiter-GLO (mean±SD, n=3). (F) Time to progression of a xenograft model of CRPC ectopically expressing AR F876L. LNCaP/AR cells ectopically expressing either AR WT or AR F876L were grafted into SCID mice and the mice dosed with either vehicle or 30 mg/kg enzalutamide (in 0.5% hydroxy-methyl-propyl-cellulose). Mice were monitored for tumor establishment and once they were palpable, were measured weekly (10 tumors per treatment group).
Figure 2:
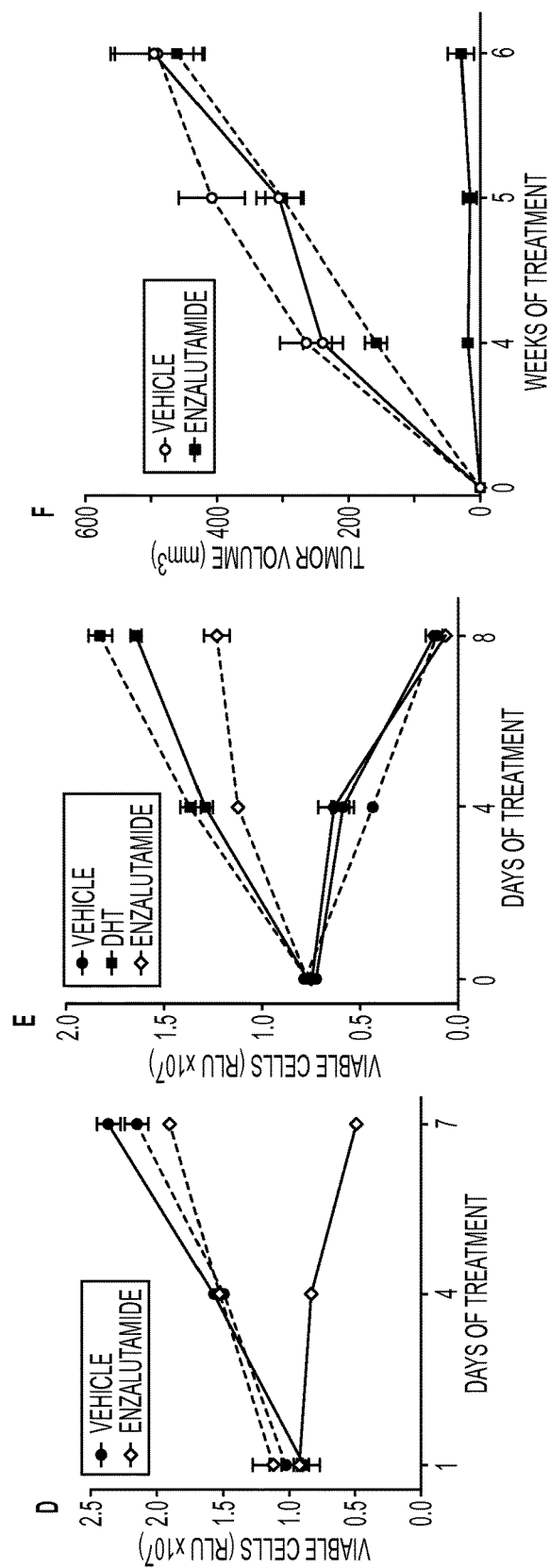
Figure 11:
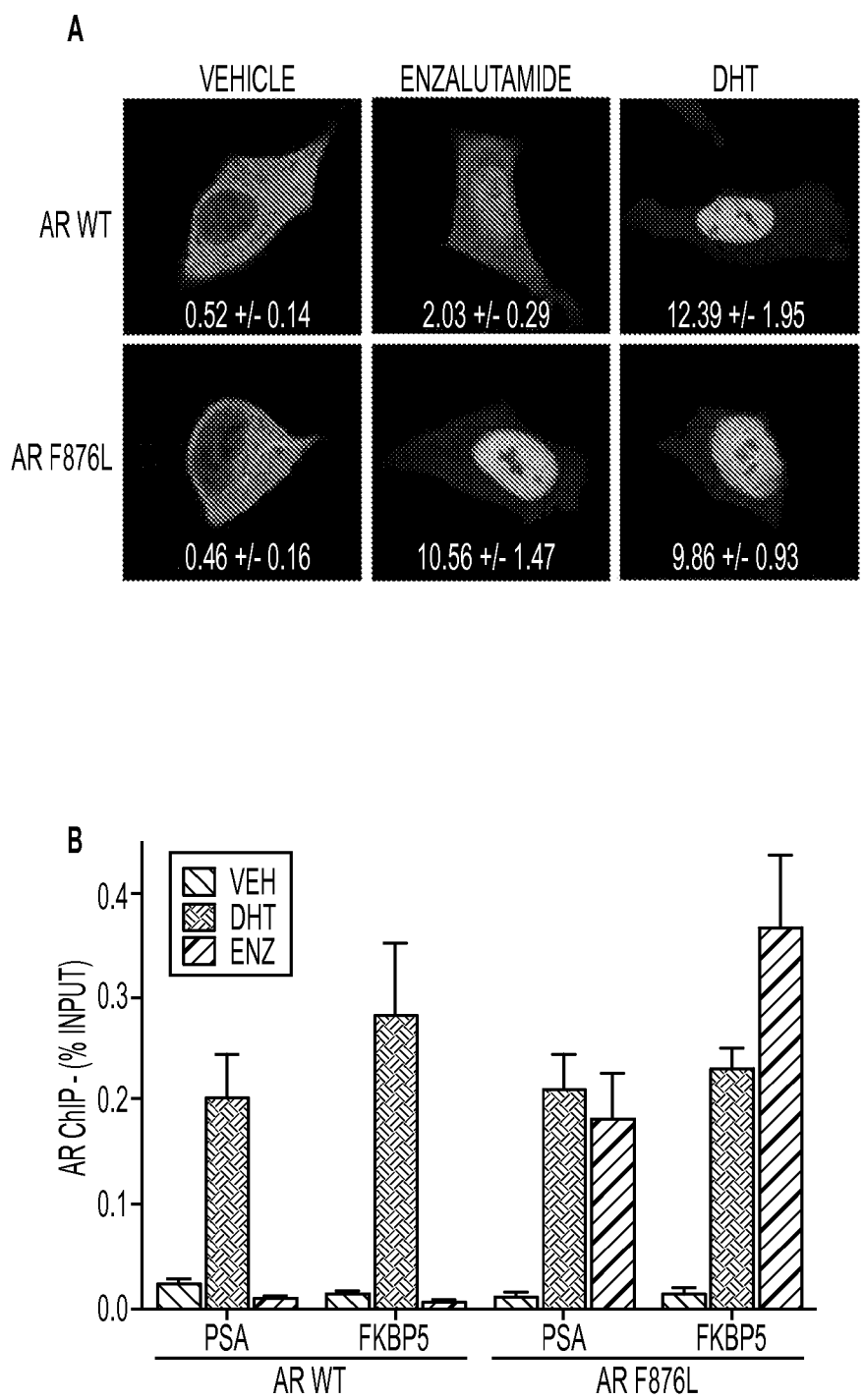

To validate the results of the screen, an F876L vector was engineered and transduced into parental LNCaP cells expressing the Pb.PSE-EGFP reporter. Treatment of these cells with enzalutamide resulted in a dose-dependent induction of EGFP expression (FIGS. 2A and 10). AR F876L cDNA was introduced into AR-negative CV1 cells along with an AR-dependent luciferase construct, and upon enzalutamide treatment, luciferase activity was induced ~50-fold (FIG. 2B). These results were comparable to those seen with the previously reported AR mutations T877A and W741C, which confer agonism to hydroxyflutamide and bicalutamide respectively. Also, enzalutamide treatment potently induced nuclear localization of AR F876L (FIG. 11), and chromatin immunoprecipitation studies showed that enzalutamide promoted AR F876L recruitment to the enhancers of AR target genes (FIG. 11). In line with these results, endogenous AR target genes were either unaffected or strongly induced by enzalutamide in cells expressing AR F876L (FIG. 2C). Notably, F876L similarly impacted the pharmacology of ARN-509, a structurally discrete antiandrogen nevertheless sharing the bisaryl-thiohydantoin core motif (FIGS. 2B and 12).

Figure 13:
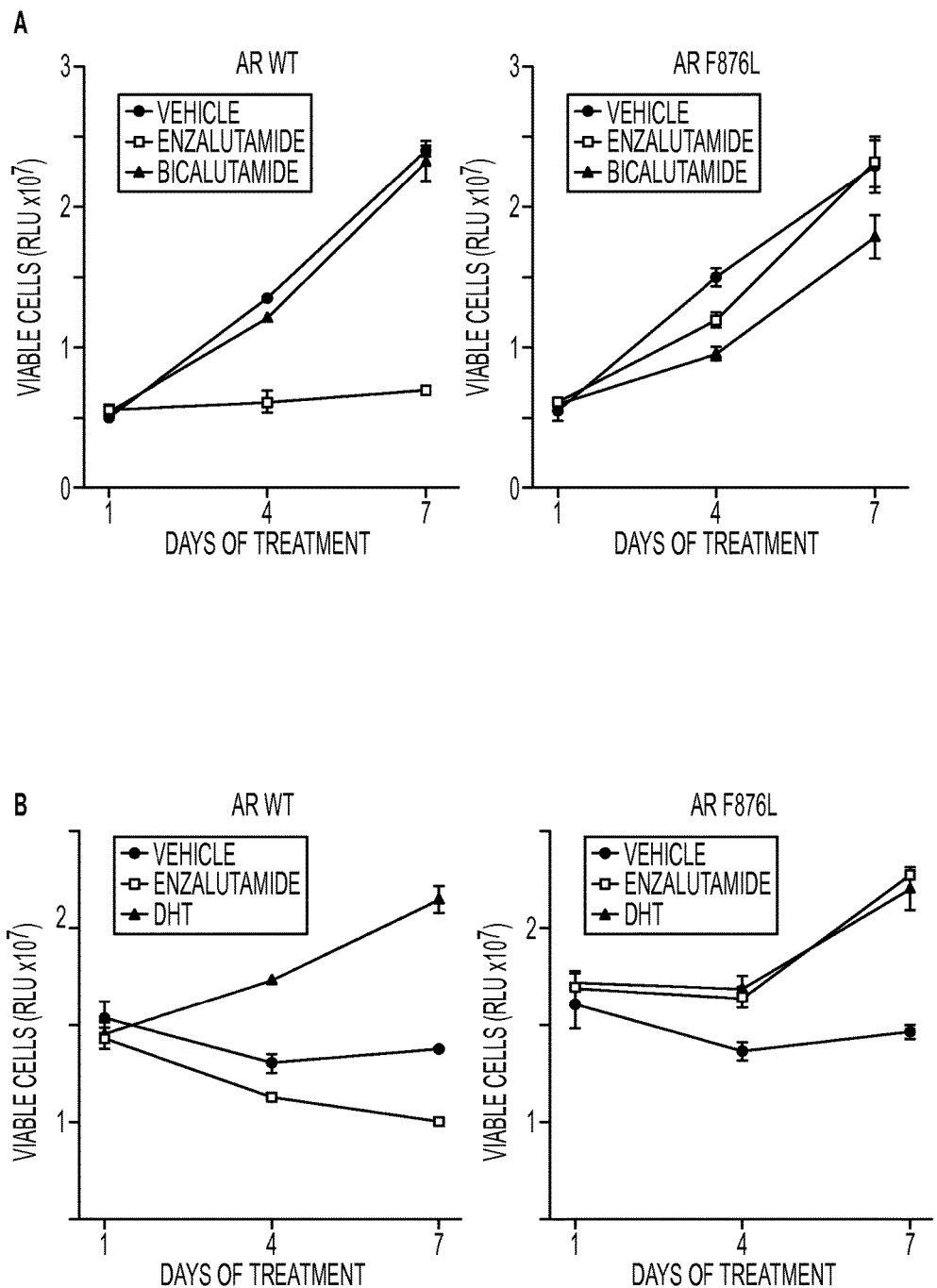

In vitro growth assays were conducted to examine the consequences of AR F876L expression on enzalutamide sensitivity in prostate cancer cell lines. Although enzalutamide treatment potently inhibits the growth of parental VCaP cells, overexpression of AR F876L entirely reversed this phenotype (FIG. 2D). Enzalutamide also rescued the growth of VCaP/AR F876L cells in androgen depleted media to an extent commensurate with the exogenous androgen DHT (FIG. 2E). These results were recapitulated in CWR22PC cells, another prostate cancer cell line that is very sensitive to enzalutamide (FIG. 13).

In vivo, LNCaP/AR cells overexpressing either wild-type or F876L mutant AR were grafted subcutaneously into castrate SCID mice and time to tumor progression was determined in the presence or absence of the drug. While the growth of wild-type AR tumors was almost completely inhibited by enzalutamide treatment, tumors expressing AR F876L grew rapidly in the presence of enzalutamide, similar to vehicle treated tumors of either genotype (FIG. 2F).

To determine whether human prostate cancer models that acquired spontaneous resistance to enzalutamide therapy also harbored the F876L mutation, CWR22PC cells were cultured in vitro with enzalutamide for several months. Nearly 50% of the cells expressed the F876L mutation (FIG. 5). Prolonged culture of these cells with ARN-509 also selected for a small population expressing AR F876L. In vivo, long-term enzalutamide or ARN-509 therapy in mice bearing LNCaP/AR xenograft tumors resulted in the outgrowth of tumor cell populations expressing AR F876L. Sequencing revealed that AR F876L predominated in one tumor (~50%), and was present at low frequency in four other tumors (~1-2%), and that a distinct amino acid substitution at this residue, F876I, enriched in one in one enzalutamide-resistant tumor (Table 8).

TABLE 8

F876 mutation frequency in drug-resistant LNCaP/AR tumors

| Treatment | Frequency | Mutation | endogenous or exogenous locus |
|---|---|---|---|
| Enzalutamide | 1.06% | F876L | exogenous |
| Enzalutamide | 1.82% | F876L | exogenous |
| Enzalutamide | 2.19% | F876I | exogenous |
| ARN-509 | 1.10% | F876L | exogenous |
| ARN-509 | 1.39% | F876L | exogenous |
| ARN-509 | 71.23% | F876L | endogenous |

Figure 14:
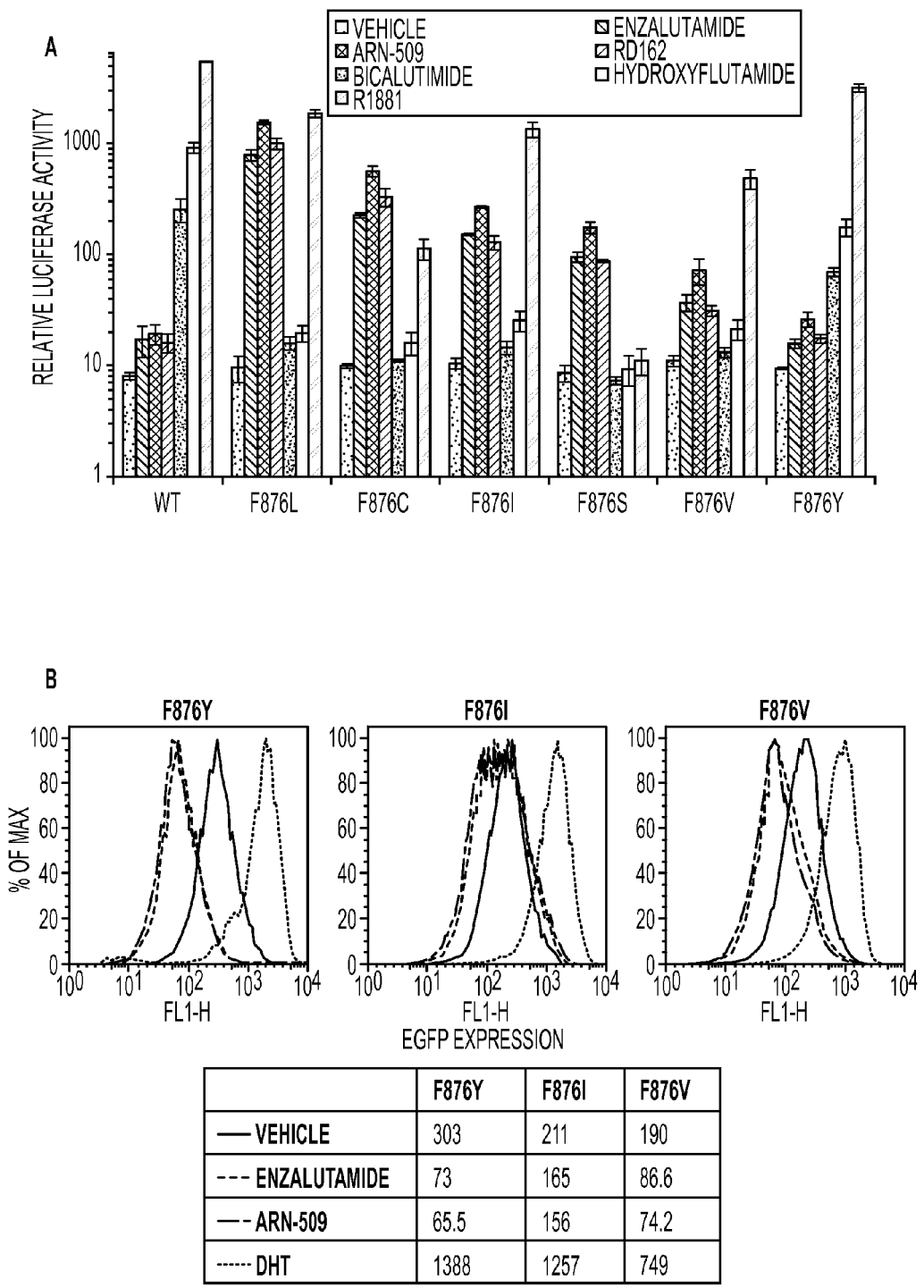

To further explore the function of Phe876 as the "gateway" residue governing enzalutamide and ARN-509 pharmacology, site-directed mutagenesis was used to make additional amino acid substitutions at residue 876, and tested their impact on enzalutamide and ARN-509 pharmacology. While one conservative substitution, F876Y, did not change either drug's pharmacology, other conservative substitutions F876 with aliphatic side chains, F876I and F876V, conferred modest agonism to both enzalutamide and ARN-509 (FIG. 14).

The results presented herein demonstrate that F876L dramatically impacts the pharmacology of enzalutamide and ARN-509. This finding that a clear structural change in the drug-receptor complex might be occurring. Structural modeling studies were performed to understand the impact of F876L on the antagonism-to-agonism conversion. Because a crystal structure depicting AR bound to an antagonist does not yet exist, structural modeling using ligand docking and molecular dynamics simulations were performed. In designing the study, it was noted that both enzalutamide and ARN-509 share identical A rings with the bicalutamide-like AR agonist S1 (FIG. 3A), which was effectively co-crystallized with the LBD of AR in an agonist conformation (PDB, FIG. 3B). Consequentially after an initial quantum-mechanical geometry optimization of the small molecules (FIG. 3C), the mutually shared A rings were overlaid with bicalutamide's, and 10 ns molecular dynamics simulations were performed with each drug independently docked into AR WT or AR F876L.

Figure 3:
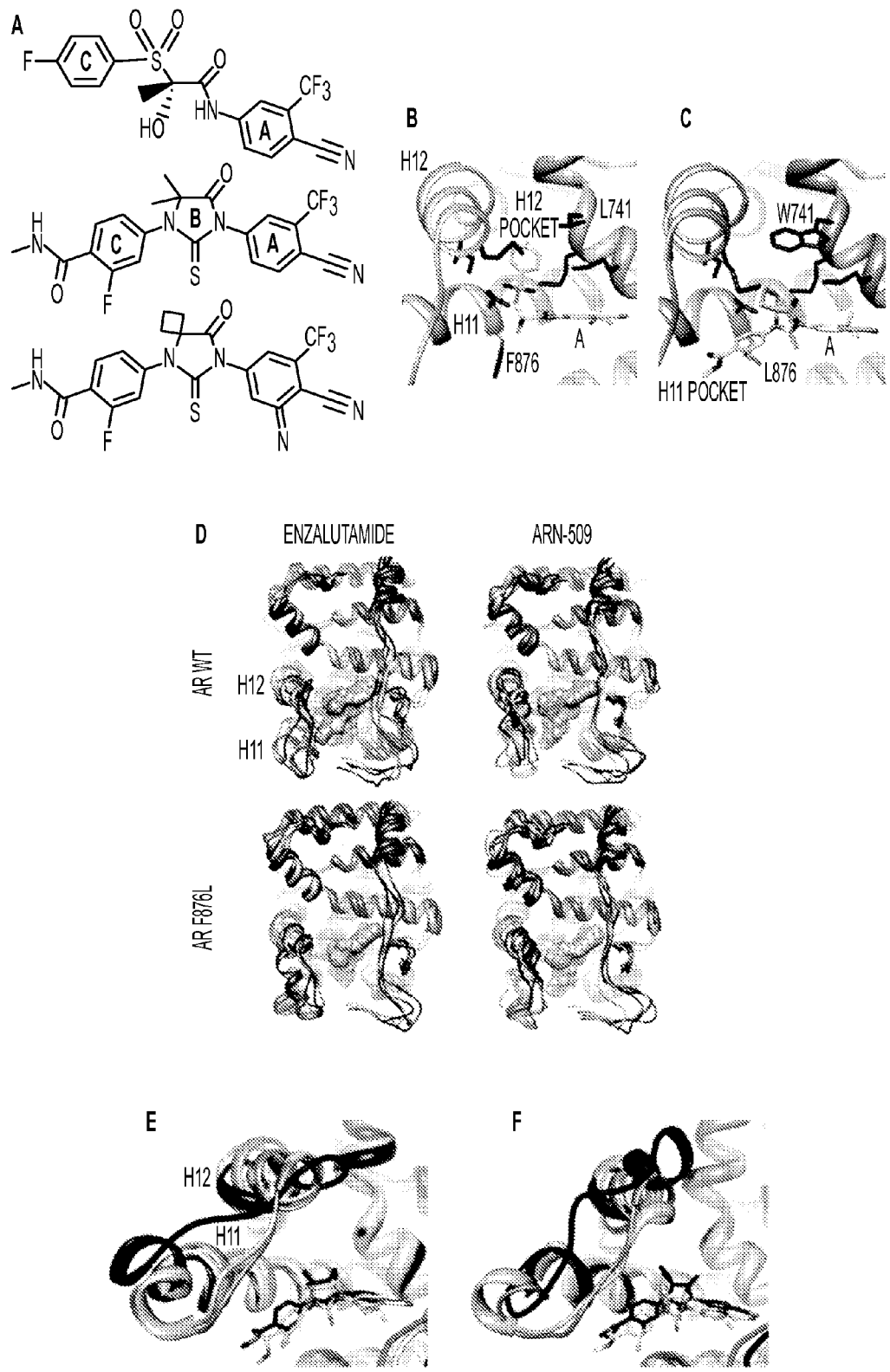
FIGS. 3A-3F shows that molecular dynamics simulations predict a novel binding mode for bisaryl-thiohydantoin antiandrogens and the basis for agonism in AR F876L. (A) Structures of the antiandrogens bicalutamide (top), MDV3100 (middle), and ARN-509 (bottom) oriented to highlighted the common and discrete regions of the molecules. The A-C annotation of the rings and the number system used for the atoms on the B ring is indicated. (B) A magnified view of the co-crystal structure of AR W741L (grey) and bicalutamide (yellow) shows the antiandrogen's spatial relationship to F876 (blue). In this agonist conformation, the C ring of bicalutamide occupies a region of the AR LBD distal to F876 (the "H12 pocket"). (C) A magnified view of the energy-minimized models of enzalutamide (yellow) and ARN-509 (cyan) calculated using coordinates from 1Z95 in which residue 741 is a tryptophan. The model suggests that the loss of torsional freedom imposed by the B ring of enzalutamide and ARN-509 imposes conformational restrictions that direct the C-ring of the antagonists towards F876 and the H11 pocket. (D) The coordinates for three 10 ns simulations with the indicated receptor (cyan) and drug compound (gold) were overlaid on the 1Z95 structure (grey) to highlight structural differences between the agonist-like conformation of the AR W741L/bicalutamide complex. Note the evidence of H12 dislocation in AR WT/antiandrogen complexes that is less evident for AR F876L. Bicalutamide was deleted for visual clarity. (E) The lowest energy MD simulations for enzalutamide with AR WT (red) and AR F876L AR (cyan) are overlaid on 1Z95 (grey), and suggest how the F876L mutation allows H11 and H12 to adopt a more agonist-like conformation. (F) An analogous view of the lowest energy MD simulations for ARN-509 with AR WT AR (red) and AR F876L (cyan) overlaid on 1Z95 (grey) shows a similar effect for F876L on the positioning of H11 and H12. These simulations also point to the comparatively larger dislocation in H12 by ARN-509 in AR WT, presumably owing to favorable steric clashes between the spiro-cyclobutyl ring and H12.

The docked enzalutamide and ARN-509 molecules demonstrated strikingly different interaction patterns with AR compared to bicalutamide (FIG. 3B-C). Notably, the torsional restrictions imposed by the thiohydantoin B-ring prevents the compound from accessing the "H12 pocket" occupied by bicalutamide and instead forces the C-ring to bind a region near the C terminus of helix 11 and the loop connecting helices 11 and 12. Accommodation of the C-ring in this region is coupled to significant conformational rearrangements of residues on H11 and the H11-H12 connecting loop that prevents H12 from adopting the agonist conformation required for efficient co-activator recruitment. To investigate how the F876L mutation might alleviate antagonism we performed similar MD simulations using the F876L receptor. The results presented herein demonstrate that despite inducing similar dislocations in the H11 pocket the mutation allows the receptor to reposition H12 in a more agonist-like conformation that is compatible with co-activator recruitment (FIG. 3D). Importantly, these structural modeling results are consistent with the differential resistance profiles involving residues 741 and 876 (FIG. 2B).

Another notable insight from these simulations was that the substituent on the 3 position of the B ring (i.e. the germinal dimethyl group on enzalutamide, the spiro-cyclobutyl ring on ARN-509) was predicted to lie in close proximity to residues on H12 and the loop between H11, 12 in the mutant receptor. This observation argued strongly that a compound capable of further antagonizing this H12 positioning might behave as an antagonist for AR F876L.

Since the residues near the B rings of enzalutamide and ARN-509 are generally hydrophobic, it was speculated that installing a larger hydrophobic moiety at the 3 position on the B ring could encourage H12 on AR F876L to shift away from the agonist conformation. This hypothesis was in part supported by a visual comparison of the MD simulations for ARN-509 and enzalutamide as the bulkier spiro-cyclobutyl moiety on ARN-509 elicited greater H12 displacements than did enzalutamide's gem-dimethyl group (FIG. 3D).

To test these considerations, a series of analogues bearing saturated hydrocarbon spirocycles of incrementally greater size and complexity at the 3 position of the B ring on the enzalutamide scaffold (DR100-103, FIG. 4A) were designed and synthesized. Owing to the apparent sensitivity of AR to the size and orientation of the B ring substituents, it was reasoned that the restricted conformation of these "D" rings would engender a systematic analysis of the proposed pharmacological model. Moreover, prior medicinal chemistry had shown that discrete bisaryl-thiohydantoin compounds bearing similar D rings were effective antagonists of AR WT, indicating that the ligand binding pocket should tolerate the larger inhibitors designed.

Figure 4:
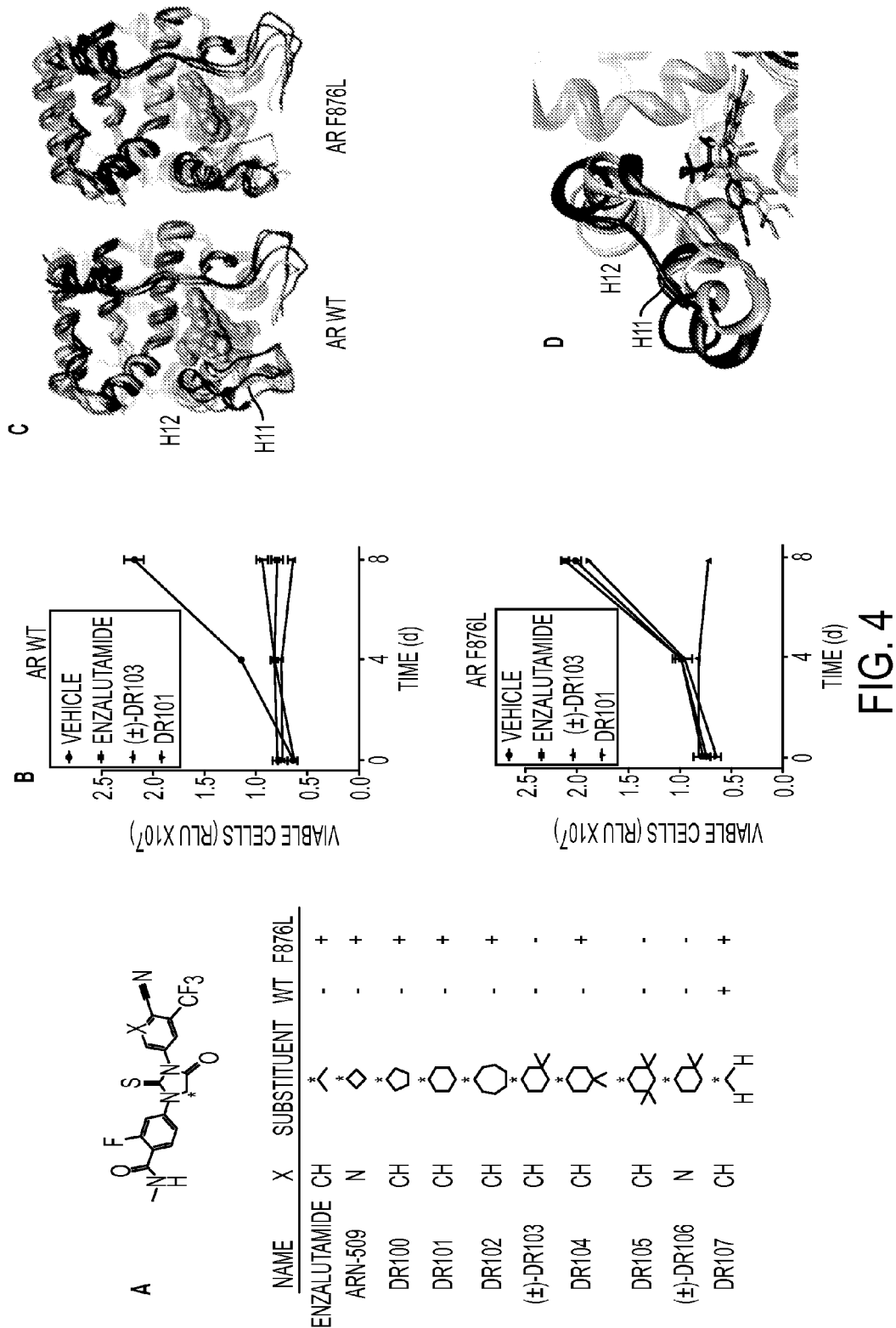
FIGS. 4A-4D show a focused chemical screen identifies novel antagonists of AR F876L. (A) A tabular summary of the bioactivity of the novel antiandrogens in the LNCaP/AR/Pb.PSE.EGFP cell-based assay shows the importance of a carefully designed D ring for competent inhibition of AR F876L. Agonism is indicated with a "-" symbol, and antagonism is indicated with a "+" sign. The asterisk is situated over the shared carbon atom that joins the bisaryl-thiohydantoin scaffold to the respective "substituent". The raw data is outlined in FIG. S# (B) A proliferation assay for VCaP prostate cancer cells overexpressing either wild-type AR (top) or AR F876L (bottom) shows that (+)-DR103 effectively inhibits the growth of both models, while enzalutamide and the close structural analogue DR101 only inhibit the growth of VCaP/AR WT. Data are reported as mean±SD, n=3. (C) An overlay of three 10 ns MD simulations for (S)-DR103 docked either in AR WT (left) or AR F876L (right) shows the dislocation of H12 in space compared to 1Z95 (grey), consistent with the pharmacological model predicted by prior MD simulations for enzalutamide and ARN-509 in AR WT. The predicted conformations of the AR variants are highlighted in cyan, and the respective conformations of (S)-DR103 are represented in gold. (D) A higher magnification view of the lowest energy conformations of enzalutamide (cyan), ARN-509 (gold), and (S)-DR103 (red) in complex with AR F876L highlights the dislocation of H12 and the loop between H11, 12 uniquely conferred by (S)-DR103. The color scheme invoked for AR F876L matches the respective antiandrogen.
Figure 15:
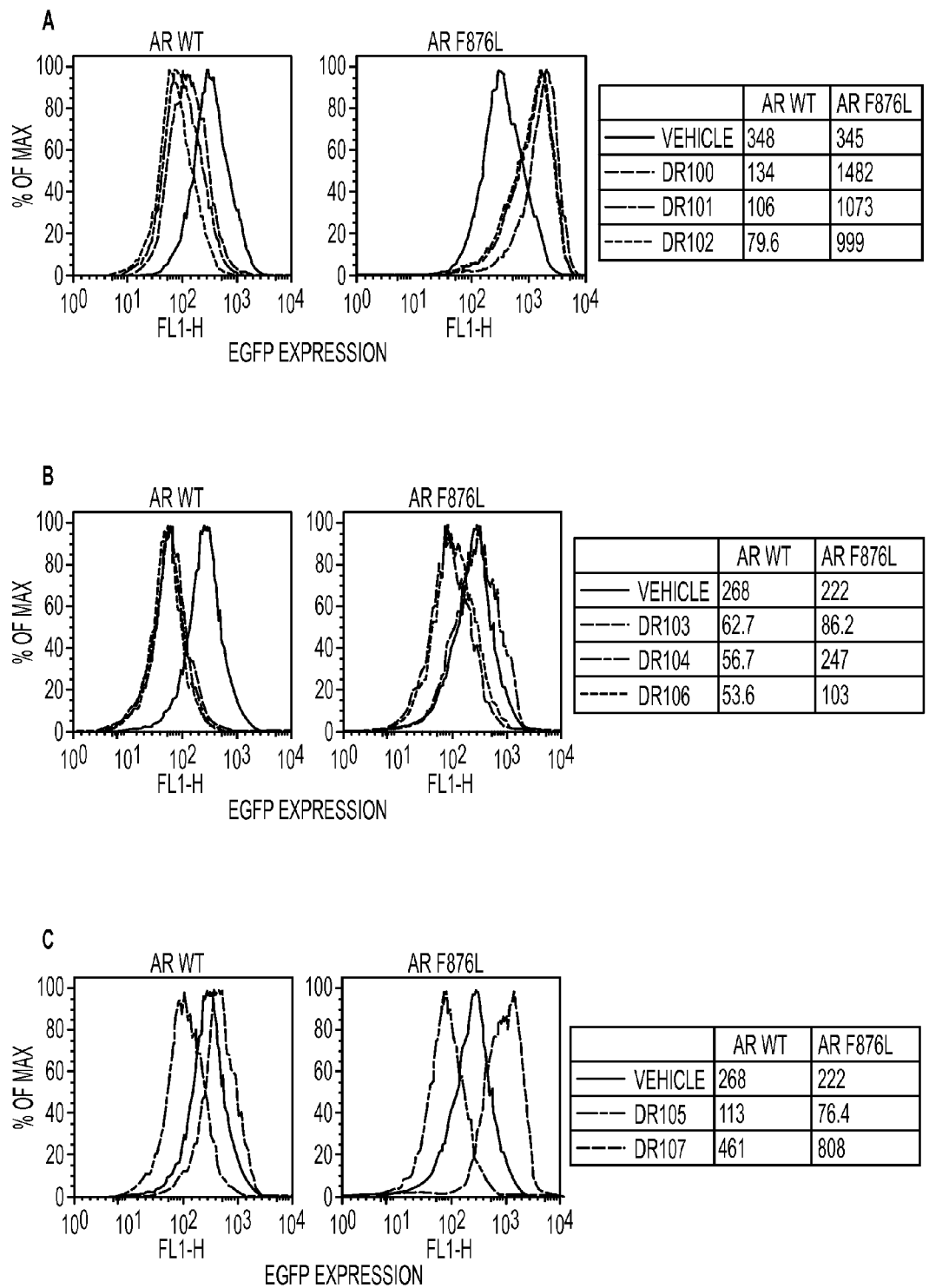

Consistent with this precedent, the DR100-103 series inhibited the transcriptional activity of AR WT in the EGFP reporter assay (FIGS. 4A and 15). Surprisingly, DR100-102 behaved as strong agonists for AR F876L (FIG. 15A), while (±)-DR103 potently inhibited AR F876L (FIG. 15B). This striking structure-activity relationship prompted us to empirically investigate the significance of the position of the gem-dimethyl group on the D ring of (±)-DR103. Remarkably, a compound with the gem-dimethyl group on the 4 (rather than 3/5) position of the D ring (DR104) was a modest agonist of AR F876L (albeit an antagonist of AR WT, FIG. 4A and FIG. S10B). Moreover, a compound with gem-dimethyl groups at the 3 and 5 positions of the D ring (DR105) inhibited AR F876L (and AR WT), further underscoring the biological importance of the steric clashes brought about by these moieties in the context of the mutant receptor. Encouragingly, transplanting the D ring from (±)-DR103 onto the ARN-509 scaffold [(±)-DR106] also resulted in AR F876L inhibition (FIG. 15B). We interpreted this result to be supportive of the model advanced by the prior MD simulations, as the F876L substitution appeared to impact the ability of enzalutamide and ARN-509 to induce H12 conformational choices of AR in a roughly equivalent manner. Finally, to underscore the importance of the interactions conferred by the D ring, DR107, a compound built on the enzalutamide scaffold bearing only hydrogen atoms at the 3 position on the B ring was synthesized. This molecule was an agonist both for AR WT and AR F876L (FIG. 15C), pointing directly to the pharmacological significance of interactions between H12, the loop between H11, H12, and the substituent at the 3 position of the B ring.

Consistent with this pharmacology, (±)-DR103 inhibited the growth of prostate cancer cell lines expressing both the WT and mutant receptor (FIG. 4B, FIG. 16). (±)-DR103 also inhibited endogenous AR signaling and induced PARP cleavage (FIG. 17). DR101, a close structural analogue that behaved as an agonist for AR F876L, did not inhibit cell growth at equivalent doses (FIG. 4B). Furthermore, the dose of (+)-DR103 required to observe antiproliferative effects (10 μM) did not impact the proliferation of DU145 (an AR null human prostate cancer cell line), supporting the specificity of the antiandrogen (FIG. 18).

Structural modeling studies for (±)-DR103 provided additional support for the molecular mechanism of AR WT antagonism presented herein. Unlike the results for enzalutamide and ARN-509 demonstrating corrected H12 positioning in the F876L receptor (FIG. 3D), MD simulations using (S)-DR103 suggested that an agonist-like conformation of H12 cannot be achieved for either WT or mutant AR (FIG. 4C). The modeling study instead showed that the D ring on (S)-DR103 was capable of directly displacing the N-terminal residues of H12 (FIG. 4D). Similar MD simulations for the complex of AR F876L and (R)-DR103 showed a slightly less pronounced H12 dislocation, suggesting that the two enantiomers might cause different levels of antagonism to AR F876L.

Example 2

Identification of Novel Androgen Receptor Mutations In Vitro

Cells and Cell Culture Conditions

CWR22Pc human prostate cancer cells were provided by Marja T. Nevalainen (Thomas Jefferson University) and were maintained under standard cell culture conditions in RPMI 1640 with 10% fetal bovine serum (FBS; Omega Scientific), penicillin-streptomycin, and 0.1 nM 5α-dihydrotestosterone (Sigma) in a final vehicle concentration of 0.1% dimethylsulfoxide (Fisher). Antiandrogens used in the study were bicalutamide (LKT Laboratories), MDV3100/enzalutamide, and ARN-509. Enzalutamide and ARN-509 were synthesized in house at MSKCC. Each of the three antiandrogens was used at a final concentration of 10 μM in 0.1% dimethylsulfoxide.

To derive androgen deprivation therapy (ADT) resistant cell strains, CWR22Pc were continuously treated with one of the three antiandrogens in two treatment protocols.

Treatment protocol #1 utilized the standard cell culture conditions. For treatment protocol #2, 10% charcoal-stripped fetal bovine serum (CSS; Omega Scientific) substituted for FBS and DHT was omitted. For treatment protocol #2, an additional group was treated with the vehicle 0.1% dimethylsulfoxide in lieu of antiandrogen. Treatment media was replaced every 4-5 days, and cells were passaged upon reaching confluence. The time between successive passages was recorded. Cell strains were designated as antiandrogen resistant when the time between consecutive passages was reduced to 4-6 days, which is a period of time equivalent to that of untreated CWR22Pc. Resulting cell strains were designated as follows:

TABLE 9

| Protocol # | Antiandrogen | Cell Strain Designation |
|---|---|---|
| 1 | bicalutamide | FDB |
|  | bicalutamide | B51-FDB |
|  | enzalutamide | FDM |
|  | ARN-509 | FDA |
| 2 | — | CV |
|  | bicalutamide | CB |
|  | enzalutamide | CM |
|  | ARN-509 | CA |

B51-FDB is an independently generated bicalutamide resistant strain generated with the same protocol.

Sequencing of Androgen Receptor

Total RNA was isolated from each of the CWR22Pc cell strains or untreated parental CWR22Pc using the TRIzol reagent protocol (Invitrogen). Purified RNA was treated with TURBO DNA-free (Invitrogen) and cDNA synthesis completed with Applied Biosystem's TaqMan RT-PCR reagents (Invitrogen). The ligand binding domain (exons 4-8) was amplified from cDNA by PCR using HotStar HiFidelity Polymerase (Qiagen). Forward and reverse primers (written 5' to 3') were TGTCCATCTTGTCGTCTTCG and CAGGCAGAAGACATCTGAAAG, respectively. The PCR product was gel purified with the High Pure PCR product purification kit (Roche), cloned into the pCR4-TOPO TA vector (Invitrogen), and transformed into One Shot TOP10 chemical competent E. coli. Plasmid DNA was isolated from transformed colonies using QIAprep Spin Miniprep kit (Qiagen). The cloned androgen receptor ligand binding domain was sequenced by Sanger sequencing (Genomics Core, MSKCC). Sequencing primers (written 5' to 3') flanking the cloning sites were ATTAACCCT-CACTAAAGGGA and GTAAAACGACGGCCAG. Forward and reverse strand androgen receptor primers for sequencing were CCAGATGGCTGTCATTCAGTA and AAGTAGAGCATCCTGGAGTTG, respectively. Sequence files from each clone were compiled and aligned with the human androgen receptor reference sequence NM_000044 (NCBI Blast) for identification of mismatched residues.

Results

TABLE 10

Identified codon-changing mutations

| Nucleotide Position | Change | Amino Acid change |
|---|---|---|
| 3175 | G to A | C686Y |
| 3213 | G to A | A699T |
| 3342 | A to G | M743V |
| 3430 | A to G | N771S |
| 3444 | C to T | H776Y |
| 3468 | T to C | C784R |
| 3727 | C to T | A871V |
| 3744 | T to C | F876L |
| 3846 | A to G | K910E |
| 3855 | C to T | P914S |

Example 3

Identification of Novel Androgen Receptor Mutations In Vivo

MDV3100 & ARN-509 Resistant LNCaP/AR Xenografts

Xenograft experiments in which AR mutations emerged after long-term treatment with second-generation antiandrogens were performed as follows: $2 \times 10^6$ LNCaP/AR cells (C. Tran et al., Development of a second-generation antiandrogen for treatment of advanced prostate cancer. Science 324, 787 (May 8, 2009)) were injected subcutaneously into the flanks of castrated SCID mice. Treatment with 30 mg/kg MDV3100 or ARN-509 (or vehicle) was initiated once tumors reached ~300 mm$^3$, resulting in rapid tumor regression. After several weeks of continual dosing, these tumors regain the ability to grow. Once these "resistant" tumors reached their original volume, the mice were sacrificed, and tumors collected for analysis. Vehicle treated tumors were also collected as controls.

Deep Sequencing of AR in LNCaP/AR Xenograft Tumors

Genomic DNA (gDNA) was isolated (PureGene Core Kit A, Qiagen) LNCaP/AR xenograft tumors. With 20 ng of gDNA as template, exons 4 through 8 of AR were individually PCR amplified with a proof-reading enzyme, Kapa HiFi Ready Mix (Kapa Biosystems, catalog # KK2612. RNA was extracted from LNCaP/AR xenograft tumors, reverse transcribed (High Capacity cDNA Reverse Transcription Kit, Applied Biosystems) and exons 2 through 8 of AR was PCR amplified using 200 ng cDNA as template (Qiagen, HotStar). PCR reactions were cleaned up with AMPure XP (Beckman Coulter Genomics) and pooled reaction yields were quantified using the Qubit fluorometer (Invitrogen). Library preparation was done using Nextera DNA Sample Preparation kit (Illumina, catalog # FC-121-1031) and run on the Illumina MiSeq sequencer using the 2×250 paired-end cycle protocol.

Genomic DNA was aligned to the hg19 build of the human genome using BWA (H. Li, R. Durbin, Fast and accurate short read alignment with Burrows-Wheeler transform. Bioinformatics 25, 1754 (Jul. 15, 2009)) with duplicate removal using samtools (H. Li et al., The Sequence Alignment/Map format and SAMtools. Bioinformatics 25, 2078 (Aug. 15, 2009)) as implemented by Illumina MiSeq Reporter. cDNA FASTQ files were processed with a windowed adaptive trimming tool sickle (github.com/najoshi/sickle) using a quality threshold of 32. The reads were then mapped to the human genome build hg19 with TopHat 2 (C. Trapnell, L. Pachter, S. L. Salzberg, TopHat: discovering splice junctions with RNA-Seq. Bioinformatics 25, 1105 (May 1, 2009)) using known AR transcripts NM_000044 and NM_001011645. Duplicates were then removed with Picard (picard.sourceforge.net). Variant detection was performed using VarScan 2 (D. C. Koboldt et al., VarScan 2: somatic mutation and copy number alteration discovery in cancer by exome sequencing. Genome Res 22, 568 (March, 2012)) with thresholds of a minimum of 10 supporting variant reads and variant allele frequencies of at least 1%.

Results

TABLE 11

Identified codon-changing mutations

| Nucleotide Position | Change | Amino Acid change |
|---|---|---|
| 2811 | G to A | E565K |
| 2880 | G to A | E588K |
| 2904 | G to A | A596T |
| 3057 | A to G | S648G |
| 3120 | G to A | E668K |
| 3162 | C to A | P683T |
| 3203 | C to A | D696E |
| 3295 | G to A | R727H |
| 3298 | A to T | N727I |
| 3327 | A to T | I738F |
| 3340 | G to T | W741L |
| 3341 | G to T | W741C |
| 3365 | G to A | G751S |
| 3744 | T to A | F876I |
| 3744 | T to C | F876L |

Example 4

Ligand Binding Studies

The relative binding affinity of DHT and MDV3100 in LNCaP cells ectopically expressing AR WT or AR F876L was determined using a competition assay in which increasing concentrations of cold competitor are added to cells pre-incubated with $^{18}$F-FDHT. The cells were propagated in RPMI media supplemented with 10% CSS (charcoal-stripped, dextran-treated fetal bovine serum). Cells were trypsinized, washed in PBS, and triplicate cell samples were mixed with 20,000 cpm $^{18}$F-FDHT and increasing amounts of cold competitor (0.1 nM to 10 µM). The solutions were shaken on an orbital shaker at ambient temperature, and after 1 hour the cells were isolated and washed with ice-cold Tris-buffered saline using a Brandel cell harvester (Gaithersburg, Md.). All the isolated cell samples were counted using a scintillation counter, with appropriate standards of total activity and blank controls, and the specific uptake of $^{18}$F-FDHT determined. These data were plotted against the concentration of the cold competitor to give sigmoidal displacement curves. The IC$_{50}$ values were determined using a one site model and a least squares curve fitting routine (Origin, OriginLab, Northampton, Mass.) with the $R^2$ of the curve fit being >0.99.

The data presented in FIG. 19 show that DHT binds to both AR WT and AR F876L expressing cells at a comparable $IC_{50}$. However, MDV3100 is able to displace $^{18}$F-FDHT from the mutant AR F876L cells at a lower $IC_{50}$ than for AR WT cells, suggesting a higher binding affinity of MDV3100 to the AR F876L mutant. The data presented herein are in line with previous data that showed the mutant AR T877A, which confers agonism on the antiandrogen hydroxyflutamide, binds to hydroxyflutamide (and several other hormones) with a higher affinity than to AR WT(M. S. Ozers et al., The androgen receptor T877A mutant recruits LXXLL and FXXLF peptides differently than wild-type androgen receptor in a time-resolved fluorescence resonance energy transfer assay. *Biochemistry* 46, 683 (Jan. 23, 2007)).

Example 5

AR Activity and Expression

As described in Example 1, AR negative CV1 cells expressing the indicated AR cDNA (or GFP as a control) were cultured in androgen depleted media and exposed to 10 μm of the indicated antiandrogen or 1 nM DHT. Luciferase activity was measured as described above and the data are presented in FIG. 20. Additionally, EGFP reporter assays of AR activity in cells expressing the indicated AR mutants were performed and the data are presented in FIG. 21A and FIG. 21B. LNCaP/Pb.PSE.EGFP cells were cultured in androgen containing media and treated with either vehicle (Veh), 10 μM antiandrogen or 1 nM DHT. Western blots of LNCaP/Pb.PSE.EGFP cells expressing the indicated AR mutants were cultured in media containing FBS are presented in FIG. 22.

Analysis of the AR mutants isolated from drug resistant LNCaP/AR xenograft tumors, via the luciferase reporter assay, indicate that none of the mutants conferred agonism on either MDV3100 (enzalutamide) or ARN-509. Additionally, the data from the EGFP reporter assay show that all of these mutants still remained sensitive to enzalutamide and ARN-509. Western blot data indicated that all of the mutants were expressed at comparable levels in LNCaP/Pb.P-SE.EGFP cells. Also, these results indicate that compared to wild-type, some of these mutants altered the responsiveness of the receptor to DHT.

In a similar luciferase assay, AR negative CV1 cells expressing the indicated AR cDNA were cultured in androgen depleted media and exposed to 10 μm of the indicated antiandrogen, 100 nM Dexamethasone or 1 nM DHT and the data are presented in FIG. 23. Additionally, LNCaP/Pb.P-SE.EGFP cells were cultured in androgen containing media and treated with either vehicle (Veh), 10 μM antiandrogen or 1 nM DHT and the data are presented in FIG. 24. Western blots of LNCaP/Pb.PSE.EGFP cells expressing the indicated AR mutants were cultured in media containing either FBS or CSS are presented in FIG. 25, while Western blots of CWR22Pc cells stably overexpressing the indicated AR mutants, cultured in media containing either CSS or FBS are presented in FIG. 26. FIG. 27A and FIG. 27B present qRT-PCR data from LNCaP/Pb.PSE.EGFP cells expressing the indicated AR mutants. The cells were cultured in CSS containing media and treated with either vehicle (DMSO), 10 μM antiandrogen, or 1 nM DHT and RNA was collected 24 hours later. FIG. 28A and FIG. 28B present qRT-PCR data from LNCaP/Pb.PSE.EGFP cells expressing the indicated AR mutants. The cells were cultured in CSS containing media and treated with either vehicle (DMSO), 10 μM antiandrogen, or 1 nM DHT and RNA was collected 24 hours later.

Analysis of the AR mutants isolated from drug resistant CWR22Pc cells, as well as further analysis of A597T from resistant LNCaP/AR xenograft tumors, indicate that P893S conferred agonism on Bicalutamide, comparable to the previously described W742C mutant; this P893S mutant also lost DHT responsiveness. These data also suggest that all of these mutants still remained sensitive to enzalutamide and ARN-509 (as shown in the EGFP reporter assay & qRT-PCR), although to variable degrees and with gene-specific differences. Finally, Western blot analysis showed that these mutants are not expressed at comparable levels in LNCaP/Pb.PSE.EGFP or CWR22Pc cells; in particular C687Y and C687Y/H875Y were expressed at lower levels. This may indicate that the cells could not tolerate high expression of these mutants. The EGFP reporter assay showed that these mutants had a higher basal level of AR activity.

EQUIVALENTS

Those skilled in the art will recognize, or be able to ascertain using no more than routine experimentation, many equivalents to the specific embodiments of the invention described herein. The scope of the present invention is not intended to be limited to the above Description, but rather is as set forth in the following claims:

What is claimed is:

1. In a method of treating castration resistant prostate cancer in a patient the improvement that comprises:
    monitoring response of the patient to an administered course of therapy by comparing at least first and second detected presence or expression levels, determined at first and second time points, respectively, the second time point being alter the first time point, of a nucleic acid sequence that encodes a variant androgen receptor or portion thereof having an amino acid sequence containing a mutation at amino acid 876 relative to a reference androgen receptor polypeptide of SEQ ID NO: 1, wherein the mutation at amino acid 876 is F876I, F876L, or F876V, and
    continuing to administer the course of therapy if the second detected presence or expression level is lower than the first detected presence or expression level, or administering a different course of therapy if the second detected presence or expression level is not lower than the first detected presence or expression level.

2. A method of treating castration resistant prostate cancer, the method comprising a step of:
    administering an optimized castration resistant prostate cancer treatment to a patient undergoing a course of treatment for prostate cancer, wherein:
        the patient's response to the course of treatment has been determined by:
            detecting in a first sample from the patient taken at a first time point before or during the course of treatment, a first level of a nucleic acid sequence that encodes a variant androgen receptor or portion thereof having an amino acid sequence containing a mutation at amino acid 876 relative to a reference androgen receptor polypeptide of SEQ ID NO:1, wherein the mutation is F876I, F876L, or F876V;
        detecting in a second sample from the patient taken at a second time point, later than the first time point and during the course of treatment, a second level of the nucleic acid sequence; and
        comparing the first and second detected levels; and
        determining that the course of treatment is the optimized castration resistant prostate cancer treatment if the second level is reduced relative to the first level or that an alternative course of treatment is the optimized castration resistant prostate cancer treatment if the second level is not reduced relative to the first level.

3. A method of treating castration resistant prostate cancer, the method comprising:
    administering to a patient suffering from castration resistant prostate cancer a treatment selected by a process comprising steps of:

detecting expression level of a nucleic acid sequence that encodes a variant androgen receptor or portion thereof having an amino acid sequence containing a mutation at amino acid 876 relative to a reference androgen receptor polypeptide of SEQ ID NO: 1, wherein the mutation at amino acid 876 is F876I, F876L, or F876V in samples obtained from at least first and second time points from a patient undergoing a course or treatment for prostate cancer;

determining if the patient has a positive response to the course of treatment by comparing the detected expression level at the at least first and second time points;

selecting the treatment as appropriate in light of the determining.

4. A method of treating castration resistant prostate cancer, the method comprising a step of:

administering a castration resistant prostate cancer treatment to a patient suffering from prostate cancer that has been determined to contain or express a nucleic acid sequence that encodes a variant androgen receptor or portion thereof having an amino acid sequence containing a mutation at amino acid 876 relative to a reference androgen receptor polypeptide of SEQ ID NO: 1, wherein the mutation at amino acid 876 is F876I, F876I or F876V, which prostate cancer treatment comprises administration of an agent that has been determined, when contacted with a population of cells expressing the variant androgen receptor or portion thereof, to decrease expression or activity of the variant androgen receptor ur portion thereof relative to that observed under comparable conditions absent the agent.

* * * * *

UNITED STATES PATENT AND TRADEMARK OFFICE
CERTIFICATE OF CORRECTION

PATENT NO. : 10,206,911 B2
APPLICATION NO. : 14/438399
DATED : February 19, 2019
INVENTOR(S) : Minna D. Balbas, Charles L. Sawyers and Philip Watson Page 1 of 1

It is certified that error appears in the above-identified patent and that said Letters Patent is hereby corrected as shown below:

In the Claims

Column 95, Claim 1, Line 45, please delete "patient" and insert --patient,-- therefor.

Column 95, Claim 1, Line 50, please delete "alter" and insert --after-- therefor.

Column 97, Claim 3, Line 9, please delete "or" and insert --of-- therefor.

Column 98, Claim 4, Line 9, please delete "F876I, F876I or F876V," and insert --F876I, F876L, or F876V,-- therefor.

Column 98, Claim 4, Line 14, please delete "ur" and insert --or-- therefor.

Signed and Sealed this
Twenty-third Day of April, 2019

Andrei Iancu
*Director of the United States Patent and Trademark Office*